US007166634B2

(12) United States Patent
Mitchell et al.

(10) Patent No.: US 7,166,634 B2
(45) Date of Patent: Jan. 23, 2007

(54) BIS-INDOLE PYRROLES USEFUL AS ANTIMICROBIALS AGENTS

(75) Inventors: Scott S. Mitchell, San Carlos, CA (US); Kin S. Lam, San Diego, CA (US); Jennifer Grodberg, Carlsbad, CA (US); Barbara C. Potts, Escondido, CA (US); Ginger Tsueng, San Diego, CA (US); Donald J. White, San Deigo, CA (US); Katherine Anne Reed, San Diego, CA (US)

(73) Assignee: Nereus Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 11/040,923

(22) Filed: Jan. 21, 2005

(65) Prior Publication Data

US 2005/0267192 A1 Dec. 1, 2005

Related U.S. Application Data

(60) Provisional application No. 60/627,235, filed on Nov. 12, 2004, provisional application No. 60/539,053, filed on Jan. 23, 2004.

(51) Int. Cl.
*A01N 43/38* (2006.01)
*A01N 43/36* (2006.01)
*C07D 209/10* (2006.01)

(52) U.S. Cl. .................. 514/414; 548/453; 548/455
(58) Field of Classification Search .............. 548/458; 514/414
See application file for complete search history.

(56) References Cited

U.S. PATENT DOCUMENTS

| 5,445,829 | A | 8/1995 | Paradissis et al. |
| 5,576,012 | A | 11/1996 | Bauer et al. |
| 5,641,515 | A | 6/1997 | Ramtoola |
| 5,653,987 | A | 8/1997 | Modi et al. |
| 5,654,286 | A | 8/1997 | Hostetler |
| 5,667,809 | A | 9/1997 | Trevino et al. |
| 5,683,676 | A | 11/1997 | Akehurst et al. |
| 5,688,529 | A | 11/1997 | Lidgate et al. |
| 5,707,615 | A | 1/1998 | Cardin et al. |
| 5,707,641 | A | 1/1998 | Gertner et al. |
| 5,726,181 | A | 3/1998 | Hausheer et al. |
| 5,733,888 | A | 3/1998 | Carver et al. |
| 5,874,443 | A | 2/1999 | Kiely et al. |
| 5,886,210 | A | 3/1999 | Rayle et al. |
| 5,922,683 | A | 7/1999 | Or et al. |
| 6,350,759 | B1 | 2/2002 | Casara et al. |
| 6,500,825 | B1 | 12/2002 | Lan et al. |
| 6,506,787 | B1 | 1/2003 | Fujishita et al. |
| 6,509,331 | B1 | 1/2003 | Audia et al. |
| 6,569,830 | B1* | 5/2003 | Climo et al. ............ 514/2 |
| 6,589,977 | B1 | 7/2003 | Sodeoka et al. |

FOREIGN PATENT DOCUMENTS

| EP | 0 612 742 A1 | 8/1994 |
| EP | 1 057 484 A1 | 12/2000 |
| EP | 1 152 002 A1 0 | 11/2001 |
| EP | 1 352 906 A1 | 10/2003 |
| WO | WO 91/04975 | 4/1991 |
| WO | WO 00/33836 | 6/2000 |
| WO | WO 02/055725 A2 | 7/2002 |
| WO | WO 02/057254 A1 | 7/2002 |
| WO | WO 02/068424 A1 | 9/2002 |

OTHER PUBLICATIONS

Adrian, P.V. et al., Antimicrob Agents Chemother, 44:3101 (2000).
Alm et al., Prog. Clin. Biol. Res., 312:447-58 (1989).
Buchanan, Malcom S., et al., Phytochemistry 41(3):791-793, (1996).
Bull, A.T. et al., Microbiol Mol Biol Rev 64:573, (2000).
Choe, C.H. et al., Antimicrob Agents Chemother 44:1766 (2000).
Cragg, G.M. & D.J. Newman, Trends Pharmacol Sci 23:404, (2002).
Eliopoulos, G.M. & C.B. Wennersten, Antimicrob Agents Chemother 46:1319 (2002).
Faulkner, D.J , Nat Prod Rep 18:1, 2001.
Fingl et al., in The Pharamacological Basis of Therapeutics, (1975).
Frode et al. Tetrahedron Lett. 35:1689-1690 (1994), related document, not cited.
Grayson, M (Ed.) "Antibiotics, Chemotherapeutics and Antibacterial Agents for Disease Control", (1982).
Hashimoto et al., Tetrahedron Letters 35:2559-2560 (1994).
Hashimoto, T. et al., "Structures of new polyacetylene triglycerides and indolocarbazoles from the myxomycetes Lycogala epidendrum" Tennen Yuki Kagobutsu Toromnkai Koen Yoshishu 34th, 470-477 (1992).
Higuchi T. and Stella, V., "Pro-drugs as Novel Delivery Systems", vol. 14, A.C.S. Symposium Series, American Chemical Society (1975).
Hoellman, D.B. et al., Antimicrob Agents Chemother 42:857, (1998).
Hoshino et al. Biosci, Biotech, Biochem, 57, 775-781 (1993), related but not cited.
Joshi, A., J Ocul Pharmacol 10:29-45, (1994).
Kerr, R.G. & S.S. Kerr, Exp Opin Ther Patents 9:1207, (1999).
Mayer et al., Ophthalmologica, 210(2):101-3 (1996).

(Continued)

*Primary Examiner*—Kamal A. Saeed
*Assistant Examiner*—Yong Chu
(74) *Attorney, Agent, or Firm*—Knobbe Martens Olson & Bear LLP

(57) ABSTRACT

Compounds of Formula I, commonly referred to as bis-indole pyrroles, including isolated naturally-occurring compounds, synthetic and semi-synthetic derivatives thereof having antimicrobial properties and to antimicrobial compositions that include one or more of bis-indole pyrroles and their derivatives or analogs having antimicrobial properties are disclosed. Pharmaceutical compositions comprising such compounds and methods of treating bacterial infections with the disclosed compounds or the disclosed pharmaceutical compositions are also disclosed.

13 Claims, 17 Drawing Sheets

OTHER PUBLICATIONS

Mayer, A. M. & V.K. Lehmann, Anticancer Res 21:2489, (2001).
Moore, B.S, Nat Prod Rep 16:653, (1999).
Mordenti, Toxicol. Sci., 52(1):101-6 (1999).
Okami, Y., J Mar Biotechnol 1:59, (1993).
Onaka, Characterization of the Biosynthetic Gene Cluster of Rebeccamycin from Lechevalieria aerocolonigenes ATCC 39243. Biosci.Biotechnol.Biochem., 67 (1), 127-138, (2003), cited p. 133, Line 3.
Remington's Pharmaceutical Sciences, 18th Ed., Mack Publishing Co., Easton, PA(1990).
Roche E.B. (Ed.) "Bioreversible Carriers in Drug Design: Theory and Application", Pergamon Press: New York, 14-21 (1987).
Sánchez, Combinatorial biosynthesis of antitumor indolocarbazole compounds. PNAS vol. 102 No. 2, 461-466, (Jan. 11, 2005).
Shedden et al., Clin. Ther., 23(3):440-50, (2001).

* cited by examiner

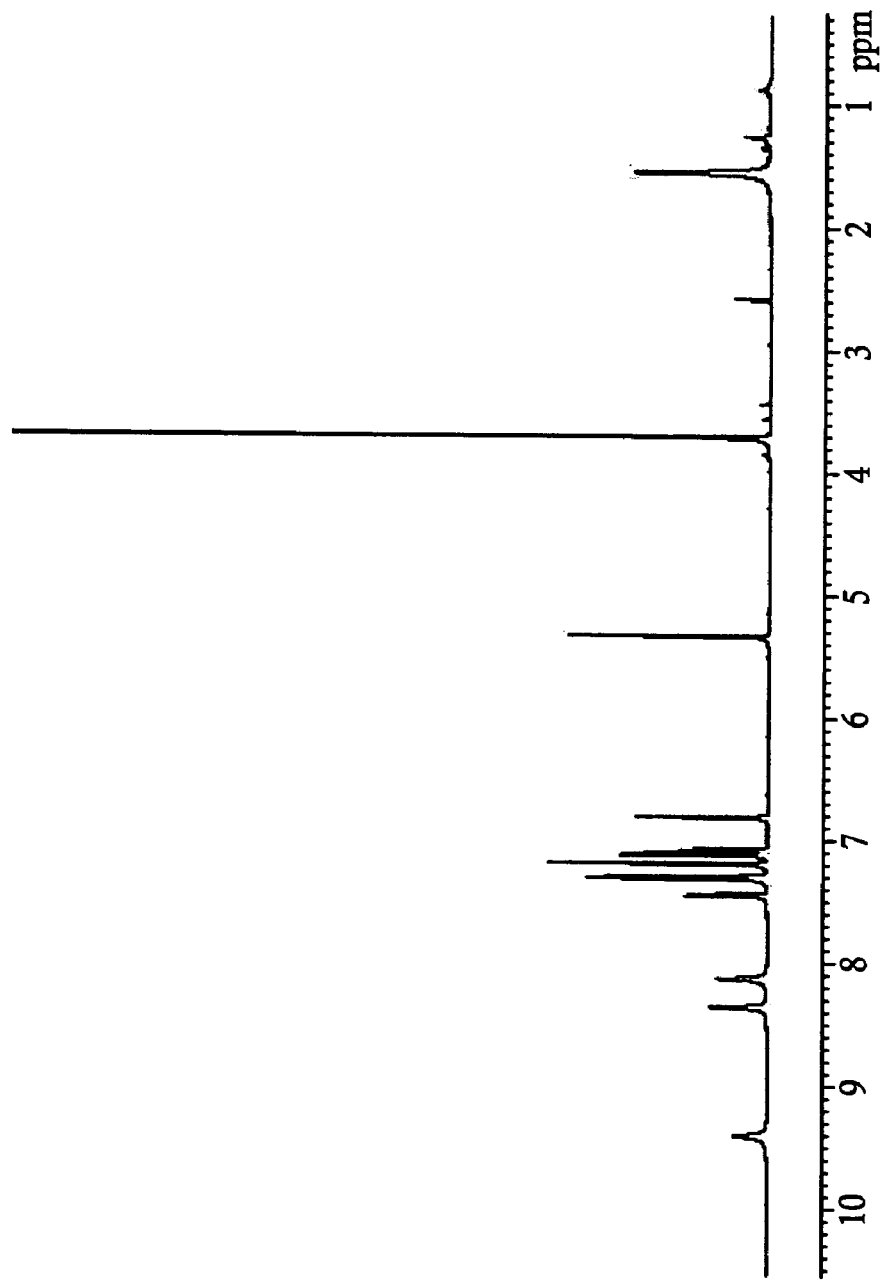

BIS-INDOLE PYRROLES USEFUL AS ANTIMICROBIALS AGENTS

RELATED APPLICATIONS

This Application claims priority to U.S. Provisional Application No. 60/539,053, filed Jan. 23, 2004 and U.S. Provisional Application No. 60/627,235, filed Nov. 12, 2004, herein incorporated by reference in their entireties.

BACKGROUND OF THE INVENTION

1. Field of the Invention

The present invention relates to certain compounds and to methods for the preparation and the use of certain compounds in the fields of chemistry and medicine. More specifically, the present invention relates to compounds and procedures for making and using compounds that are useful as antimicrobial agents, and relates to pharmaceutical dosage forms comprising such compounds.

2. Description of the Related Art

Antimicrobials are generally used to destroy or suppress the growth or reproduction of microbes such as bacteria. Antimicrobial compounds may act on the targeted microbes in a variety of ways. For example, the antimicrobial compound may prevent DNA or protein synthesis, may alter the cell wall of a microbe, either by altering cell wall permeability or by altering cell wall synthesis and repair.

While there are numerous known antimicrobial compounds, and numerous known mechanisms by which antimicrobial compounds may function, concerns over the availability of antibiotic treatment options, for both early- and late-stage infections from bacteria, have recently increased. There are many reasons for the increase in concern, but one major reason relates to the potential of bioweapons engineering of resistant isolates, and evolutionary development of resistance to existing antibiotics. As such, new antimicrobials and new sources of antimicrobials are desired and are increasingly valuable.

There are many characteristics that can be relevant when trying to decide whether or not a particular compound is useful as an antimicrobial. Relevant factors include, but are not limited to, the relative potency of the compound against a specific microbe or against a spectrum of microbes, and the relative selectivity of the antimicrobial activity of the compound in targeting the invading pathogen versus the host organism. There are also long-term concerns, including the likelihood that the microbe may develop resistance to one or more antimicrobial compound. There are also practical concerns, such as the cost and commercial availability of the antimicrobial compound.

A possible source of antimicrobial compounds is marine-derived natural products. The oceans are massively complex and house a diverse assemblage of microbes that occur in environments of extreme variations in pressure, salinity, and temperature. Marine microorganisms have developed unique metabolic and physiological capabilities that not only ensure survival in extreme habitats, but also offer the potential to produce metabolites that would not be observed from terrestrial microorganisms. (Okami, Y. 1993 *J Mar Biotechnol* 1:59.) Representative structural classes of such metabolites include terpenes, peptides, polyketides, and compounds with mixed biosynthetic origins. Many of these molecules exhibit anti-tumor, anti-bacterial, anti-fungal, anti-inflammatory or immunosuppressive activities (Bull, A. T. et al. 2000 *Microbiol Mol Biol Rev* 64:573; Cragg, G. M. & D. J. Newman 2002 *Trends Pharmacol Sci* 23:404; Kerr, R. G. & S. S. Kerr 1999 *Exp Opin Ther Patents* 9:1207; Moore, B. S 1999 *Nat Prod Rep* 16:653; Faulkner, D. J. 2001 *Nat Prod Rep* 18:1; Mayer, A. M. & V. K. Lehmann 2001 *Anticancer Res* 21:2489), validating the utility of this source for isolating therapeutic agents. Further, the isolation of novel antibiotics that represent alternative mechanistic classes to those currently on the market will likely address mechanism-based resistance that may have been engineered into pathogens for bioterrorism purposes.

One such class of compounds, studied in other, unrelated, fields of research, is the bis-indole pyrrole and, in particular, chromopyrrolic acid. A subset of this class of molecules is disclosed by Hoshino et al. (Biosci, Biotech, Biochem, 57, 775–781 (1993)). Hashimoto et al. (Tetrahedron Letters 35:2559–2560 (1994) suggests that one particular derivative, a doubly substituted pyrrole with two methoxy carbonyls attached symmetrically to the pyrrole, had moderate anti-HSV-1 virus activity in vitro. The functionality of this compound, and of its analogs, is not well understood. Other references have examined similar derivatives for these compounds (Frode et al. Tetrahedron Lett. 35:1689–1690 (1994)).

More recently, Sodeoka et al., (U.S. Pat. No. 6,589,977, issued Jul. 8, 2003), which is incorporated by reference herein, has suggested a role for bis-indole pyrrole derivatives as cell death inhibitors. Sodeoka et al. examined several different bis-indole pyrrole derivatives for cell death inhibitory activity.

SUMMARY OF THE INVENTION

In some aspects, a compound having a structure of Formula I, and pharmaceutically acceptable salts and pro-drug esters thereof is provided:

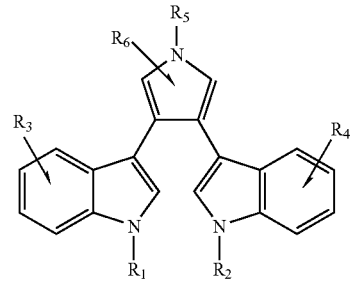

Formula I

A ring can include one or more additional hetero-atoms, such as nitrogen, sulfur or oxygen; and can include a non-nitrogen hetero-atom, such as sulfur or oxygen, in place of a nitrogen(s) in Formula I; each of $R_1$, $R_2$, and $R_5$ is separately selected from the group consisting of hydrogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, halogenated alkyl including polyhalogenated alkyl, and some combination thereof; each of five $R_3$ and each of five $R_4$ represent substituent(s) on an indole ring at a 2-, 4-, 5-, 6-, or 7-position(s) and each of the five $R_3$ and each of the five $R_4$ is separately selected from the group consisting of hydrogen atom, halogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, halogenated alkyl including polyhalogenated alkyl, and some combination thereof; $R_6$ represents substituent(s) on a pyrrole ring at a 2- or a 5-position(s), and each of the two $R_6$ is separately selected from the group consisting of hydrogen atom, halogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, acyloxy, ester, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, halogenated alkyl including polyhalogenated alkyl, and some combination thereof. In some embodiments, there is the proviso that if all $R_3$ and $R_4$ are either hydrogen or hydroxyl $R_6$ at the 5-position and $R_6$ at the 2-position are not identical esters or carboxylic acids. In some embodiments there is the further proviso when the substituents on $R_3$ are identical to the substituents on $R_4$, the substituents on $R_6$ at the 5-position and the 2-position are not the same.

In another aspect, a compound having a structure of Formula I, and pharmaceutically acceptable salts and prodrug esters thereof is provided:

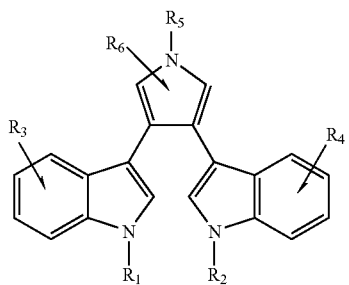

Formula I

A ring can include one or more additional hetero-atoms, such as nitrogen, sulfur or oxygen; and can include a non-nitrogen hetero-atom, such as sulfur or oxygen, in place of a nitrogen(s) in Formula I, each of $R_1$, $R_2$, and $R_5$ is separately selected from the group consisting of hydrogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, sugar, aminocarbonyl, aminocarboyloxy, nitro, azido, phenyl, hydroxy, alkylthio, arylthio, oxysulfonyl, carboxy, cyano, CO—O—$R_7$, carbonyl —CCO—$R_7$, —$(CH_2)_n$—COOR$_7$, —CO—$(CH_2)_n$—COOR$_7$, aminoalkyl (—$(CH_2)_n$—NR$_8$R$_9$), and halogenated alkyl including polyhalogenated alkyl, wherein n is an integer from 1 to 6; each $R_7$, $R_8$ and $R_9$ is separately selected from the group consisting of a hydrogen atom, halogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl, a 5-membered ring, a 6-membered ring, or combination thereof; each of five $R_3$ and each of five $R_4$ represent substituent(s) on an indole ring at a 2-, 4-, 5-, 6-, or 7-position(s) and each of the five $R_3$ and each of the five $R_4$ is separately selected from the group consisting of hydrogen atom, halogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl; each of two $R_6$ represent substituent(s) on a pyrrole ring at a 2- or 5-position(s), and each of the two $R_6$ is separately selected from the group consisting of hydrogen atom, halogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, acyloxy, amide (—CO—NR$_8$R$_9$), alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, ester, alkoxycarbonyl, aryloxycarbonyl, CO—O—$R_7$, carbonyl —CCO—$R_7$, —$(CH_2)_n$—COOR$_7$, —CO—$(CH_2)_n$—COOR$_7$, alkylthio, arylthio, oxysulfonyl, carboxy, cyano, and halogenated alkyl including polyhalogenated alkyl. In some embodiments, there is the further proviso that $R_6$ at the 5-position and $R_6$ at the 2-position are not identical if all $R_3$ and $R_4$ are either hydrogen or hydroxyl. In some embodiments, there is the further proviso that if there is 1) an alkyl group at $R_5$ and if 2) $R_6$ at the 2-position and the 5-position is either hydrogen or oxygen, then $R_3$ and $R_4$ are not symmetrical. In some embodiments there is the further proviso that if there is an alkylamine at $R_1$ or $R_2$, then there is at least one non-hydrogen substitution at R6, or there are at least 3 halogens at $R_3$ and $R_4$.

In another aspect, a compound having a structure of Formula I, and pharmaceutically acceptable salts and prodrug esters thereof is provided:

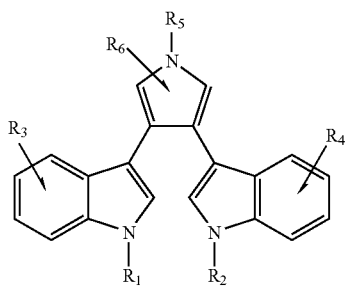

Formula I

A ring can include one or more additional hetero-atoms, such as nitrogen, sulfur or oxygen; and can include a non-nitrogen hetero-atom, such as sulfur or oxygen, in place of a nitrogen(s) in Formula I; each of $R_1$, $R_2$, and $R_5$ is separately selected from the group consisting of hydrogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyloxy, alkyloxycarbonyloxy, aryloxycarbonyloxy, cycloalkyl, cycloalkenyl, alkoxy, acyl, cycloalkoxy, aryl, heteroaryl, arylalkoxy carbonyl, alkoxy carbonylacyl, amino, carbohydrate, aminocarbonyl, aminocarboyloxy, nitro, azido, phenyl, hydroxy, alkylthio, arylthio, oxysulfonyl, carboxy, cyano, —CO—O—$R_7$, carbonyl —CCO—$R_7$, —$(CH_2)_n$—

COOR₇, —CO—(CH₂)ₙ—COOR₇, —CH₂)ₙ—NR₈R₉, and halogenated alkyl including polyhalogenated alkyl, wherein n is an integer between 1 and 6; each R₇, R₈, and R₉ is separately selected from the group consisting of a hydrogen atom, halogen atom, mono-substituted, poly-substituted or unsubstituted variants of the following residues: saturated $C_1-C_{24}$ alkyl, unsaturated $C_2-C_{24}$ alkenyl or $C_2-C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl, a 5-membered ring, a 6-membered ring, or combination thereof; the five $R_3$ and the five $R_4$ represent substituent(s) on an indole ring at a 2-, 4-, 5-, 6-, or 7-position(s), wherein each of the five $R_3$ and each of the five $R_4$ is separately selected from the group consisting of hydrogen atom, halogen atom, mono-substituted, poly-substituted or unsubstituted variants of the following residues: saturated $C_1-C_{24}$ alkyl, unsaturated $C_2-C_{24}$ alkenyl or $C_2-C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl; each of two $R_6$ represent substituent(s) on a pyrrole ring at a 2- or a 5-position(s), and each of the two $R_6$ is separately selected from the group consisting of hydrogen atom, halogen atom, mono-substituted, poly-substituted or unsubstituted variants of the following residues: saturated $C_1-C_{24}$ alkyl, unsaturated $C_2-C_{24}$ alkenyl or $C_2-C_{24}$ alkynyl, acyl, acyloxy, —CO—NR₈R₉, CO—O—R₇, carbonyl —CCO—R₇, —(CH₂)ₙ—COOR₇, —CO—(CH₂)ₙ—COOR₇, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, ester, —(CH₂)ₙ—NR₈R₉, alkoxycarbonyl, aryloxycarbonyl, and halogenated alkyl including polyhalogenated alkyl. In some embodiments, there is the added proviso that $R_6$ at the 5-position and $R_6$ at the 2-position are not identical. In some embodiments there is the further proviso that if there is an alkylamine at $R_1$, or $R_2$, then there is at least one non-hydrogen substitution at $R_6$, or there are at least 3 halogens in the combination of $R_3$ and $R_4$. In some further embodiments, the ring atoms on these compounds are not modified.

In some embodiments, the compounds above have at least two of the five $R_3$ are hydrogen atoms and at least two $R_4$ are hydrogen atoms. In some embodiments, the compounds above have at least one of the five $R_3$ is a halogen atom and the indole rings do not include additional hetero-atoms, but do include the indole nitrogen. In some embodiments, the compounds above have at least one of the five $R_3$ is a halogen atom and at least one of the five $R_4$ is a halogen atom. In some embodiments, the compounds above have at least two of the five $R_3$ is a halogen atom. In some embodiments, the compounds above have at least one of the five $R_3$ is a chlorine atom. In some embodiments, the compounds above have one of the two $R_6$ is an alkoxy carbonyl, one of the $R_6$ is a hydrogen atom, at least one of the five $R_3$ is a chloride atom, and $R_1$, $R_2$, and $R_5$ are each hydrogen atoms. In some embodiments, the compounds above have one of the two positions at $R_6$ is an alkoxy carbonyl. In some embodiments, the compounds above have $R_6$ as a methoxy carbonyl. In some embodiments, the compounds above have the structure selected from the group consisting of the structures of Formulae II, V, III, IV, VI, VII, VIII, XI, XII, XIII, XIV, XV, XV', XVI, XVII, XVIII, XIX, XIX', XX, XXI', XXI, XXII, XXIII, XXIV, XXV, XXVI, XXVII, XXVII-A, XXVII-B, XXVII-C, XXVIII, XXVIII-A, XXIX, XXIX-A, XXX, XXXI, XXXI-A and XXXI-B and pharmaceutically acceptable salts and pro-drug esters thereof. In some embodiments, the compounds above have the structure of Formula II, and pharmaceutically acceptable salts and pro-drug esters thereof:

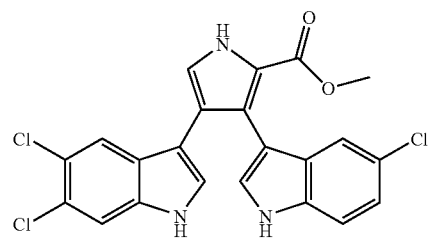

Formula II

In some embodiments, the compounds above have at least two of the ten $R_3$ and $R_4$ are halogen atoms. In some embodiments, the compounds above have at least three of the ten $R_3$ and $R_4$ are halogen atoms. In some embodiments, the compounds above have at least two of the ten $R_3$ and $R_4$ are chlorine atoms. In some embodiments, the compounds above have at least three of the ten $R_3$ and $R_4$ are chlorine atoms. In some embodiments, the compounds above have at least two of the ten $R_3$ and $R_4$ are bromine atoms. In some embodiments, the compounds above have at least three of the ten $R_3$ and $R_4$ are bromine atoms.

In some aspects, the compounds above are part of a pharmaceutical composition. In some embodiments, the compounds above have an antimicrobial agent. In some embodiments, the compounds above are in a solid unit dosage form.

In some aspects, a method of treating a microbial infection is provided. The method comprises administering a compound having a structure of Formula I, and pharmaceutically acceptable salts and pro-drug esters thereof:

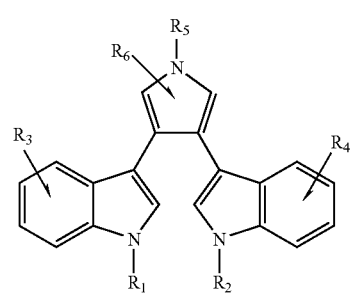

Formula I

A ring can include one or more additional hetero-atoms, such as nitrogen, sulfur or oxygen; and can include a non-nitrogen hetero-atom, such as sulfur or oxygen, in place of a nitrogen(s) in Formula I; each of a $R_1$, a $R_2$, five $R_3$, five $R_4$, a $R_5$, and two $R_6$ is independently selected from the group consisting of a hydrogen atom, a halogen, a sugar, an aminoalkyl, mono-substituted, poly-substituted or unsubstituted variants of the following residues: saturated $C_1-C_{24}$ alkyl, unsaturated $C_2-C_{24}$ alkenyl or $C_2-C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl, —CO—O—$R_7$, carbonyl —CCO—$R_7$, —CO—$NR_8R_9$, —$(CH_2)_n$—$COOR_7$, —CO—$(CH_2)_n$—$COOR_7$, —$(CH_2)_n$—$NR_8R_9$, ester, alkoxycarbonly, aryloxycarbonly, and n is an integer from 1 to 6; each $R_7$, $R_8$ and $R_9$ is separately selected from the group consisting of a hydrogen atom, halogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl, a 5-membered ring, a 6-membered ring, or combination thereof.

In some embodiments, at least one of the $R_1$, $R_2$, the five $R_3$, the five $R_4$, $R_5$, and the two $R_6$ substitutions is asymmetric. In some embodiments, the two $R_6$ substitutions are asymmetric. In some embodiments, the five $R_4$ and the five $R_3$ substitutions are asymmetric. In some embodiments, at least of the five $R_3$ is a halogen atom and at least one $R_4$ is a halogen atom, and the indole rings do not include additional hetero-atoms, but do include the indole nitrogen. In some embodiments, $R_8$ is —$(CH_2)_2$— and $R_9$ is —$(CH_2)_2$—, and $R_8$ and $R_9$ are directly connected to each other so as to form a five membered ring. In some embodiments, $R_8$ is —$(CH_2)_2$— and $R_9$ is —$(CH_2)_2$—, and $R_8$ and $R_9$ are connected to each other via $R_{10}$ so as to form a six membered-ring, and $R_{10}$ is selected from the group consisting of $CH_2$, NH, O, and S. In some embodiments, one of the two $R_6$ is an alkoxy carbonyl, one of the $R_6$ is a hydrogen atom, at least one of the five $R_3$ is a chloride atom, and $R_1$, $R_2$, and $R_5$ are each hydrogen atoms. In some embodiments, the alkoxy carbonyl is a methoxy carbonyl. In some embodiments, the methods above further comprise the steps of identifying a subject that would benefit from administration of an antimicrobial agent, and performing the method on the subject. In some embodiments, the microbial infection is an infection of at least one a gram positive bacterium. In some embodiments, the microbial infection is an infection of at least *E. faecalis*-Vans. In some embodiments, the microbial infection is an infection of at least *H. influenzae*. In some embodiments, any of the above compounds or the herein disclosed compounds can be used for treating a microbial infection.

In one aspect a method of treating a microbial infection is provided. The method comprises administering a compound having a structure selected from the group consisting of Formula I, II, III, IV, V, VI, VII, VIII, IX, X, XI, XII, XIII, XIV, XV, XV', XVI, XVII, XVIII, XIX, XIX', XX, XXI, XXI', XXII, XXIII, XXIV, XXV, XXVI, XXVII, XXVII-A, XXVII-B, XXVII-C, XXVIII, XXVIII-A, XXIX, XXIX-A, XXX, XXXI, XXXI-A, and XXXI-B, and 1) a pharmaceutically acceptable salt or 2) pro-drug ester thereof. In some embodiments, the compound has a structure selected from the group consisting of Formula II, III, IV, VI, V, VII, VIII, IX, X, XI, XII, XIII, XIV, XV, XV', XVI, XVII, XVIII, XIX, XIX', XX, XXI, XXI', XXII, XXIII, XXIV, XXV, XXVI, XXVII, XXVII-A, XXVII-B, XXVII-C, XXVIII, XXVIII-A, XXIX, XXIX-A, XXX, XXXI, XXXI-A, and XXXI-B.

In some aspects, a method of making a compound described above is provided. The method comprises growing strain NPS012745 in a culture, and recovering the compound of formula I from the culture. In some embodiments, the method further comprises the step of isolating a single compound analog of bis-indole pyrrole. In some embodiments, the single compound is a compound described above.

As will be appreciated by one of skill in the art, in some embodiments, any of the above compounds can be used for any of the methods of treatment. Likewise, in some embodiments, any of the compounds of the disclosed methods can also be useful in and of themselves.

Disclosed methods can also include steps of obtaining and purifying the above-compound as described in further detail herein. Semi-synthetic and synthetic methods are also disclosed.

Other embodiments relate to methods of treating an individual using certain compounds disclosed herein and compositions comprising the compounds disclosed herein.

BRIEF DESCRIPTION OF THE DRAWINGS

The accompanying drawings, which are incorporated in and form part of the specification, merely illustrate certain preferred embodiments of the present invention. Together with the remainder of the specification, they are meant to serve to explain preferred modes of making certain compounds of the invention to those of skilled in the art. In the drawings:

FIG. 3I depicts the $^1$H NMR spectrum of the compound of Formula XXII.

DETAILED DESCRIPTION OF THE PREFERRED EMBODIMENTS

Figure 1:
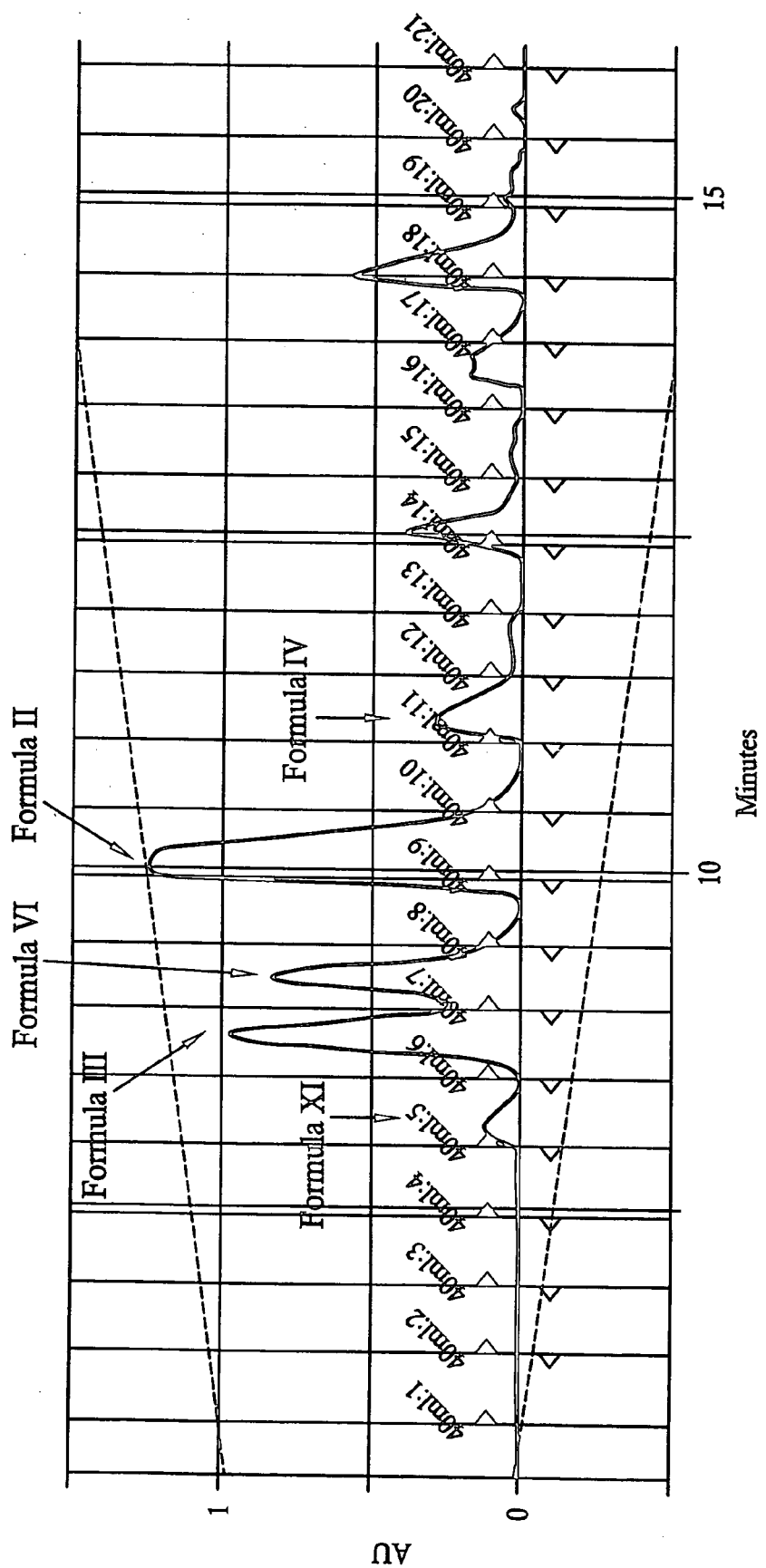
FIG. 1 depicts an HPLC chromatograph of a compound of the invention, showing the various points of the various structures.

Numerous references are cited herein. The references cited herein, including the U.S. patents cited herein, are each to be considered incorporated by reference in their entirety into this specification. The definitions provided herein are controlling over any conflicting definitions from references incorporated by reference.

Embodiments of the invention include, but are not limited to, providing a method for the preparation of compounds, including novel compounds, including bis-indole pyrroles and analogs thereof, and to providing a method for producing pharmaceutically acceptable antimicrobial compositions, for example. The methods can include the compositions in relatively high yield, wherein the compounds and/or their derivatives are among the active ingredients in these compositions. Other embodiments relate to providing novel compounds not obtainable by currently available methods. Furthermore, embodiments relate to methods of treating infectious diseases, particularly human infectious diseases, particularly those caused by microbes, comprising the step of administering an effective amount of a member of a class of new compounds. Preferred embodiments relate to the compounds and methods of making and using such compounds disclosed herein, but not necessarily in all embodiments of the present invention, these objectives are met.

The embodiments provide compounds, and methods of producing a class of compounds, wherein the compounds are represented by Formula I:

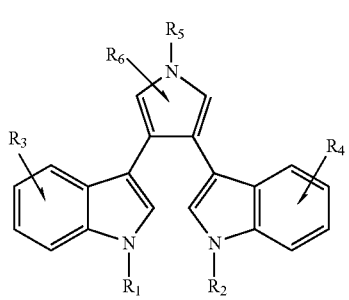

Formula I

The disclosed compounds have the structure of the above Formula I. In certain embodiments, the ring(s) contains one or more additional hetero-atoms and can include another hetero-atom in place of the nitrogen(s). The ring structure can be freely substituted according to the skill in the art. In a more preferred embodiment, only the sections explicitly identified as $R_1$–$R_6$ are substituted, although multiple substitutions are allowed.

In certain embodiments the substitution(s) to $R_1$–$R_6$ can include the substitution of a hydrogen atom, halogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl, and can also include ester, alkoxycarbonyl, aryloxycarbonyl, carbonyl —CCO—$R_7$, —$(CH_2)_n$—$COOR_7$, —CO—$(CH_2)_n$—$COOR_7$, amide, alkylamine, sugar, —CO—O—$R_7$, and carbonyl —CCO—$R_7$, wherein $R_7$ is selected from a hydrogen atom, a halogen atom, and saturated $C_1$–$C_{24}$ alkyl, unsaturated $C_1$–$C_{24}$ alkenyl, cycloalkyl, cycloalkenyl, alkoxy, cycloalkoxy, aryl, substituted aryl, heteroaryl, substituted heteroaryl, amino, substituted amino, nitro, azido, substituted nitro, phenyl, substituted phenyl groups, and the like. It certain preferred embodiments, $R_6$ at the 5-position and $R_6$ at the 2-position are not identical esters or identical carboxylic acid groups, if all $R_3$ and $R_4$ are either hydrogen or hydroxy, or alternatively $R_6$ at the 5-position and $R_6$ at the 2-position are not identical if all $R_3$ and $R_4$ are either hydrogen or hydroxy, or alternatively, $R_6$ at the 5-position and $R_6$ at the 2-position are not identical.

In some embodiments, amides (—CO—$NR_8R_9$) are included as a possible substitution(s) to $R_1$–$R_6$. In some embodiments, the amide is a substituent on $R_6$ only. In some embodiments, when there is an amide, there are at least three halides on the combination of $R_3$ and $R_4$. $R_8$ and $R_9$, can be independently selected from a hydrogen, saturated $C_1$–$C_6$ alkyl, unsaturated $C_1$–$C_6$ alkenyl, cycloalkyl, cycloalkenyl, hydroxy, alkoxy, cycloalkoxy, aryl, substituted aryl, heteroaryl, substituted heteroaryl, phenyl, and substituted phenyl groups. In some embodiments, $R_8$ and $R_9$ can be selected from a list of possible substituents for $R_7$. In some embodiments, $NR_8R_9$ comprises a ring. That is, when taken together, $R_8$ and $R_9$ can form a ring, for example, —$(CH_2)_4$— or —$(CH_2)_2$—$R_{10}$—$(CH_2)_2$— to form a 5- or 6-membered ring together with the N-atom wherein $R_{10}$ is selected from $CH_2$, NH, O and S.

In certain embodiments the substituents at $R_1$–$R_6$ include sugars, such as substituted or unsubstituted, mono-, di-, or poly-saccharides or amino sugars. In some embodiments, when there is a sugar, the $R_3$ and $R_4$ substituents will include at least three halogens. In some embodiments, $R_1$, $R_2$ and $R_5$ are the only substituents in Formula I that can include sugars or substituted alkyl groups such as —$(CH_2)_n$—$COOR_7$, —CO—$(CH_2)_n$—$COOR_7$, aminoalkyl (—$(CH_2)_n$—$NR_8R_9$) or salts thereof. In these examples, n is an integer from 1 to 6 and $R_7$ is selected from the possible $R_7$ substituents described above.

In one embodiment, the antimicrobial comprises any bis-indole pyrrole. In preferred embodiments, any of the above substitutions to Formula I, at any of positions $R_1$–$R_6$ are contemplated. In preferred embodiments, while $R_1$–$R_5$ are allowed to be substituted with any of the above mentioned possible substitutions, each $R_6$ is separately selected from the group consisting of an alkoxy carbonyl and a carboxyl group. In preferred embodiments, the two $R_6$ are two methoxy carbonyls. In other preferred embodiments, $R_6$ is a single methoxy carbonyl. In another embodiment, $R_6$ is two carboxyls. In preferred embodiments, $R_6$ is a single carboxyl group.

In one embodiment, the general class of bis-indole pyrroles and analogs of bis-indole pyrroles include substitution(s) in $R_1$, $R_2$, $R_3$, $R_4$, and $R_5$ that can, independently, be any of the previously mentioned substitutions, including multiple substitutions where permissible, with the proviso that substitution(s) in $R_6$ are limited to asymmetric substitutions. In other words, the substitution at position 2 and position 5 of the pyrrole cannot be the same. In a more preferred embodiment, the asymmetric substitution comprises an alkoxy carbonyl. In an even more preferred substitution, the alkoxy carbonyl is located at position 2 of the pyrrole ring. In a yet more preferred embodiment, the alkoxy carbonyl is a methoxy carbonyl. In an alternative embodiment, the substitution at $R_6$ is a single carboxyl. In an alternative embodiment, while the substitutions in $R_6$ are only limited to asymmetric substitutions, there cannot be a bond between position 2 of the two indoles. In an even more preferred embodiment, the base structure demonstrated in Formula I cannot be different, except as explicitly noted by the symbols $R_1$–$R_6$.

In another embodiment, substitution(s) in $R_1$, $R_2$, $R_5$, and $R_6$ can, independently, be any of the previously mentioned substitutions, including multiple substitutions where permissible, while substitution(s) in $R_3$ and $R_4$ comprise at least one halogen. In another embodiment, the only non-hydrogen substitutions in $R_3$ and $R_4$ are Cl atoms. In another embodiment, $R_3$ represents substitutions of two chloride atoms at positions 5 and 6 of the indolyl, while position 2 of the pyrrole is an alkoxy carbonyl. In one embodiment, the substitutions in $R_3$ and $R_4$ are asymmetric substitutions comprising at least one halogen atom. In another embodiment, the substitutions at $R_3$ and $R_4$ are symmetric, but the substitution(s) is selected from the group of halogens, including Cl, F, Br, and I. In another embodiment, while the substitution is symmetric, the identity of the substitution on each indolyl is different. For example, in such an embodiment, $R_3$ can be a Cl atom at position 5 of the indolyl ring, while $R_4$ can be a F atom at position 5 of the indolyl ring. Further, $R_3$ and $R_4$ can be symmetric or asymmetric substitutions on the indole.

In another embodiment, at least one of the substitution(s) at $R_3$ and/or $R_4$ comprises a halogen atom and $R_6$ is an asymmetrical substitution. In a preferred embodiment, while at least one of $R_3$ and/or $R_4$ comprises a halogen atom, $R_6$ comprises an asymmetrical acyl group with optional additional substitutions on it. In another preferred embodiment, while at least one of $R_3$ and/or $R_4$ comprises a halogen, $R_6$ comprises a carboxyl group. In another preferred embodiment, while at least one of $R_3$ and/or $R_4$ comprises a halogen, $R_6$ comprises an alkoxy carbonyl. In one embodiment, in the previous compounds, $R_1$, $R_2$, and $R_5$ are preferably hydrogen atoms.

Numbering conventions for each of the rings is as follows. For substitutions to the pyrrole, the nitrogen is position 1, while the first carbon in a clockwise rotation (as the molecule is shown in formula I) is position 2; thus, the carbon to the left of the nitrogen, as shown in Formula I, is position 5. For substitutions to the indole on the right side of the structure displayed in Formula I, the nitrogen is position 1', while the first carbon in a clockwise direction, with the indole as the center, is position 2'. Position 3' forms a bond with the pyrrole, the next carbon is 3a', while the next 4 carbons are numbered 4'-7', leaving the last carbon 7a', which forms a bond with 3a'. The numbering for the indole on the left side is similar, except the numbering goes in the counter clockwise direction, as the molecule is shown in formula I, from the nitrogen, 1", to carbon 7a". When reference is made to a particular pyrrole, the "'" symbol may be excluded, as it is not required as a reference.

In another embodiment, the compound has the structure of Formula II:

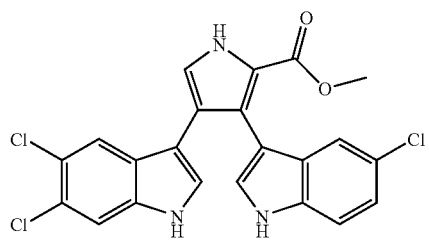

Formula II

For the compound of Formula II, and other compounds in which one or more indole ring has a substituent of one or more halogen atom, (for example, the compounds of Formulae III, IV, VI, VII, VIII, XI, XII, XIII, XIV, XV, XV', XVI, and XVII) the positions(s) of the halogen atom(s) (especially if that halogen atom is either a chlorine or a bromine atom) can be modified, provided the molecular formula is preserved. The compound of Formula II has a molecular formula of $C_{22}H_{14}Cl_3N_3O_2$, and a molecular weight of 458.73478.

In another embodiment, the compound has the structure of Formula III:

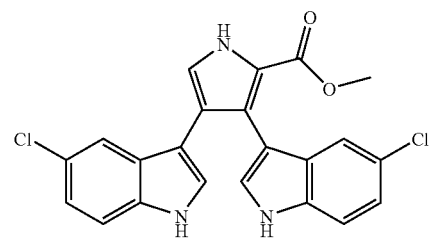

Formula III

The compound of Formula III has a molecular formula of $C_{22}H_{15}Cl_2N_3O_2$, and a molecular weight of 424.28975.

In another embodiment, the compound has the structure of Formula IV:

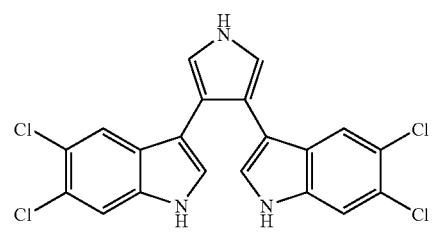

Formula IV

The compound of Formula IV has a molecular formula of $C_{20}H_{11}Cl_4N_3$, and a molecular weight of 435.14277.

In another embodiment, the compound has the structure of Formula VI:

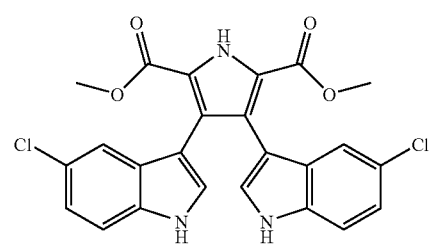

Formula VI

The compound of Formula VI has a molecular formula of $C_{24}H_{17}Cl_2N_3O_4$, and a molecular weight of 482.32679.

In another embodiment, the compound has the structure of Formula VII:

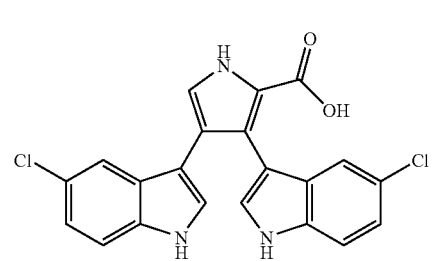

Formula VII

The compound of Formula VII has a molecular formula of $C_{21}H_{13}Cl_2N_3O_2$, and a molecular weight of 410.26266.

In another embodiment, the compound has the structure of Formula VIII:

Formula VIII

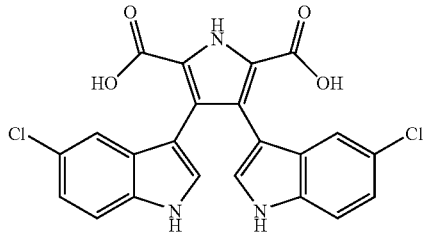

The compound of Formula VIII has a molecular formula of $C_{22}H_{13}Cl_2N_3O_4$, and a molecular weight of 454.27261.

In another embodiment, the compound has the structure of Formula IX:

Formula IX

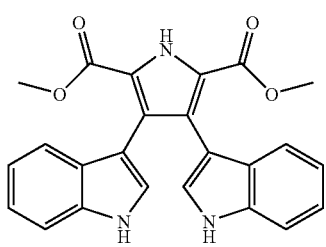

The compound of Formula IX has a molecular formula of $C_{24}H_{19}N_3O_4$, and a molecular weight of 413.43673.

In another embodiment, the compound has the structure of Formula X:

Formula X

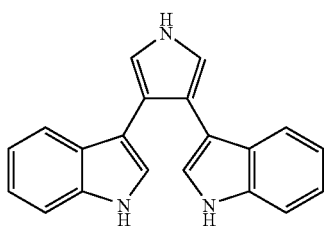

The compound of Formula X has a molecular formula of $C_{20}H_{15}N_3$, and a molecular weight of 297.36265.

In another embodiment, the compound has the structure of Formula XI:

Formula XI

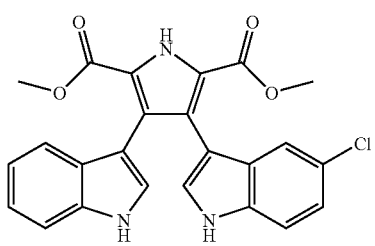

The compound of Formula XI has a molecular formula of $C_{24}H_{18}ClN_3O_4$, and a molecular weight of 447.88176.

In another embodiment, the compound has the structure of Formula XII:

Formula XII

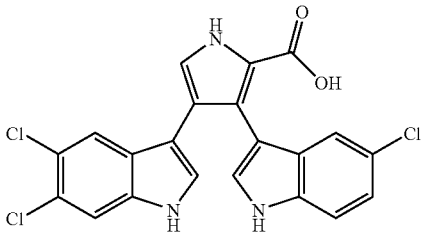

The compound of Formula VI has a molecular formula of $C_{21}H_{12}Cl_3N_3O_2$, and a molecular weight of 444.70769.

In another embodiment, the compound has the structure of Formula XIII:

Formula XIII

The compound of Formula XIII has a molecular formula of $C_{23}H_{17}ClN_4O_4$, a mass of 448.0938 and a molecular weight of 448.8583.

In another embodiment, the compound has the structure of Formula XIV:

Formula XIV

The compound of Formula XIV has a molecular formula of $C_{21}H_{14}Cl_2N_4O_2$, a mass of 424.04938 and a molecular weight of 425.26702.

In another embodiment, the compound has the structure of Formula XV:

Formula XV

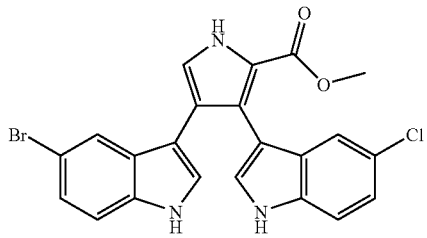

The compound of Formula XV has a molecular formula of $C_{22}H_{15}BrClN_3O_2$, a mass of 467.00362 and a molecular weight of 468.73022.

In another embodiment, the compound has the structure of Formula XVI:

Formula XVI

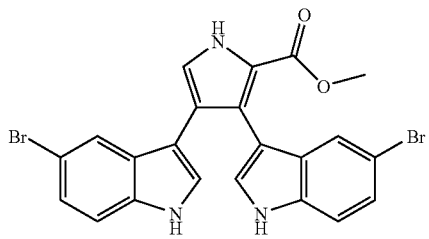

The compound of Formula XVI has a molecular formula of $C_{22}H_{15}Br_2N_3O_2$, a mass of 510.95310 and a molecular weight of 513.18152.

In another embodiment, the compound has the structure of Formula XVII:

Formula XVII

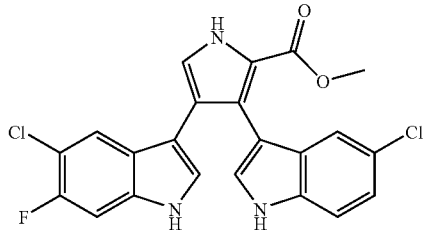

The compound of Formula XVII has a molecular formula of $C_{22}H_{14}Cl_2FN_3O_2$, a mass of 441.04471 and a molecular weight of 442.26938.

In another embodiment, the compound has the structure of Formula XVIII:

Formula XVIII

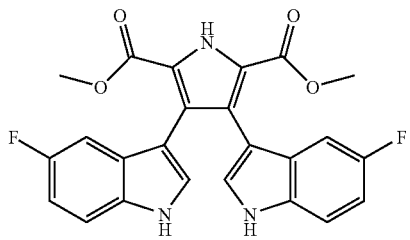

The compound of Formula XVIII has a molecular formula of $C_{24}H_{17}F_2N_3O_4$, a mass of 449.11871 and a molecular weight of 449.40641.

In another embodiment, the compound has the structure of Formula XIX:

Formula XIX

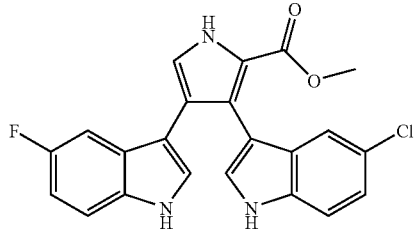

The compound of Formula XIX has a molecular formula of $C_{22}H_{15}ClFN_3O_2$, a mass of 407.08368 and a molecular weight of 407.82462.

In another embodiment, the compound has the structure of Formula XX:

Formula XX

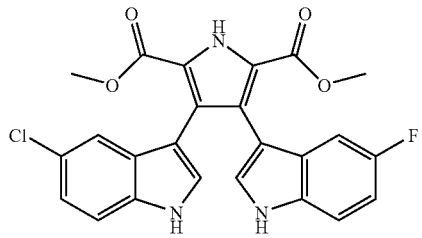

The compound of Formula XX has a molecular formula of $C_{24}H_{17}ClFN_3O_4$, a mass of 465.08916 and a molecular weight of 465.86070.

In another embodiment, the compound has the structure of Formula XXI:

Formula XXI

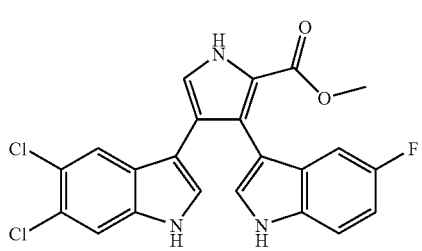

The compound of Formula XXI has a molecular formula of $C_{22}H_{14}Cl_2FN_3O_2$, a mass of 441.04471 and a molecular weight of 442.26938.

In another embodiment, the compound has the structure of Formula XXII:

Formula XXII

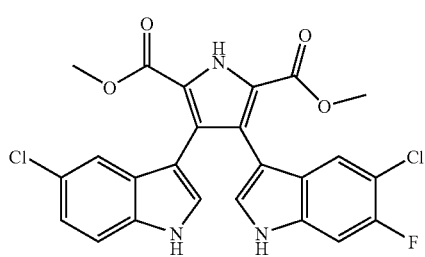

The compound of Formula XXII has a molecular formula of $C_{24}H_{16}Cl_2FN_3O_4$ and a molecular weight of 500.3055.

In another embodiment, the compound has the structure of Formula XXIII:

Formula XXIII

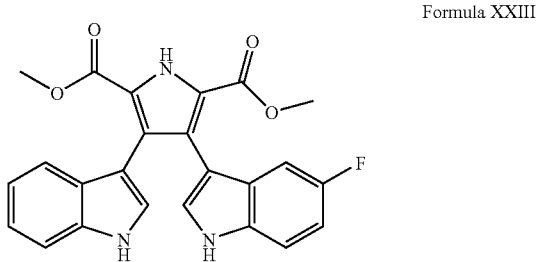

The compound of Formula XXIII has a molecular formula of $C_{24}H_{18}FN_3O_4$ and a molecular weight of 431.4159.

In another embodiment, the compound has the structure of Formula XXIV:

Formula XXIV

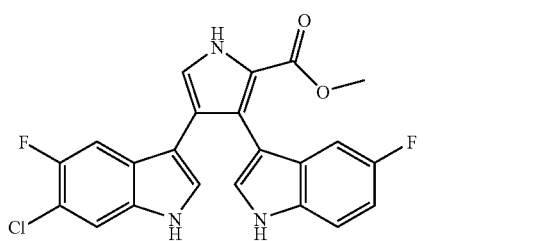

The compound of Formula XXIV has a molecular formula of $C_{22}H_{14}ClF_2N_3O_2$ and a molecular weight of 425.8151.

In another embodiment, the compound has the structure of Formula XXV:

Formula XXV

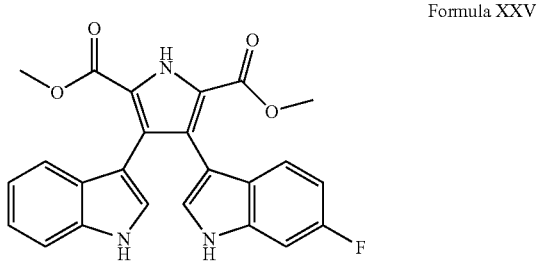

The compound of Formula XXV has a molecular formula of $C_{24}H_{18}FN_3O_4$ and a molecular weight of 431.4159.

In another embodiment, the compound has the structure of Formula XXVI:

Formula XXVI

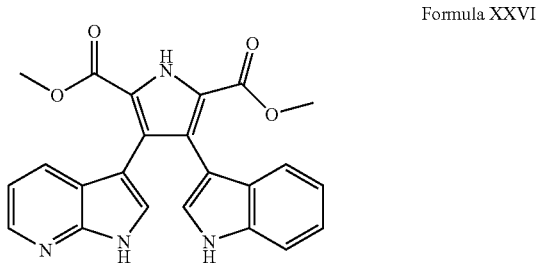

The compound of Formula XXVI has a molecular formula of $C_{23}H_{18}N_4O_4$ and a molecular weight of 414.4136.

In some embodiments, the compound has the structure of Formula XXVII or a corresponding salt:

Formula XXVII

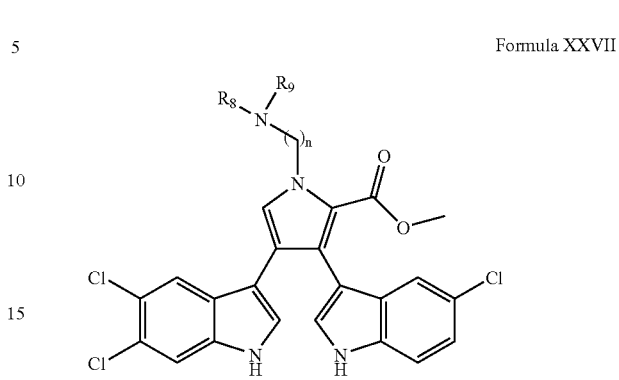

In some embodiments, $R_8$ and $R_9$ of Formula XXVII are, for example, ethyl, and n=2. For example, the compound can have the following structure of Formula XXVII-A:

Formula XXVII-A

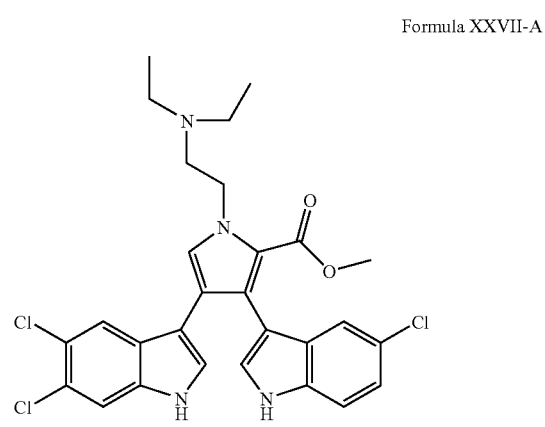

In some embodiments, $R_8$ and $R_9$ of Formula XXVII are, for example, ethyl, and n=3. For example, the compound can have the following structure of Formula XXVII-B:

Formula XXVII-B

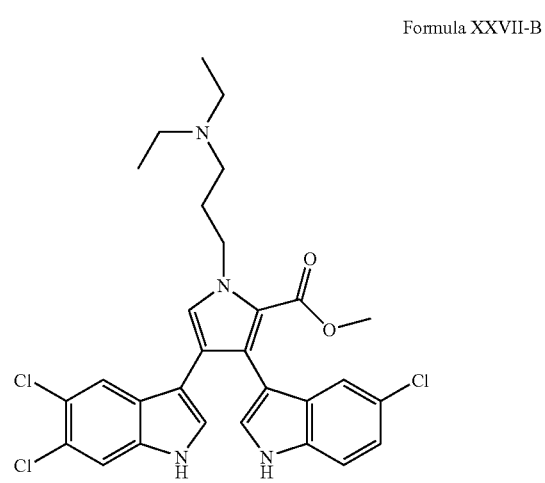

In some embodiments, $R_8$ and $R_9$ of Formula XXVII are, for example, $-(CH_2)_2-O-(CH_2)_2-$, can form a ring with the amine nitrogen, and n=2. For example, the compound can have the following structure of Formula XXVII-C:

Formula XXVII-C

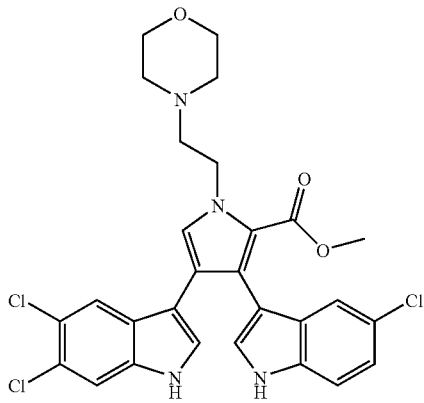

In some embodiments, the compound has the structure of Formula XXVIII or a corresponding salt:

Formula XXVIII

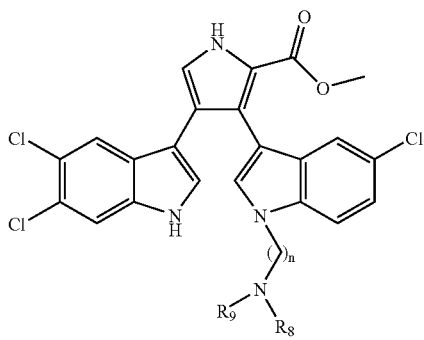

In some embodiments, $R_8$ and $R_9$ of Formula XXVIII are, for example, ethyl, and n=2. For example, the compound can have the following structure of Formula XXVIII-A:

Formula XXVIII-A

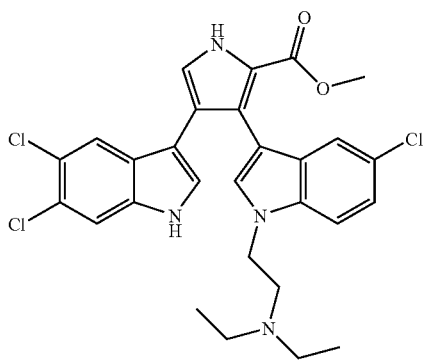

In some embodiment, the compound has the structure of Formula XXIX or a corresponding salt:

Formula XXIX

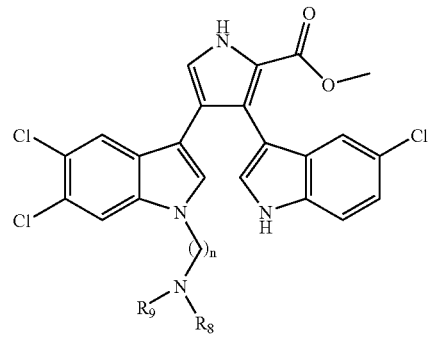

In some embodiments, $R_8$ and $R_9$ of Formula XXIX can be, for example, ethyl, and n=2. For example, the compound can have the following structure of Formula XXIX-A:

Formula XXIX-A

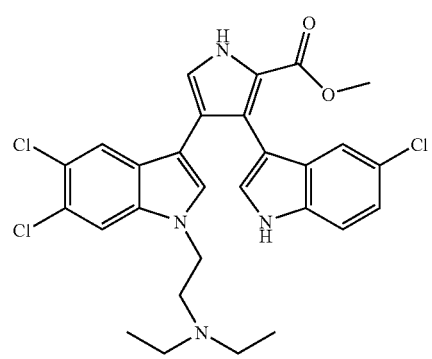

In another embodiment, the compound has the structure of Formula XXX:

Formula XXX

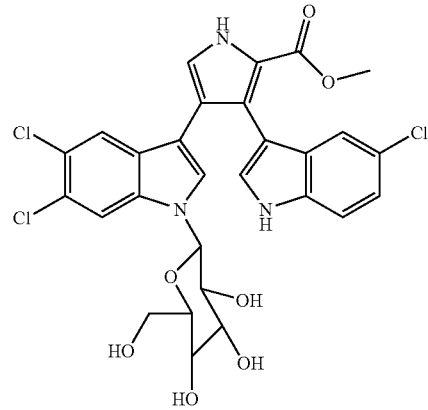

In another embodiment, the compound has the structure of Formula XXXI:

Formula XXXI

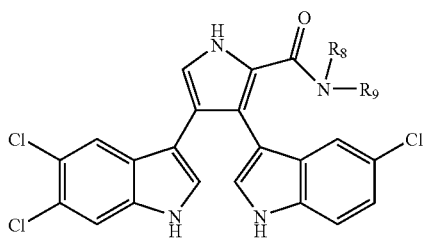

In some embodiments, $R_8$ and $R_9$ of Formula XXXI are, for example, ethyl and hydrogen, respectively. For example, the compound can have the following structure of Formula XXXI-A:

Formula XXXI-A

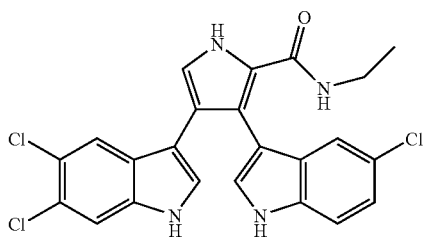

In some embodiments, $R_8$ and $R_9$ of Formula XXXI when taken together are, for example, $-(CH_2)_2-O-(CH_2)_2-$, and form a ring with the amide nitrogen. For example, the compound can have the following structure of Formula XXXI-B:

Formula XXXI-B

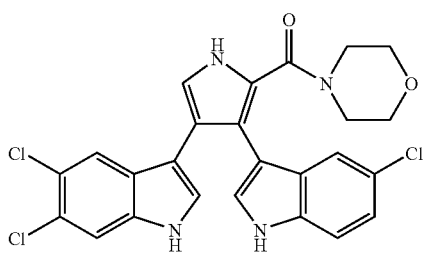

In another embodiment, the compound has the structure of Formula V:

Formula V

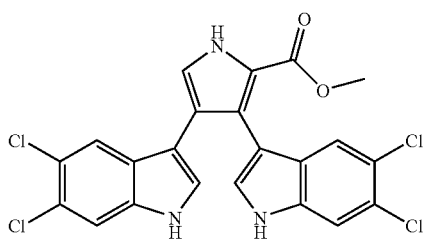

Certain embodiments also provide pharmaceutically acceptable salts and pro-drug esters of the compound of Formulae I, including the compounds of Formulae II–IV, VI–XXI, Formulae XXII–XXVI, Formulae XXVII–XXXI and Formula V, and provide methods of obtaining and purifying such compounds by the methods disclosed herein.

The term "pro-drug ester," especially when referring to a pro-drug ester of the compound of Formula I synthesized by the methods disclosed herein, refers to a chemical derivative of the compound that is rapidly transformed in vivo to yield the compound, for example, by hydrolysis in blood or inside tissues. The term "pro-drug ester" refers to derivatives of the compounds disclosed herein formed by the addition of any of several ester- or thioester-forming groups that are hydrolyzed under physiological conditions. Examples of pro-drug ester groups include pivoyloxymethyl, acetoxymethyl, phthalidyl, indanyl, and methoxymethyl, and thioester, as well as other such groups known in the art, including a (5-R-2-oxo-1,3-dioxolen-4-yl)methyl group. Other prodrugs can be prepared by preparing a corresponding thioester of the compound, for example, by reacting with an appropriate thiol, such as thiophenol, Cysteine or derivatives thereof, or propanethiol. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14–21 (1987) (providing examples of esters useful as pro-drugs for compounds containing carboxyl groups). Each of the above-mentioned references is hereby incorporated by reference in its entirety.

The term "pro-drug ester," as used herein, also refers to a chemical derivative of the compound that is rapidly transformed in vivo to yield the compound, for example, by hydrolysis in blood.

The term "pharmaceutically acceptable salt," as used herein, and particularly when referring to a pharmaceutically acceptable salt of a compound, including Formula (I), and Formula (I)as synthesized by the methods disclosed herein, refers to any pharmaceutically acceptable salts of a compound, and preferably refers to an acid addition salt of a compound. Preferred examples of pharmaceutically acceptable salt are the alkali metal salts (sodium or potassium), the alkaline earth metal salts (calcium or magnesium), or ammonium salts derived from ammonia or from pharmaceutically acceptable organic amines, for example $C_1$–$C_7$ alkylamine, cyclohexylamine, triethanolamine, ethylenediamine or tris-(hydroxymethyl)-aminomethane. With respect to compounds synthesized by the method of this embodiment that are basic amines, the preferred examples of pharmaceutically acceptable salts are acid addition salts of pharmaceutically acceptable inorganic or organic acids, for example, hydrohalic, sulfuric, phosphoric acid or aliphatic or aromatic carboxylic or sulfonic acid, for example acetic, succinic, lactic, malic, tartaric, citric, ascorbic, nicotinic, methanesulfonic, p-toluensulfonic or naphthalenesulfonic acid.

Preferred pharmaceutical compositions disclosed herein include pharmaceutically acceptable salts and pro-drug esters of the compound of Formula (I) obtained and purified by the methods disclosed herein. Accordingly, if the manufacture of pharmaceutical formulations involves intimate mixing of the pharmaceutical excipients and the active ingredient in its salt form, then it is preferred to use pharmaceutical excipients which are non-basic, that is, either acidic or neutral excipients.

It will be also appreciated that the phrase "compounds and compositions comprising the compound," or any like phrase, is meant to encompass compounds in any suitable form for pharmaceutical delivery, as discussed in further detail herein. For example, in certain embodiments, the compounds or compositions comprising the same can include a pharmaceutically acceptable salt of the compound. In one embodiment the compounds can be used to treat microbial diseases. Disease is meant to be construed broadly to cover infectious diseases, and also autoimmune diseases, non-infectious diseases and chronic conditions. In a preferred embodiment, the disease is caused by a microbe, such as a bacterium. The methods of use can also include the steps of administering a compound or composition comprising the compound to an individual with an infectious disease or cancer. The infectious disease can be, for example, one caused by *Bacillus*, such as *B. anthracis* and *B. cereus*, or one caused by gram-negative bacteria such as *E. coli*. It could also be one caused by *S. pneumoniae* or *S. pyogenes*, *H. influenzae*, *S. epidermidis* or *S. aureus*, *E. faecalis*, *E. faecium* and the like. The compound or composition can be administered with a pharmaceutically acceptable carrier, diluent, excipient, and the like.

The term "halogen atom," as used herein, means any one of the radio-stable atoms of column 7 of the Periodic Table of the Elements, i.e., fluorine, chlorine, bromine, or iodine, with fluorine and chlorine being preferred.

The term "alkyl," as used herein, means any unbranched or branched, substituted or unsubstituted, saturated hydrocarbon, with $C_1$–$C_6$ unbranched, saturated, unsubstituted hydrocarbons being preferred, with methyl, ethyl, isobutyl, and tert-butylpropyl, and pentyl being most preferred. Among the substituted, saturated hydrocarbons, $C_1$–$C_6$ mono- and di- and per-halogen substituted saturated hydrocarbons and amino-substituted hydrocarbons are preferred, with perfluromethyl, perchloromethyl, perfluoro-tert-butyl, and perchloro-tert-butyl being the most preferred.

The term "substituted" has its ordinary meaning, as found in numerous contemporary patents from the related art. See, for example, U.S. Pat. Nos. 6,509,331; 6,506,787; 6,500,825; 5,922,683; 5,886,210; 5,874,443; and 6,350,759; all of which are incorporated herein in their entireties by reference. Specifically, the definition of substituted is as broad as that provided in U.S. Pat. No. 6,509,331, which defines the term "substituted alkyl" such that it refers to an alkyl group, preferably of from 1 to 10 carbon atoms, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyacylamino, cyano, halogen, hydroxyl, carboxyl, carboxylalkyl, keto, thioketo, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl. The other above-listed patents also provide standard definitions for the term "substituted" that are well-understood by those of skill in the art.

The term "cycloalkyl" refers to any non-aromatic hydrocarbon ring, preferably having five to twelve atoms comprising the ring. The term "acyl" refers to alkyl or aryl groups derived from an oxoacid, with an acetyl group being preferred.

The term "alkenyl," as used herein, means any unbranched or branched, substituted or unsubstituted, unsaturated hydrocarbon including polyunsaturated hydrocarbons, with $C_1$–$C_6$ unbranched, mono-unsaturated and di-unsaturated, unsubstituted hydrocarbons being preferred, and mono-unsaturated, di-halogen substituted hydrocarbons being most preferred. In the $R_1$ and $R_4$ positions, of the compound of structure (I) a z-isoprenyl moiety is particularly preferred. The term "cycloalkenyl" refers to any non-aromatic hydrocarbon ring, preferably having five to twelve atoms comprising the ring.

The terms "aryl," "substituted aryl," "heteroaryl," and "substituted heteroaryl," as used herein, refer to aromatic hydrocarbon rings, preferably having five, six, or seven atoms, and most preferably having six atoms comprising the ring. "Heteroaryl" and "substituted heteroaryl," refer to aromatic hydrocarbon rings in which at least one heteroatom, e.g., oxygen, sulfur, or nitrogen atom, is in the ring along with at least one carbon atom. The substituted aryls and heteroaryls can be substituted with any substituent, including those described above and those known in the art.

The term "alkoxy" refers to any unbranched, or branched, substituted or unsubstituted, saturated or unsaturated ether, with $C_1$–$C_6$ unbranched, saturated, unsubstituted ethers being preferred, with methoxy being preferred, and also with dimethyl, diethyl, methyl-isobutyl, and methyl-tert-butyl ethers also being preferred. The term "cycloalkoxy" refers to any non-aromatic hydrocarbon ring, preferably having five to twelve atoms comprising the ring. The term "alkoxy carbonyl" refers to any linear, branched, cyclic, saturated, unsaturated, aliphatic or aromatic alkoxy attached to a carbonyl group. The examples include methoxycarbonyl group, ethoxycarbonyl group, propyloxycarbonyl group, isopropyloxycarbonyl group, butoxycarbonyl group, s-butoxycarbonyl group, t-butoxycarbonyl group, cyclopentyloxycarbonyl group, cyclohexyloxycarbonyl group, benzyloxycarbonyl group, allyloxycarbonyl group, phenyloxycarbonyl group, pyridyloxycarbonyl group, and the like.

The term "amide" refers to any compound with the structure "—$CONR_2$". The R groups (individually referred to as "$R_8$" and "$R_9$") can be the same or different. R groups can include a hydrogen atom, saturated $C_1$–$C_6$ alkyl, unsaturated $C_1$–$C_6$ alkenyl, cycloalkyl, cycloalkenyl, hydroxy, alkoxy, cycloalkoxy, aryl, substituted aryl, heteroaryl, substituted heteroaryl, phenyl, and substituted phenyl groups. In some embodiments, the "—$NR_2$" comprises a ring. For example, one R group can be —$(CH_2)_2$— and the other R group can be —$(CH_2)_2$— and the otherwise free ends of the two R groups can be linked together to form a five membered ring. Similarly, instead of the two R groups being directly linked to each other, they can be linked via group, for example, $R_{10}$, to form a 6-membered ring. $R_{10}$ can be selected from $CH_2$, NH, O and S. An example of this is shown in Formula XXXI-B.

The term "alkyl amine" or "aminoalkyl" refers to an alkyl group which is associated with an amine. Thus, aminoalkyls can be represented by the formula $(CH_2)_n NR_8 R_9$, where n can be any integer, for example, from 1 to 6. The R groups ($R_8$ and $R_9$) can be the same or different. R groups can include a hydrogen atom, saturated $C_1$–$C_6$ alkyl, unsaturated $C_1$–$C_6$ alkenyl, cycloalkyl, cycloalkenyl, hydroxy, alkoxy, cycloalkoxy, aryl, substituted aryl, heteroaryl, substituted heteroaryl, phenyl, and substituted phenyl groups. In some embodiments, as described above, the "—$NR_8 R_9$" comprises a ring. An example of this is shown in Formula XXVII-C.

The term carbohydrate is known in the art and includes various sugars. Examples include: glucomannan, xanthan gum, pectin, guar, agar, glycosaminoglycans, chitin, cellulose, glucose, starch, amylase, amylopectin, maltose, lactose, sucrose, trehalose, cellobiose, amino sugars, uronic acids, glucitol, glucosamine, glucuronic acid, D-Glucose, β-D-Glucose, α-D-Glucose, furanoses, pyranoses, D-Sedoheptulose, hexoses, D-tagatose, D-fructose, fructose, galactose, mannose, D-allose, D-altrose, D-glucose, D-mannose, D-gulose, D-idose, D-galactose, D-talose, pentoses, such as D-ribose, D-arabinose, D-xylose, and D-lyxose, and tetroses, such as, D-erythrose and D-threose. The term "sugars" refers to saccharides, such as mono, di, or tri saccharides. Several exemplary sugars are listed above under carbohydrates.

The term "asymmetrically substituted" refers to a point of symmetry running through the nitrogen group of the pyrrole and through the bond formed between carbon 3 and carbon 4 of the pyrrole group. The actual three dimensional structure of the compound is not considered in determining if the compound is symmetric. Thus, for example, a $R_6$ substitution would be asymmetrical if the substitution at position 5 of the pyrrole and position 2 of the pyrrole were not the same. As another example, a compound with different $R_3$ and $R_4$ substitutions at position 2 of both indole rings would also be asymmetric.

The phrase "wherein a ring can include one or more additional hetero-atoms," or similar such phrase, indicates a substitution in the atoms that comprise the ring structure itself. Thus, these can include substitutions of the atoms that create the indole rings or the pyrrole ring. Unless otherwise denoted, reference to a "ring" will denote the indole and/or the pyrrole ring.

The terms "pure," "purified," "substantially purified," and "isolated" as used herein refer to the compound of the embodiment being free of other, dissimilar compounds with which the compound, if found in its natural state, would be associated in its natural state. In certain embodiments described as "pure," "purified," "substantially purified," or "isolated" herein, the compound can comprise at least 0.5% to 1%, 1% to 5%, 5% to 10%, 10% to 20%, 20% to 50%, 50% to 70%, 70% to 90%, 90% to 95%, 95% to 99%, and 99% to 100%. In some embodiments, the amount of the compound will be at least 50% or 75% of the mass, by weight, of a given sample. In some embodiments, a final bis-indole pyrole product can be considered purified if there is more of the final bis-indole pyrole in a sample than there is of an initial bis-indole pyrole. Thus, if there is no initial bis-indole pyrole present in a sample, in this embodiment, any amount of a bis-indole pyrole will be sufficient. A "functional purity" is a measurement of the amount of a particular compound in a sample or product in relation to other compounds in a sample that can adversely impact the function of the compound. Thus, other components in a sample that do not interfere with the compound's activity (e.g., water), will not be used in determining the purity of a sample or product.

In some embodiments, the products created by the herein disclosed methods are contemplated. Thus, in some embodiments, it is not the presence of a molecule with a structure of a given formula that is important, but the disclosed process which results in the creation of a product with desired properties.

Unless explicitly noted, the phrases "compound of Formula #" and "compound #" are interchangeable.

The terms "derivative," "variant," or other similar term refers to a compound that is an analog of the other compound.

Certain of the compounds of Formula (I) can be obtained and purified or can be obtained via semi-synthesis from purified embodiments as set forth herein.

Producing Organisms

One microorganism which can be used for the production of bis-indole pyrroles is a strain isolated from a marine sediment sample collected at Mission Bay, Calif. The culture (strain NPS012745; Actinomycetes) was deposited on Jan. 7, 2004 with the American Type Culture Collection (ATCC) in 10801 University Blvd. Manassas, Va. 20110 and assigned the ATCC patent deposition number PTA-5748. The ATCC deposit meets all of the requirements of the Budapest treaty. The culture is also maintained at and available from Nereus Pharmaceutical Culture Collection at 10480 Wateridge Circle, San Diego, Calif. 92121. In addition to the specific microorganism described herein, it should be understood that mutants, such as those produced by the use of chemical or physical mutagens including X-rays, etc. and organisms whose genetic makeup has been modified by molecular biology techniques, can also be cultivated to produce bis-indole pyrroles compounds.

Fermentation of Strain NPS012745

The production of bis-indole pyrroles compounds of Formulae II, III, IV, VI, and XI can be carried out by cultivating strain NPS012745 in a suitable nutrient medium under conditions described herein, preferably under submerged aerobic conditions, until a substantial amount of compounds are detected in the fermentation; harvesting by extracting the active components from the fermentation broth with a suitable solvent; concentrating the solution containing the desired components; then subjecting the concentrated material to chromatographic separation to isolate the compounds from other metabolites also present in the cultivation medium.

Production of compounds can be achieved at temperature conducive to satisfactory growth of the producing organism, e.g. from 16 degrees C. to 40 degrees C., but it is preferable to conduct the fermentation at 22 degrees C. to 32 degrees C. The aqueous medium can be incubated for a period of time necessary to complete the production of compounds as monitored by high pressure liquid chromatography (HPLC), preferably for a period of about 2 to 10 days, on a rotary shaker operating at about 50 rpm to 300 rpm, preferably at 150 rpm to 250 rpm, for example.

Growth of the microorganisms can be achieved by one of ordinary skill of the art by the use of appropriate medium. Broadly, the sources of carbon include glucose, fructose, mannose, maltose, galactose, mannitol and glycerol, other sugars and sugar alcohols, starches and other carbohydrates, or carbohydrate derivatives such as dextran, cerelose, as well as complex nutrients such as oat flour, corn meal, millet, corn, and the like. The exact quantity of the carbon source that is utilized in the medium will depend in part, upon the other ingredients in the medium, but an amount of carbohydrate between 0.5 to 25 percent by weight of the medium can be satisfactorily used, for example. These carbon sources can be used individually or several such carbon sources can be combined in the same medium, for example. Certain carbon sources are preferred as hereinafter set forth.

The sources of nitrogen include amino acids such as glycine, arginine, threonine, methionine and the like, ammonium salt, as well as complex sources such as yeast extracts, corn steep liquors, distiller solubles, soybean meal, cottonseed meal, fish meal, peptone, and the like. The various sources of nitrogen can be used alone or in combination in amounts ranging from 0.5 to 25 percent by weight of the medium, for example.

Among the nutrient inorganic salts, which can be incorporated in the culture media, are the customary salts capable of yielding sodium, potassium, magnesium, calcium, phosphate, sulfate, chloride, carbonate, and like ions. Also included are trace metals such as cobalt, manganese, iron, molybdenum, zinc, cadmium, and the like.

The following is one exemplary fermentation protocol that can be utilized for preparing a 10 L batch of organisms that include bis-indole pyrroles of Formulae II, III, IV, VI, and XI:

1. Inoculate the starting culture or the freeze culture into 10 ml seed medium and incubate at 28 degrees C. and 250 rpm for 3 days.
2. Transfer ~5 ml of the above seed culture into 100-ml seed medium in a 500-ml flask. Incubate the flasks at 28 degrees C. and 250 rpm on a rotary shaker for 2 days.
3. Inoculate 5 ml each of the second seed culture into 10 500-ml flasks containing 100 ml seed medium. Incubate these flasks at 28 degrees C. and 250 rpm on a rotary shaker for 2 days.
4. Inoculate 5 ml each of the third seed culture into 100 500-ml flasks containing 100 ml production medium. Incubate these flasks at 28 degrees C. and 250 rpm on a rotary shaker for 7 days.
5. Shake the culture broth with 500 ml Acetone for 15 minutes and then extract with 10 L of EtOAc. The extract is dried in vacuo in preparation for isolation of bis-indole pyrroles.

The pure compounds of Formulae II, III, IV, VI, and XI can be obtained by HPLC chromatography as described below:

| | |
|---|---|
| Column: | ACE 5 C18-HL |
| Dimensions: | 15 cm × 21 mm ID |
| Flow rate: | 14.5 ml/min |
| Detection: | 290 nm |
| Solvent: | Gradient of 60% MeOH 40% H$_2$O to 100% MeOH (15 min) |

Fifty mg of the crude extract is dissolved in DMSO (900 µl) and this solution is injected on the HPLC column. This solution is injected using the HPLC chromatography conditions described above and the compounds of interest elute in the order shown in FIG. 1. The fractions containing the bis-indole-pyrroles can be further purified using an semi-preparative HPLC method described below:

| | |
|---|---|
| Column: | ACE 5 C18-HL |
| Dimensions: | 10 mm × 250 mm ID |
| Flow rate: | 3 ml/min |
| Detection: | UV DAD |
| Solvent: | Gradient of 60% MeOH 40% H$_2$O to 100% MeOH (20 min) Or Isocratic 65% MeOH 35% H2O containing 0.1% ammonium acetate. |

The partially purified bis-indole pyrrole natural products of Formulae II, III, IV, VI, and XI can be obtained as pure materials using the conditions described above.

Directed Biosynthesis

One embodiment provides novel antibiotic compounds, or pharmaceutically acceptable salts thereof, which are de-chlorinated; brominated; fluorinated; or azatryptophan analogs of Formula I compounds produced by directed biosynthesis with Formula I compounds producing organism, or mutant thereof. The fermentation process is accomplished under submerged aerobic conditions in an aqueous medium containing carbon and nitrogen nutrient for a sufficient time to produce, for example, the novel antibiotics of Formulae IX, XV, XV', XVI, XVII, XXII, XXV, XVIII, XIX, XIX', XX, XXI, XXI', XXIII, XXIV, XIII, XIV, XXVI, and other similar compounds.

Formation by Base Hydrolysis of Semisynthetic Derivatives

One embodiment provides novel antibiotic compounds, or pharmaceutically acceptable salts thereof, which are carboxylic acid derivatives of Formula I produced by base hydrolysis of Formula I, where one of the substituents is an ester. This process can produce, for example, compounds of Formulae VII, VIII, and XII, salts thereof, and other similar compounds.

Structural Determination

Figure 2A:
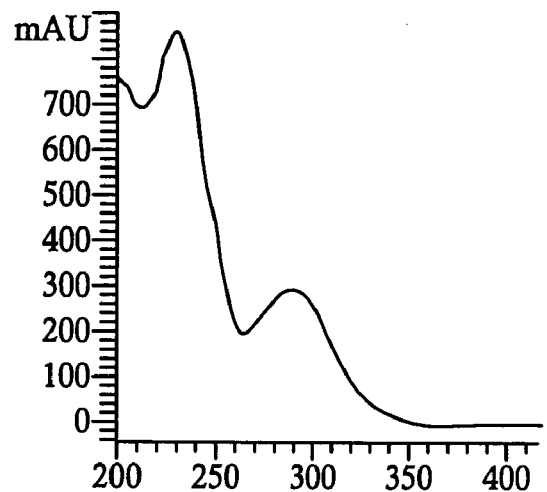
FIGS. 2A–E depict the UV spectrums of certain compounds of the invention. Spectra were obtained in acetonitrile/$H_2O$.
Figure 2B:
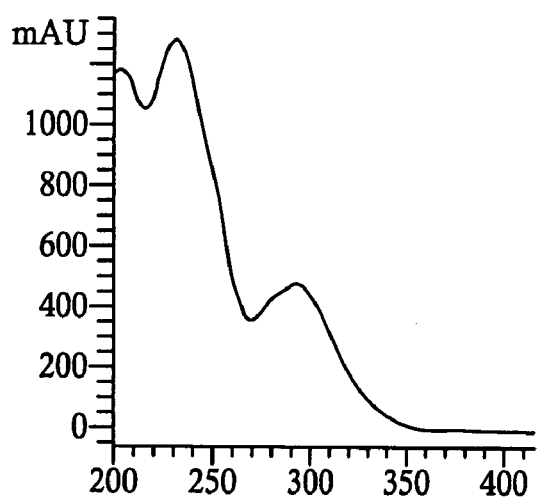
Figure 2C:
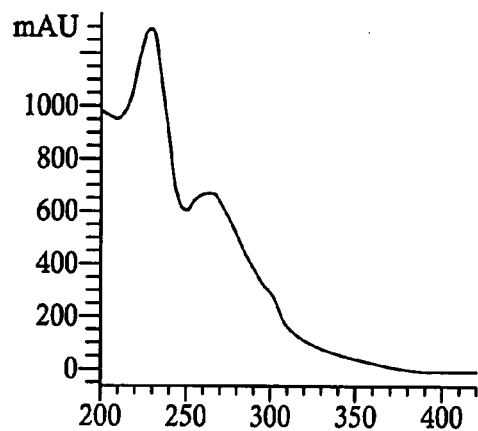
Figure 2D:
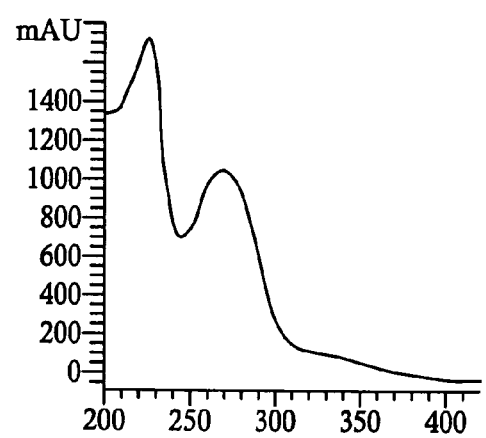
Figure 2E:
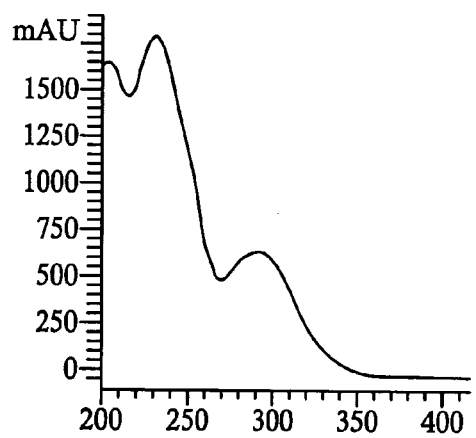

The structure of the purified or otherwise derived compounds can be elucidated by various methods, including NMR, MS, and UV. FIGS. 2A–E provides spectral data from these methods. FIG. 2 depicts the UV spectrum of the compounds in acetonitrile/H$_2$O. FIG. 2A depicts the UV spectrum of the compound of Formula III. FIG. 2B depicts the UV spectrum of the compound of Formula II. FIG. 2C depicts the UV spectrum of the compound of Formula VI. FIG. 2D depicts the UV spectrum of the compound of Formula IX. FIG. 2E depicts the UV spectrum of the compound of Formula XII.

Figure 3A:
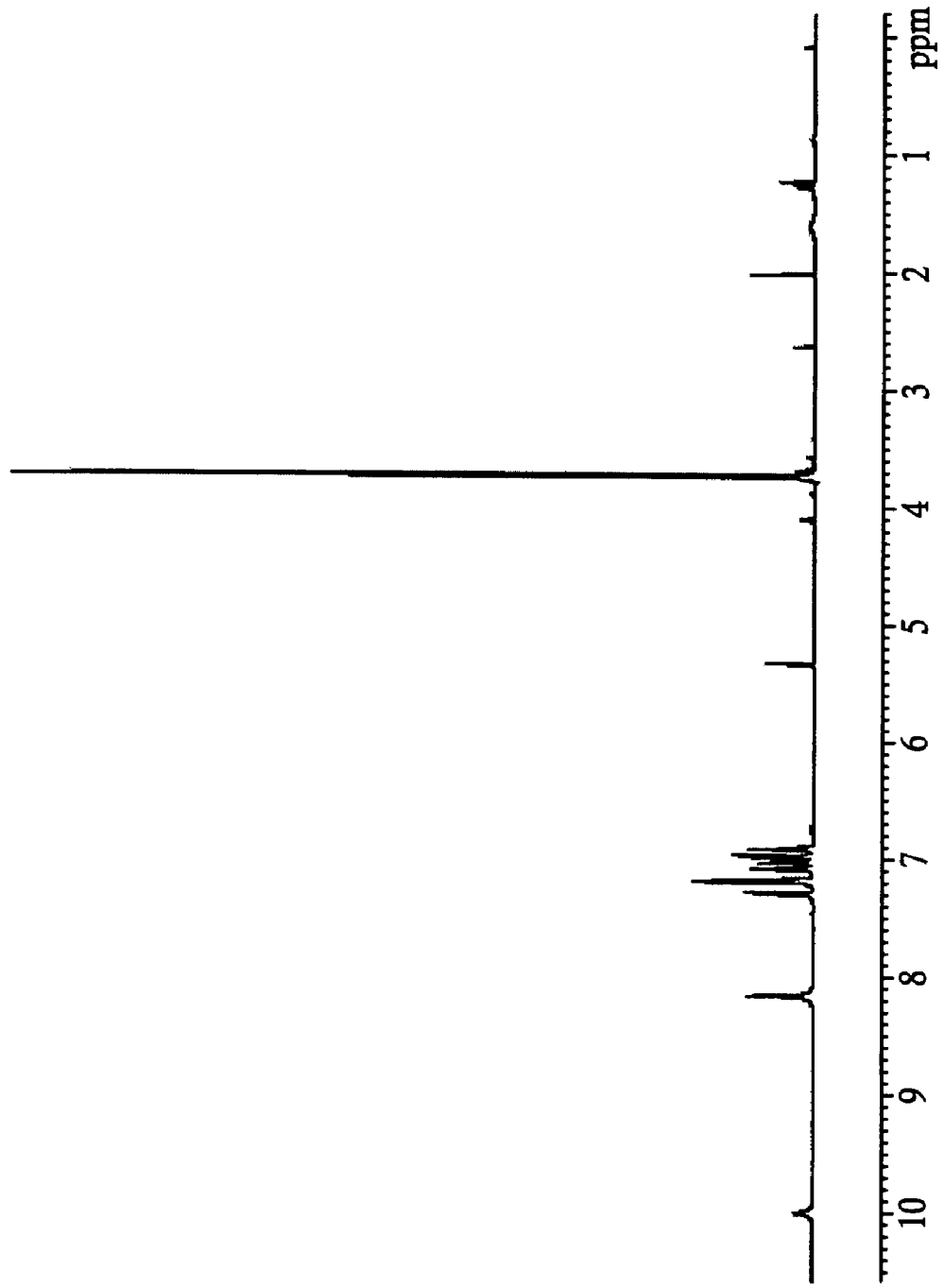
FIG. 3A depicts the $^1$H NMR spectrum of the compound of Formula XI.
Figure 3B:
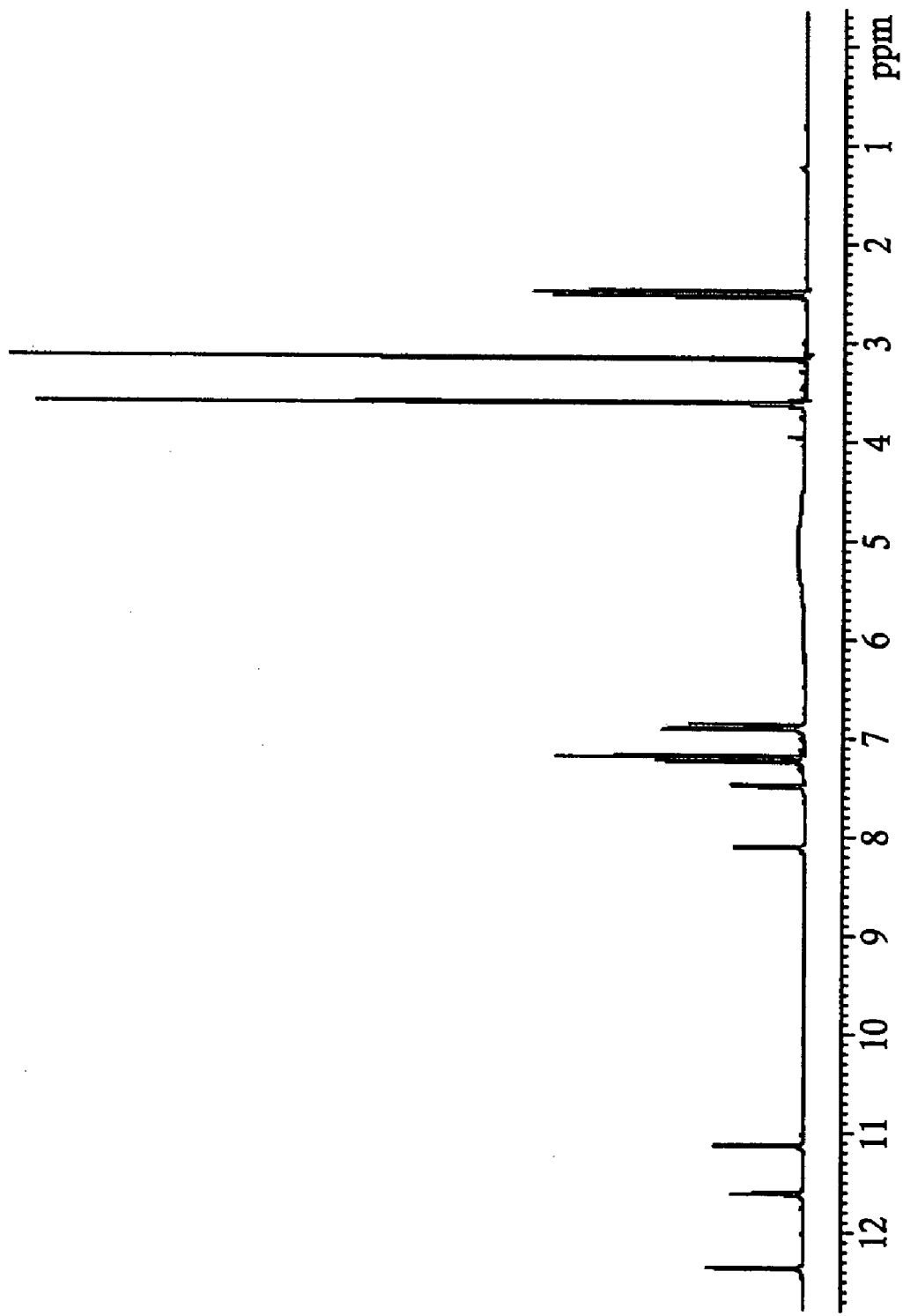
FIG. 3B depicts the $^1$H NMR spectrum of the compound of Formula XIII.
Figure 3C:
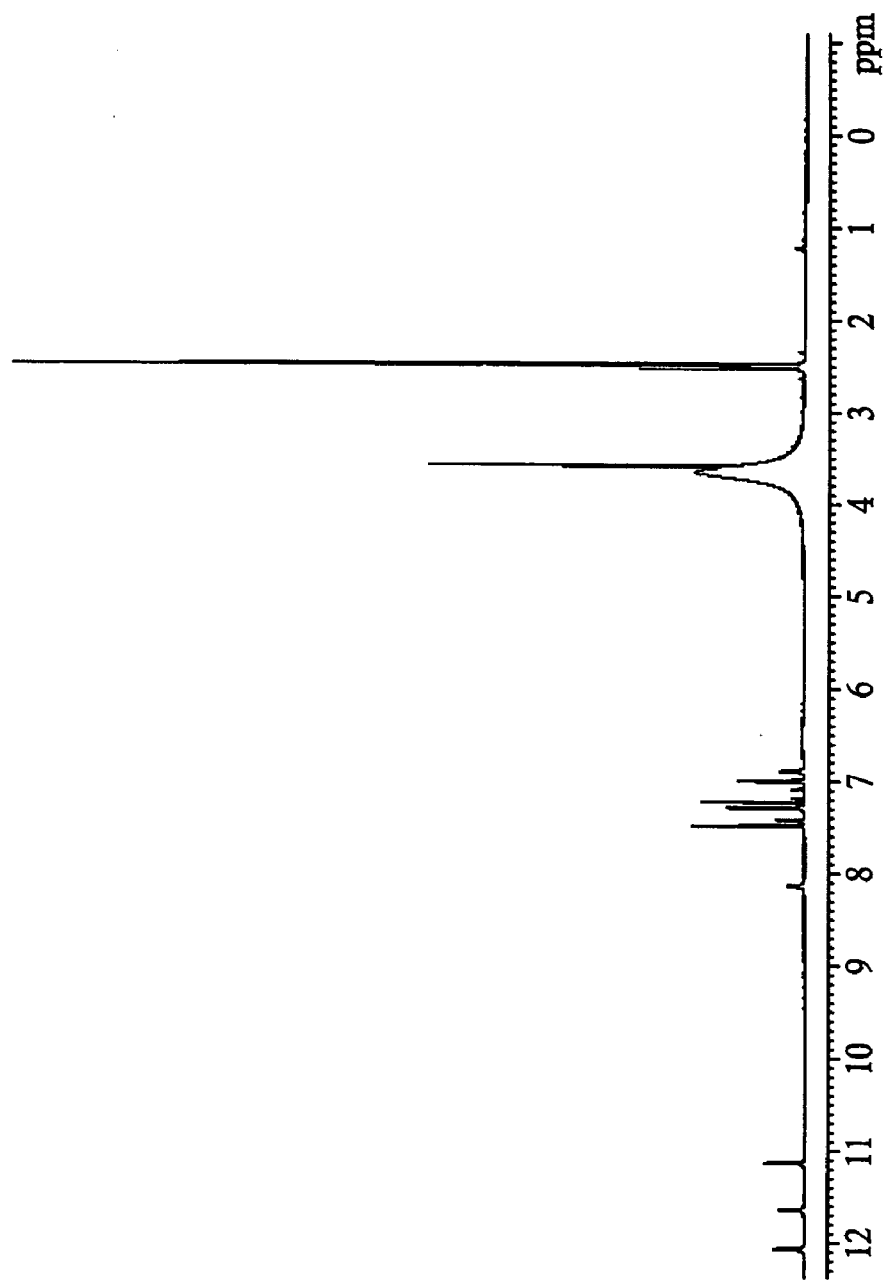
FIG. 3C depicts the $^1$H NMR spectrum of the compound of Formula XIV.
Figure 3D:
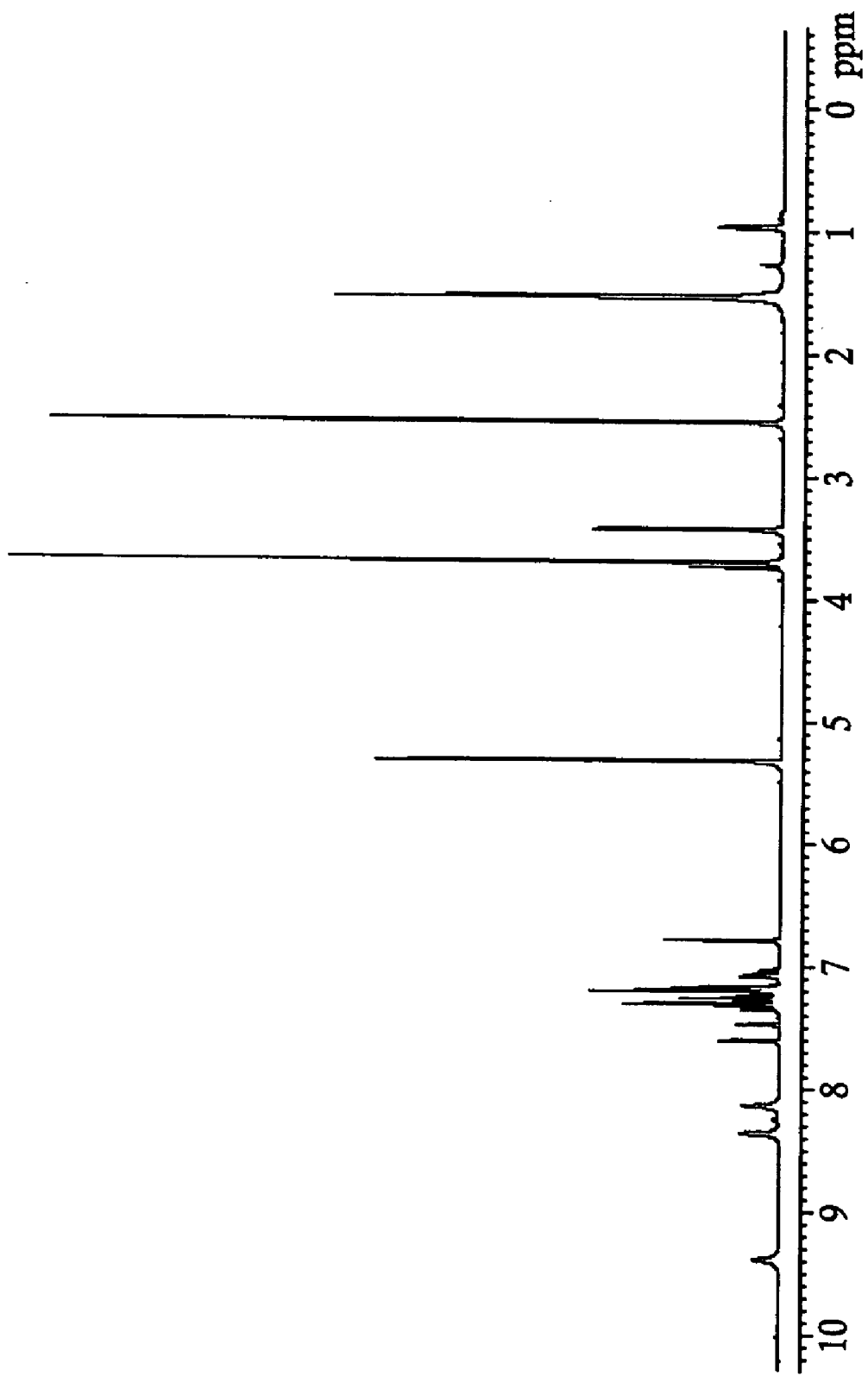
FIG. 3D depicts the $^1$H NMR spectrum of the compound of Formula XV'.
Figure 3E:
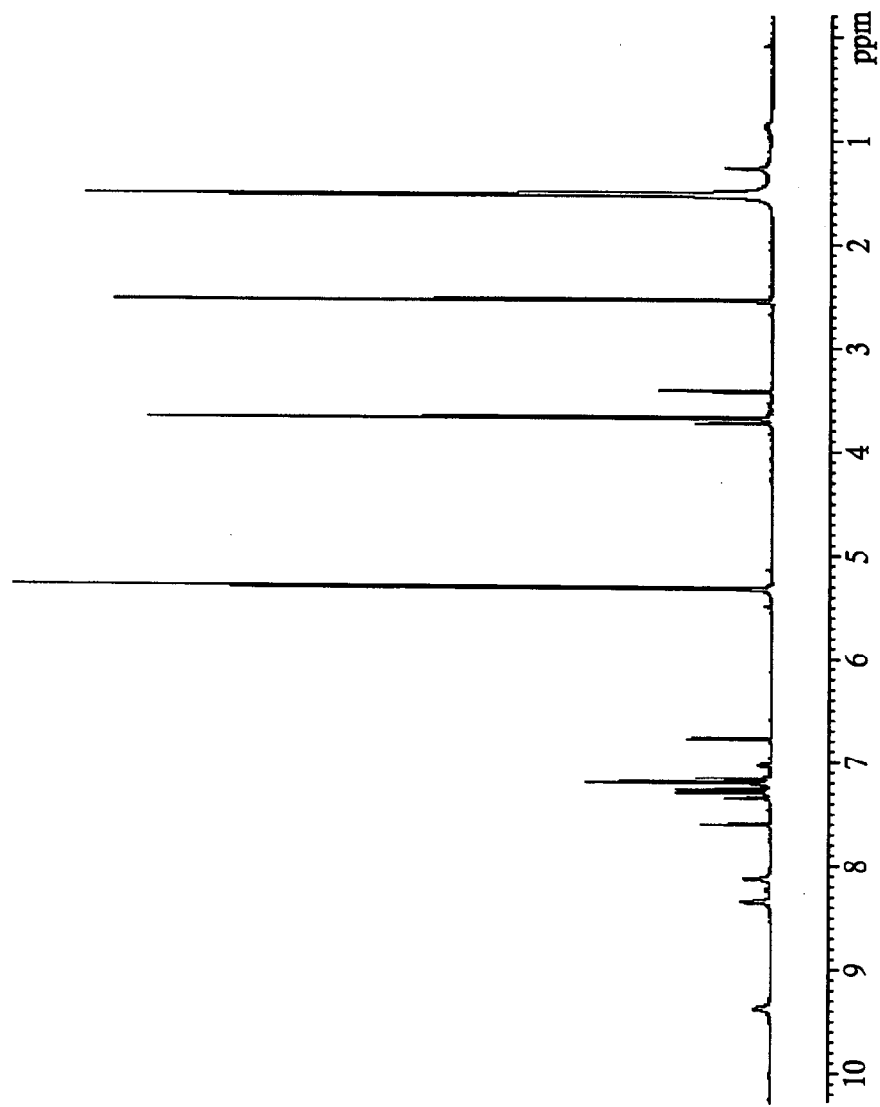
FIG. 3E depicts the $^1$H NMR spectrum of the compound of Formula XVI.
Figure 3F:
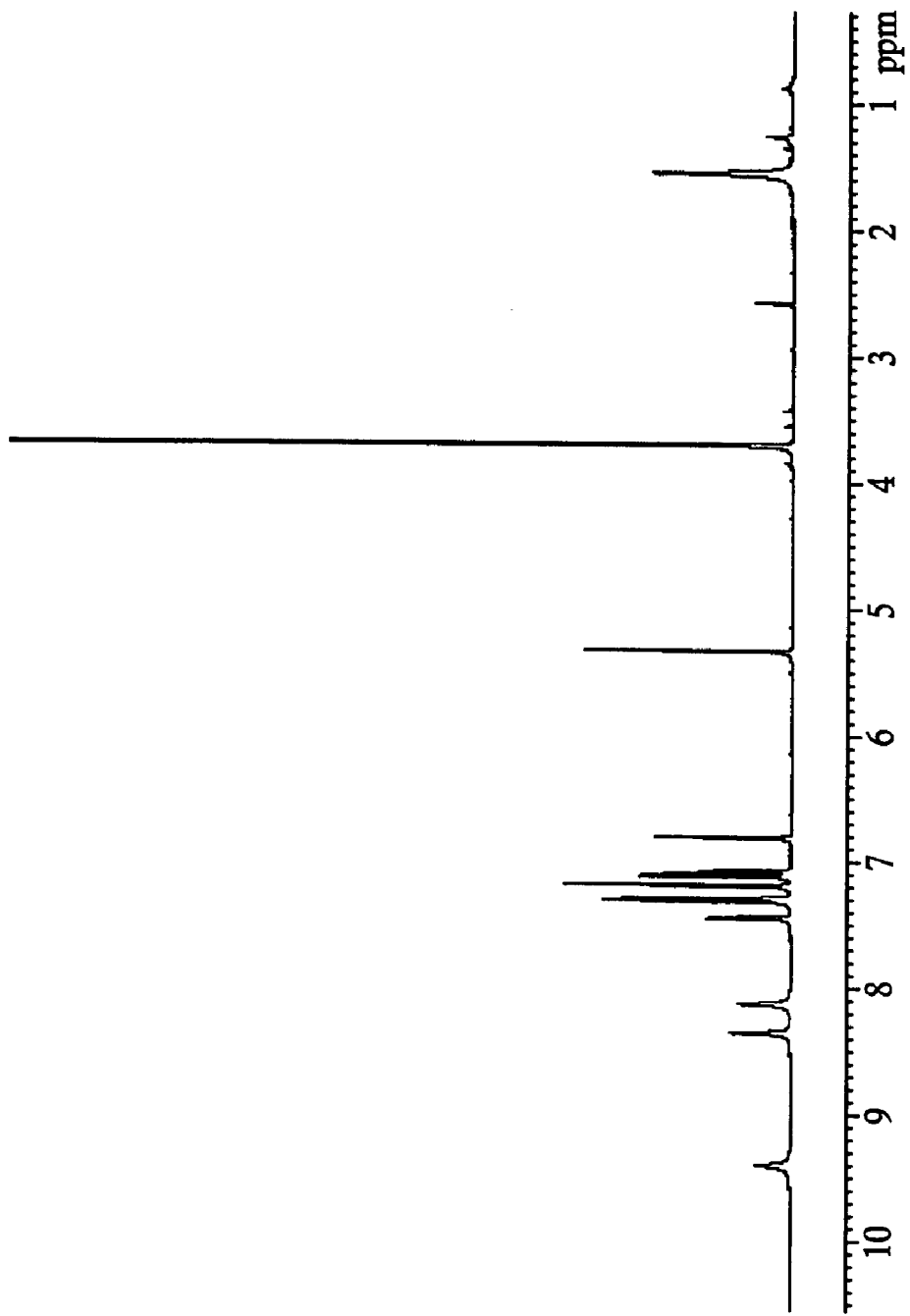
FIG. 3F depicts the $^1$H NMR spectrum of the compound of Formula XVII.
Figure 3G:
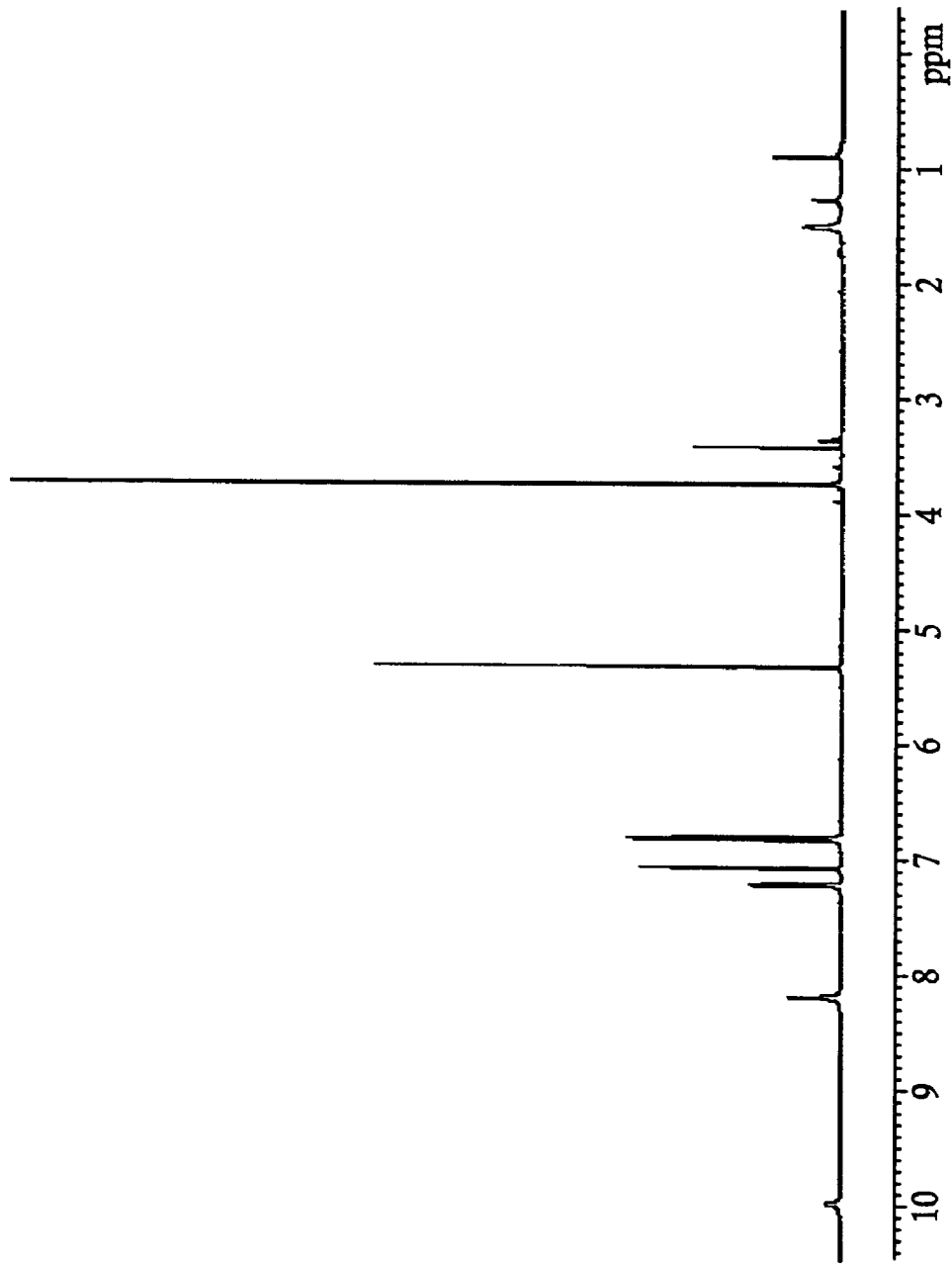
FIG. 3G depicts the $^1$H NMR spectrum of the compound of Formula XVIII.
Figure 3H:
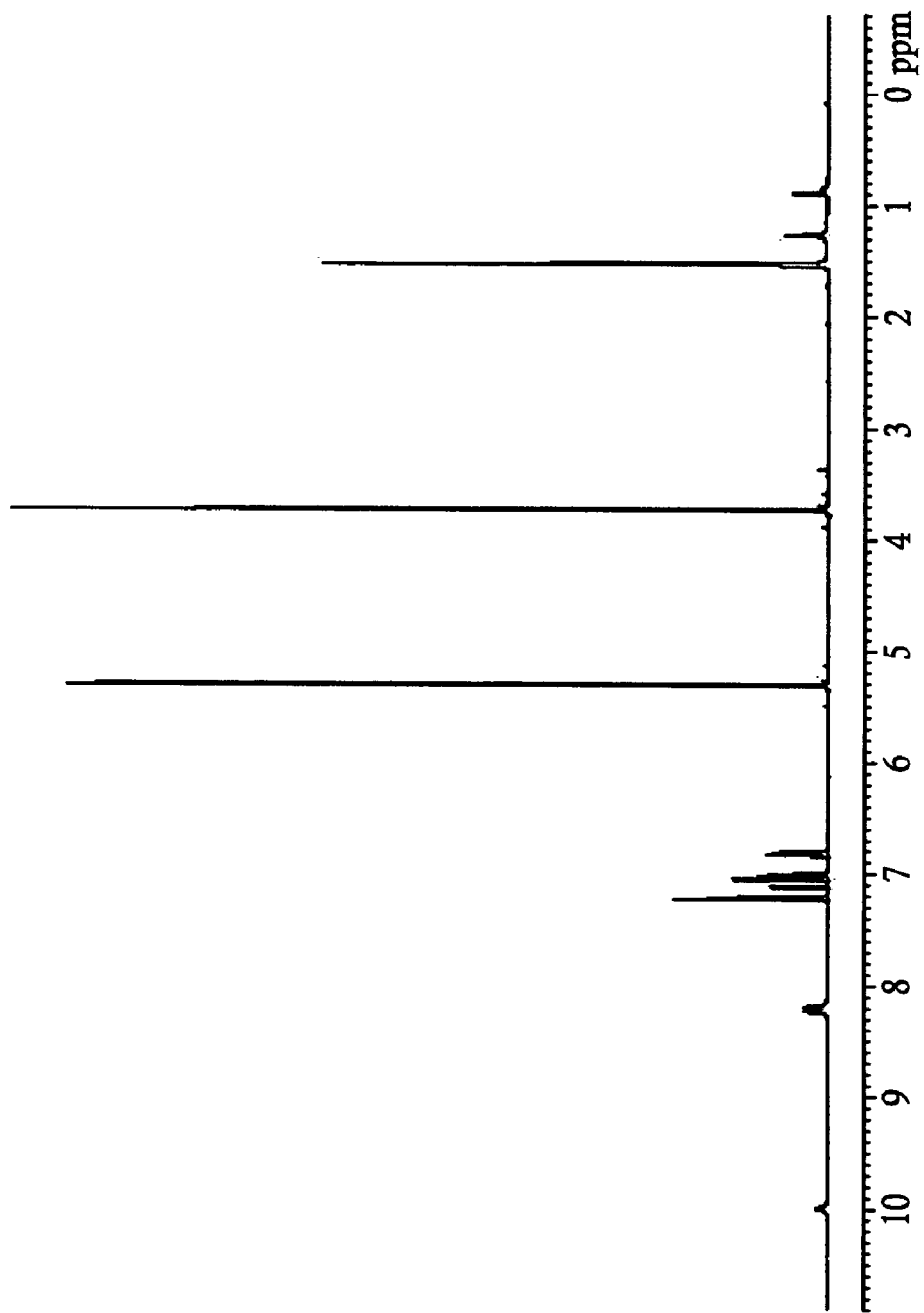
FIG. 3H depicts the $^1$H NMR spectrum of the compound of Formula XX.
Figure 3J:
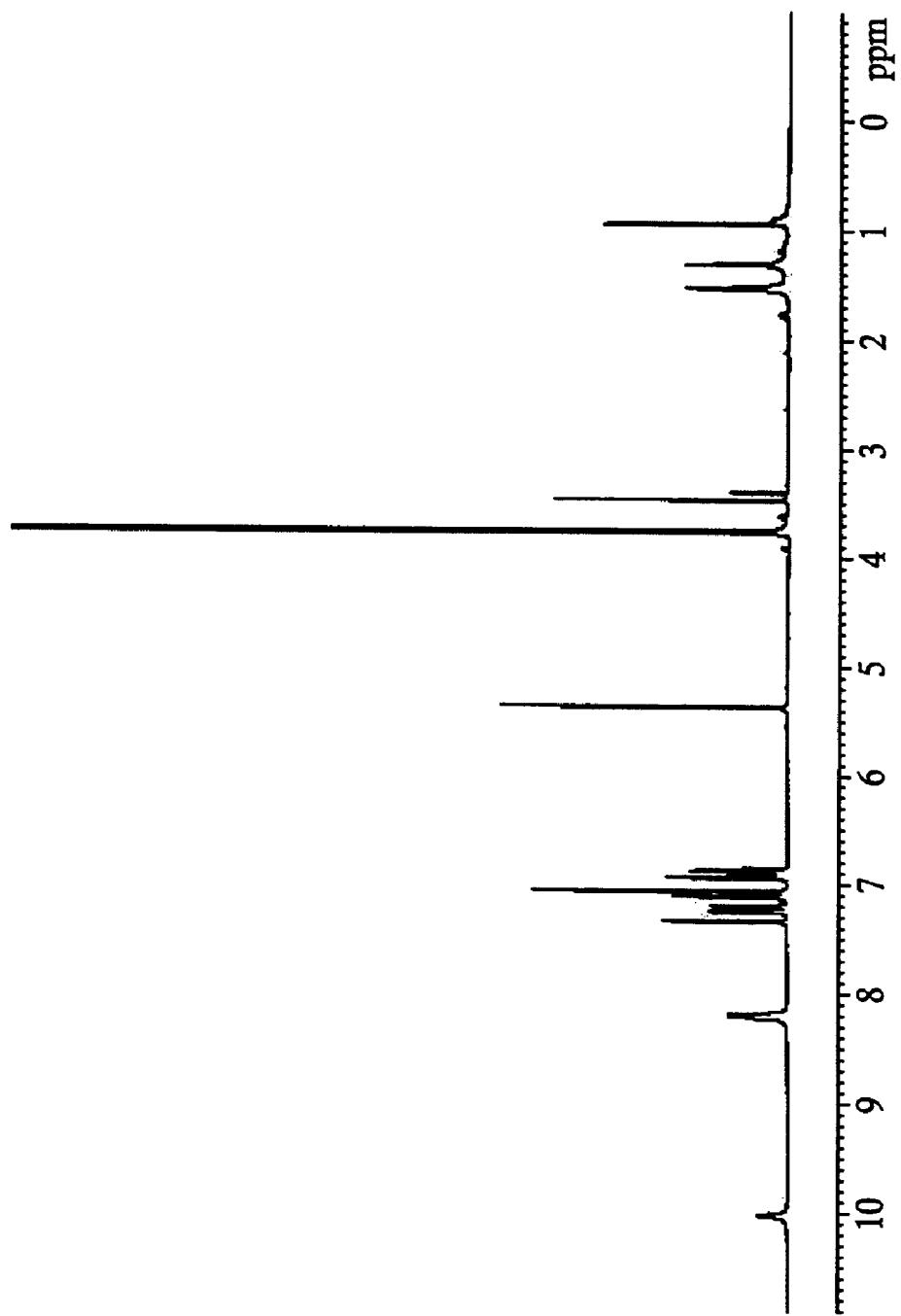
FIG. 3J depicts the $^1$H NMR spectrum of the compound of Formula XXIII.
Figure 3K:
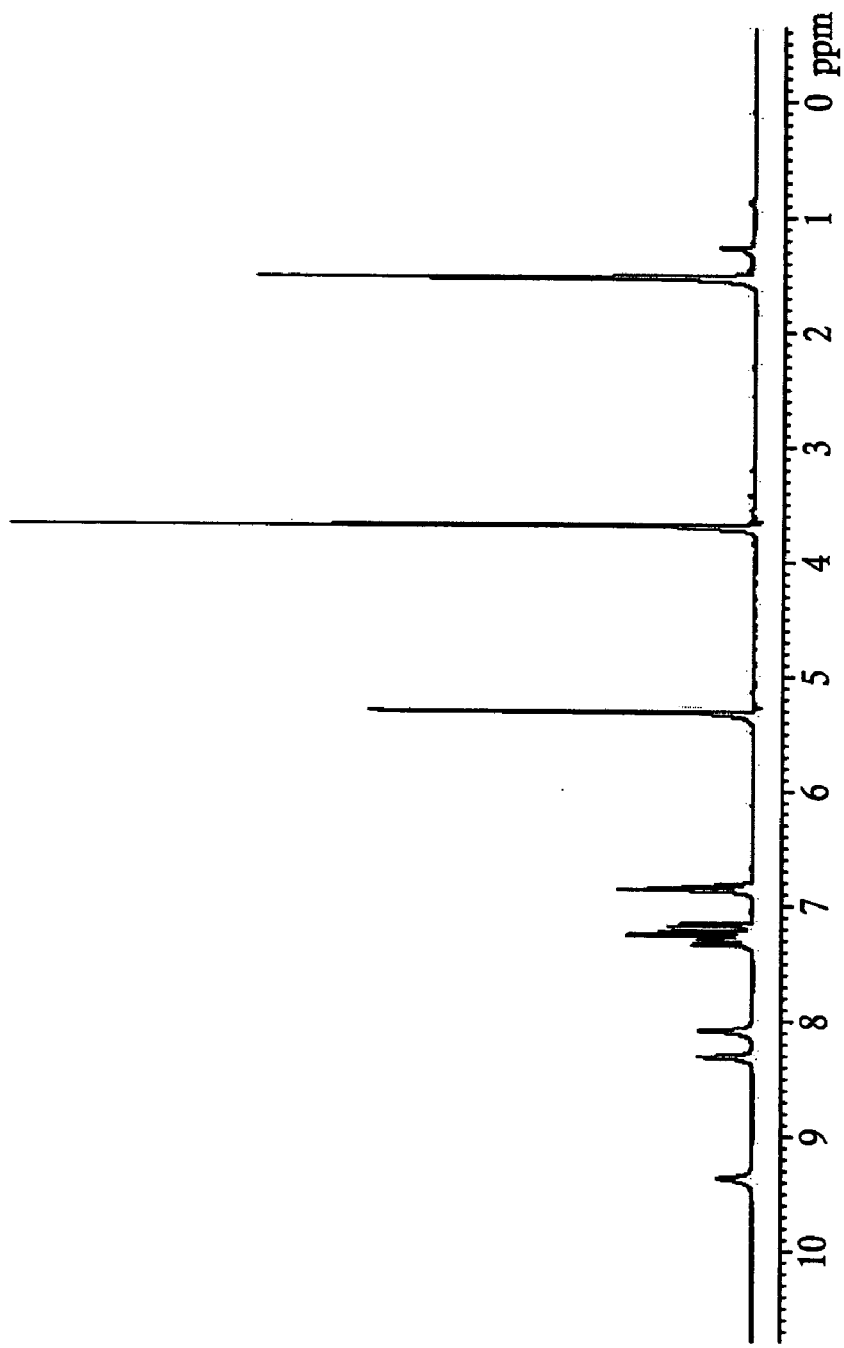
FIG. 3K depicts the $^1$H NMR spectrum of the compound of Formula XXIV.
Figure 3L:
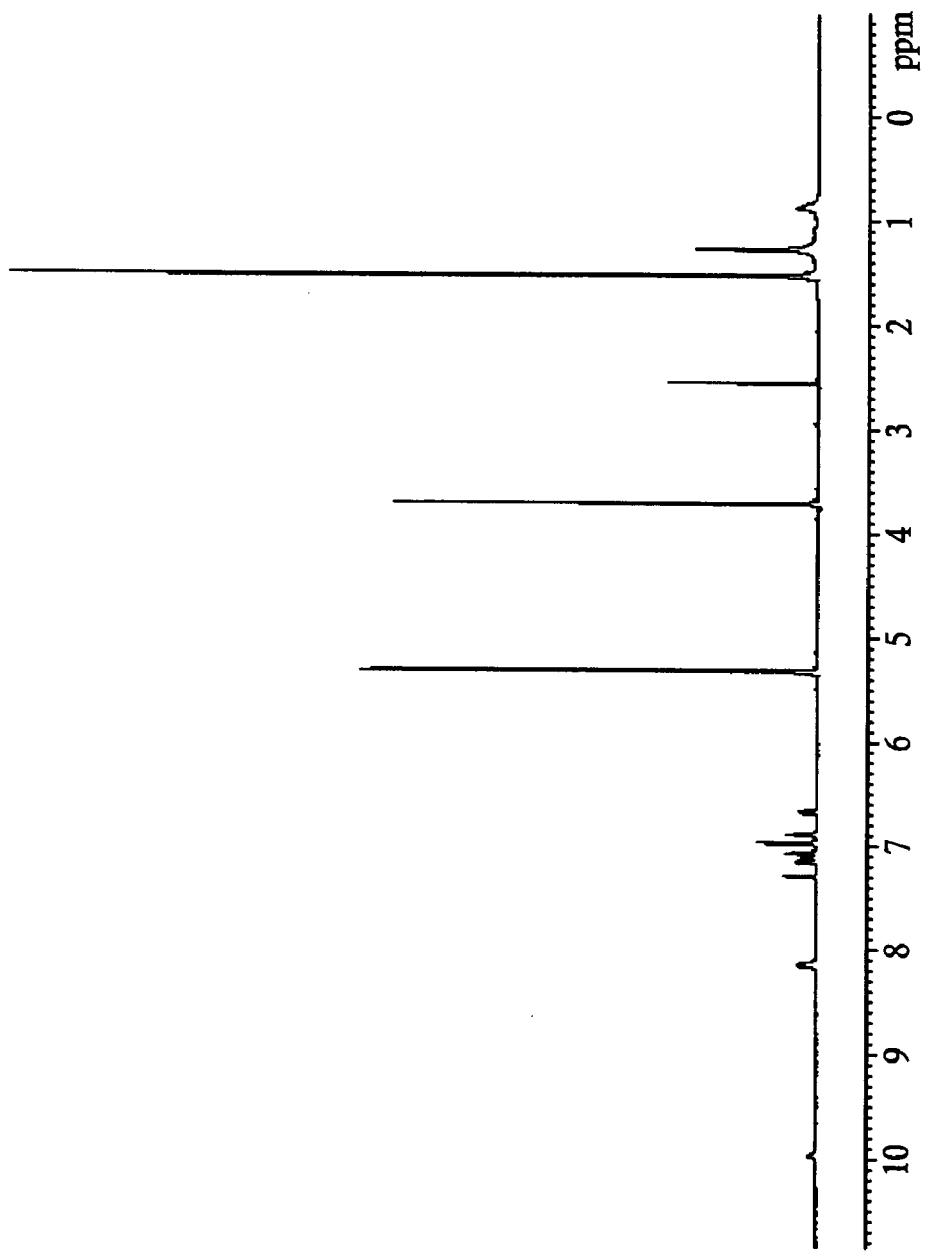
FIG. 3L depicts the $^1$H NMR spectrum of the compound of Formula XXV.
Figure 3M:
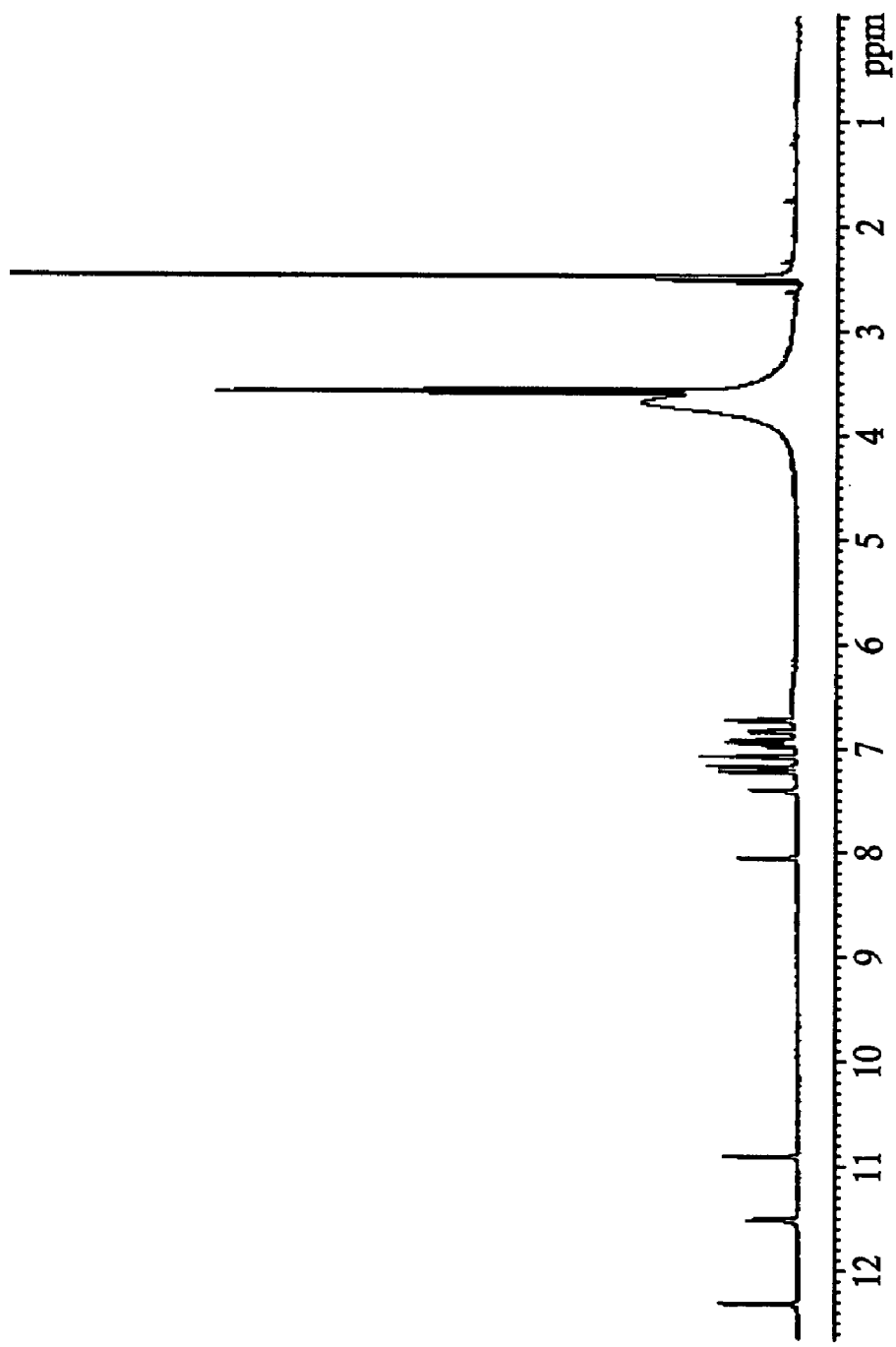
FIG. 3M depicts the $^1$H NMR spectrum of the compound of Formula XXVI.

The $^1$H NMR data for each of these compounds is depicted in Table 1. Additionally, FIG. 3 depicts the $^1$H NMR spectrum of several of the various compounds. FIG. 3A depicts the $^1$H NMR spectrum of the compound of Formula XI in CD$_2$CL$_2$. FIG. 3B depicts the $^1$H NMR spectrum of the compound of Formula XIII in DMSO-d$_6$. FIG. 3C depicts the $^1$H NMR spectrum of the compound of Formula XIV in DMSO-d$_6$. FIG. 3D depicts the $^1$H NMR spectrum of the compound of Formula XV' in CD$_2$Cl$_2$. FIG. 3E depicts the $^1$H NMR spectrum of the compound of Formula XVI in CD$_2$Cl$_2$. FIG. 3F depicts the $^1$H NMR spectrum of the compound of Formula XVII in CD$_2$Cl$_2$. FIG. 3G depicts the $^1$H NMR spectrum of the compound of Formula XVIII in CD$_2$Cl$_2$. FIG. 3H depicts the $^1$H NMR spectrum of the compound of Formula XX in CD$_2$Cl$_2$. FIG. 3I depicts the $^1$H NMR spectrum of the compound of Formula XXII in CD$_2$Cl$_2$. FIG. 3J depicts the $^1$H NMR spectrum of the compound of Formula XXIII in CD$_2$Cl$_2$. FIG. 3K depicts the $^1$H NMR spectrum of the compound of Formula XXIV in CD$_2$Cl$_2$. FIG. 3L depicts the $^1$H NMR spectrum of the compound of Formula XXV in CD$_2$Cl$_2$. FIG. 3M depicts the $^1$H NMR spectrum of the compound of Formula XXVI in DMSO-d$_6$.

The $^{13}$C NMR data for each of the compounds of Formulae II, III, IV, VI, and XII are in Table 2.

TABLE 1

$^1$H NMR Assignment

| Pos | *δ $^1$H$_{(ppm)}$ int., mult, J (Hz) Formula III | *δ $^1$H$_{(ppm)}$ int., mult, J (Hz) Formula II | *δ $^1$H$_{(ppm)}$ int., mult, J (Hz) Formula XII |
|---|---|---|---|
| 1 | NH 9.436 1H, br | 9.398 1H, br | 9.506 1H, br |
| 5 | 7.309 1H, d, 3.1 | 7.284 1H, d, 3.5 | 7.369 1H, d, 3.1 |
| 7 | 3.687 3H, s | 3.693 3H, s | |
| 1' | NH 8.363 1H, br | 8.348 1H, br | 8.435 1H, br |
| 2' | 7.183 1H, d, 2.5 | 7.171 1H, d, 2.5 | 7.244 1H, d, 2.5 |
| 4' | 7.192 1H, dd, 2.5, 0.6 | 7.187 1H, dd, 2.0, 0.5 | 7.230 1H, d, 1.9 |
| 6' | 7.069 1H, dd, 8.5, 2.5 | 7.070 1H, ddd, 8.5, 2.0, 0.5 | 7.109 1H, dd, 8.6, 2.0 |
| 7' | 7.312 1H, dd, 8.5, 0.6 | 7.306 1H, dd, 8.5, 05 | 7.335 1H, d, 8.6 |
| 1" | NH 8.130 1H, br | 8.121 1H, br | 8.114 1H, br |
| 2" | 6.791 1H, d, 2.5 | 6.830 1H, d, 2.5 | 6.806 1H, d, 2.5 |

TABLE 1-continued $^1$H NMR Assignment

| | | | |
|---|---|---|---|
| 4" | 7.472 1H, ddd, 1.9, 0.6, 0.6 | 7.510 1H, d, 0.6 | 7.539 1H, s |
| 6" | 7.077 1H, dd, 8.5, 2.5 | | |
| 7" | 7.251 1H, dd, 8.5, 0.6 | 7.426 1H, d, 0.6 | 7.432 1H, s |

| Pos | *δ $^1$H$_{(ppm)}$ int., mult, J (Hz) Formula IV | *δ $^1$H$_{(ppm)}$ int., mult, J (Hz) Formula VI | *δ $^1$H$_{(ppm)}$ int., mult, J (Hz) Formula IX |
|---|---|---|---|
| 1 | NH 8.539 1H, br | 10.011 1H, br | 9.979 1H, br |
| 5 | 7.082 2H, d, 3.0 | | |
| 7 | | 3.734 6H, s | 3.703, 6H, s |
| 1' | NH 8.180 2H, br | 8.243 2H, br | 8.145, 2H, br |
| 2' | 7.000 2H, d, 2.5 | 7.042 2H, d, 2.7 | 6.972, 2H, d, 2.0 |
| 4' | 7.567 2H, s | 7.149 2H, d, 1.8 | 7.198, 2H, d, 8.0 |
| 5' | | | 6.904, 2H, dd, 7.5 |
| 6' | | 7.028 2H, dd, 8.6, 2.0 | 7.072, 2H, dd, 7.5, 8.0 |
| 7' | 7.489, 2H, s | 7.239, 2H, d, 8.6 | 7.287, 2H, d, 8.0 |

*δ $^1$H values referenced to internal solvent for CD$_2$Cl$_2$ at 5.320 ppm

TABLE 2

$^{13}$C NMR Assignment Table

| Pos | Formula III δ $^{13}$C*$_{(ppm)}$ | Formula II δ $^{13}$C*$_{(ppm)}$ | Formula IV δ $^{13}$C*$_{(ppm)}$ | Formula XII δ $^{13}$C*$_{(ppm)}$ | Formula VI δ $^{13}$C*$_{(ppm)}$ |
|---|---|---|---|---|---|
| 2 | 120.897 | 120.973 | 117.682 | 119.475 | 124.48** |
| 3 | 121.573 | 121.597 | 115.691 | 121.443 | 122.96** |
| 4 | 120.314 | 119.869 | | 119.652 | |
| 5 | 120.997 | 120.949 | | 121.390 | |
| 6 | 161.437 | 161.343 | | 162.045 | 160.82 |
| 7 | 51.441 | 51.464 | | | 51.96 |
| 2' | 126.237 | 126.250 | 124.794 | 125.616 | 126.47 |
| 3' | 110.017 | 109.864 | 111.959 | 108.353 | 109.02 |
| 3a' | 129.153 | 129.052 | 127.474 | 128.125 | 129.05 |
| 4' | 120.052 | 119.996 | 121.585 | 119.055 | 119.86 |
| 5' | 125.399 | 125.454 | 125.761 | 125.159 | 125.49 |
| 6' | 122.186 | 122.257 | 123.794 | 122.021 | 122.19 |
| 7' | 112.465 | 112.504 | 112.880 | 111.958 | 112.39 |
| 7a' | 134.532 | 134.522 | 135.278 | 133.881 | 134.23 |
| 2" | 124.191 | 124.693 | | 123.860 | |
| 3" | 110.491 | 110.705 | | 109.576 | |
| 3a" | 128.235 | 126.954 | | 126.070 | |
| 4" | 119.438 | 121.139 | | 120.272 | |
| 5" | 125.631 | 125.719 | | 125.061 | |
| 6" | 122.390 | 123.848 | | 123.188 | |
| 7" | 112.480 | 112.840 | | 112.100 | |
| 7a" | 134.55 | 134.954 | | 134.154 | |

*δ $^{13}$C values referenced to internal solvent for CD$_2$Cl$_2$ at 53.800 ppm
**Signals can be interchanged due to lack of HMBC correlations for assignment.

Furthermore, using UV spectrometry and mass spectrometry structural assignments can be elucidated for different embodiments of the relevant compounds. The following section includes examples of structures from such data and the relevant data for several different bis-indole pyrrole compounds.

For the compound of Formula II:

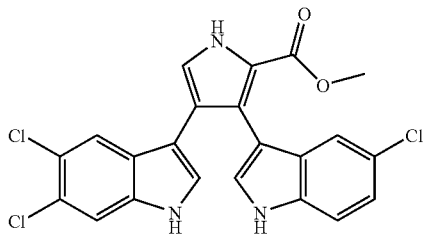

Formula II

UV spectrometry (Acetonitrile/H$_2$O) $\lambda_{max}$=231, 292 nm.
Mass spectrometry: HRESI MS M+Na=480.0059 $\Delta_{calc}$ C$_{22}$H$_{14}$N$_3$O$_2$Cl$_3$Na (480.0049)=1.9 ppm For the compound of Formula III:

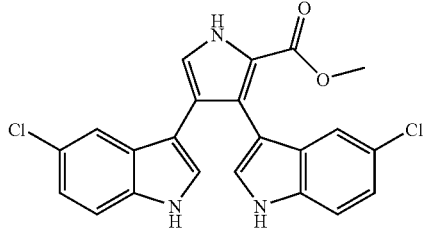

Formula III

UV spectrometry (Acetonitrile/H$_2$O): $\lambda_{max}$=230, 290 nm
Mass spectrometry: HRESI MS M+H=424.0612 $\alpha_{calc}$ C$_{22}$H$_{16}$N$_3$O$_2$Cl$_2$ (424.0620)=0.7 ppm For the a compound of Formula IV:

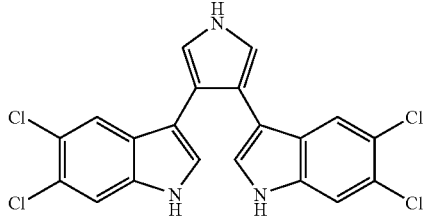

Formula IV

UV spectrometry (Acetonitrile/H$_2$O) $\lambda_{max}$=239, 299.

Mass spectrometry: HRESI MS M+H=433.9771 $\alpha_{calc}$ C$_{20}$H$_{12}$N$_3$Cl$_4$ (433.9785)=3.4 ppm For the compound of Formula VI:

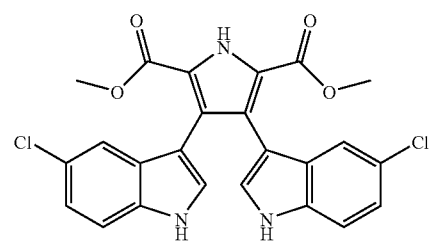

Formula VI

UV spectrometry (Acetonitrile/H$_2$O) $\lambda_{max}$=229, 262, sh 300

Mass spectrometry: HRESI MS M+H=482.0657 $\Delta_{calc}$ C$_{24}$H$_{18}$N$_3$O$_4$Cl$_2$ (482.0674)=3.7 ppm For the compound of Formula VII:

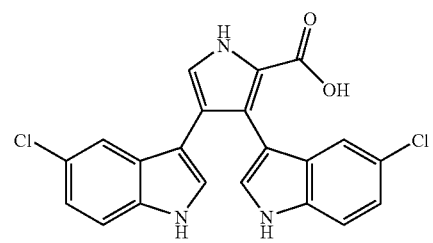

Formula VII

UV spectrometry (Acetonitrile/H$_2$O) $\lambda_{max}$=230, 290

Mass spectrometry: HRESI MS M+H=410.0453 $\Delta_{calc}$ C$_{21}$H$_{14}$N$_3$O$_2$Cl$_2$ (410.0463)=−2.4 ppm For the compound of Formula VIII:

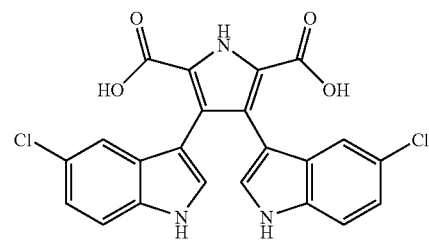

Formula VIII

UV spectrometry (Acetonitrile/H$_2$O) $\lambda_{max}$=230, 265, sh 300

Mass spectrometry: HRESI MS M+H=454.0355 $\Delta_{calc}$ $C_{22}H_{14}N_3O_4Cl_2$ (454.0361)=−1.5 ppm For the compound of Formula IX:

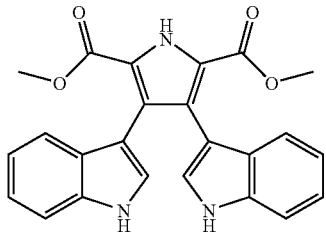

Formula IX

UV spectrometry (Acetonitrile/$H_2O$) $\lambda_{max}$=225, 269, sh 321.

Mass spectrometry: HRESI MS M+H=414.1449 $\Delta_{calc}$ $C_{24}H_{20}N_3O_4$ (414.1454)=1.2 ppm For the compound of Formula XI:

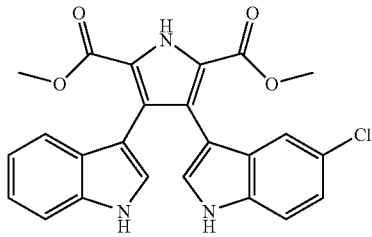

Formula XI

UV (Acetonitrile/$H_2O$, 0.05% formic acid) $\lambda_{max}$=224, 266 nm. HRESI MS M+H=448.1068 $\Delta_{calc}$ $C_{24}H_{19}N_3O_4Cl$ (448.1064)=0.7 ppm For the compound of Formula XII:

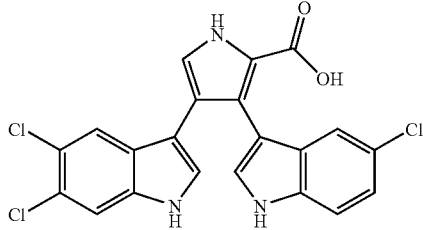

Formula XII

UV spectrometry (Acetonitrile/$H_2O$) $\lambda_{max}$=231, 291.
Mass spectrometry: HRESI MS M+H=444.0085 $\Delta_{calc}$ $C_{21}H_{13}N_3O_2Cl_3$ (444.0073)=2.7 ppm For the compound of Formula XIII:

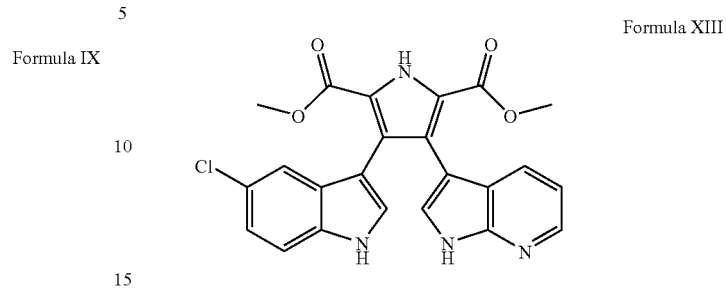

Formula XIII

UV spectrometry (Acetonitrile/$H_2O$) $\lambda_{max}$=230, 292 sh 245

Mass spectrometry: HRESI MS M+H=449.1018 $\Delta_{calc}$ $C_{23}H_{18}N_4O_4Cl$ (449.1017)=0.3 ppm For the compound of Formula XIV:

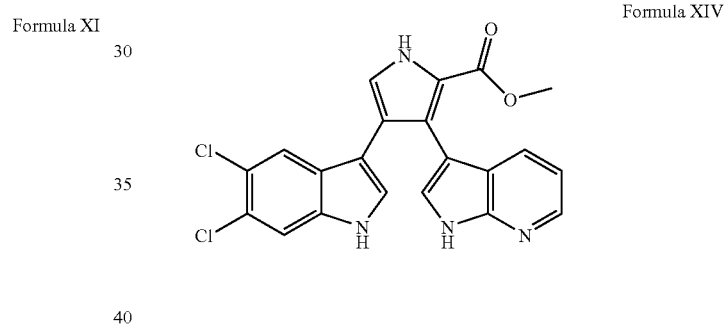

Formula XIV

UV spectrometry (Acetonitrile/$H_2O$) $\lambda_{max}$=229, 290
Mass spectrometry: HRESI MS M+H=425.0567 $\Delta_{calc}$ $C_{21}H_{15}N_4O_2Cl_2$ (425.2670)=1.2 ppm For the compound of Formula XV':

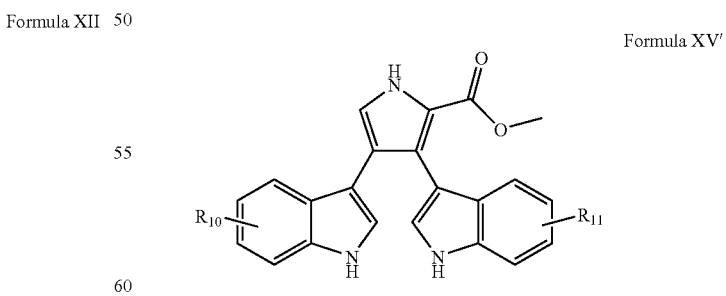

Formula XV'

UV spectrometry (Acetonitrile/$H_2O$) $\lambda_{max}$=231, 292.
Mass spectrometry: HRESI MS M+H=468.0132 $\Delta_{calc}$ $C_{22}H_{16}N_3O_2ClBr$ (468.0114)=3.8 ppm In Formula XV', $R_{10}$ can be a single bromine or a single chloride while $R_{11}$ will be the other of either the bromine or the chloride. For example, in one embodiment, Formula XV' is that shown in Formula XV:

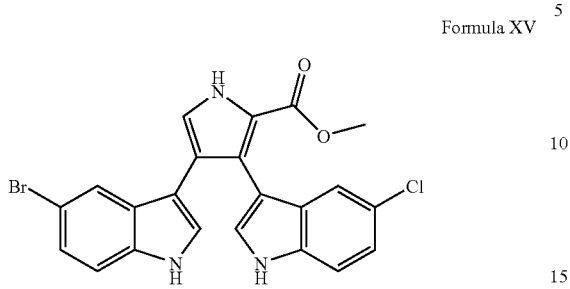

Formula XV

For the compound of Formula XVI:

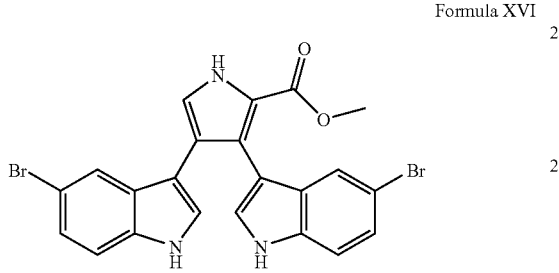

Formula XVI

UV spectrometry (Acetonitrile/$H_2O$) $\lambda_{max}$=230, 290.
Mass spectrometry: HRESI MS M+H=511.9616 $\Delta_{calc}$ $C_{22}H_{16}N_3O_2Br_2$ (511.9609)=1.4 ppm For the compound of Formula XVII:

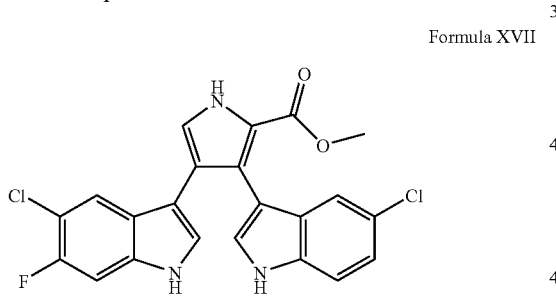

Formula XVII

UV spectrometry (Acetonitrile/$H_2O$) $\lambda_{max}$=231, 291.
Mass spectrometry: HRESI MS M+H=442.0541 $\Delta_{calc}$ $C_{22}H_{15}N_3O_2FCl_2$ (442.0525)=3.5 ppm For the compound of Formula XVIII:

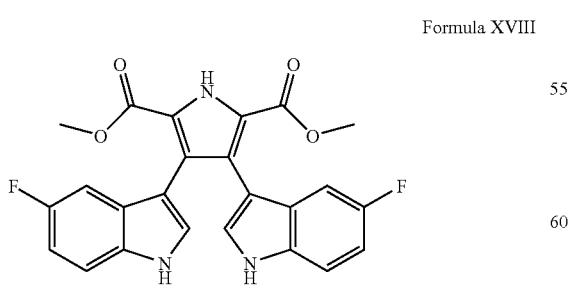

Formula XVIII

UV spectrometry (Acetonitrile/$H_2O$) $\lambda_{max}$=224, 268, sh 338.
Mass spectrometry: HRESI MS M+H=450.1279 $\Delta_{calc}$ $C_{24}H_{18}N_3O_4F_2$ (450.1265)=3.1 ppm For the compound of Formula XIX':

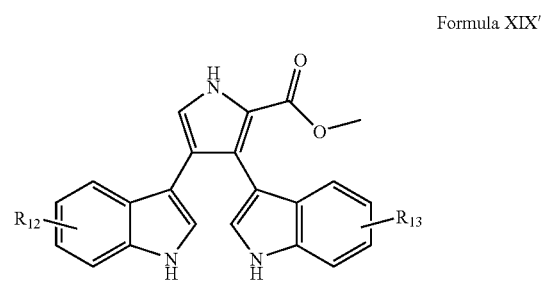

Formula XIX'

UV spectrometry (Acetonitrile/$H_2O$) $\lambda_{max}$=230, 291
Mass spectrometry: HRESI MS M+H=408.0907 $\Delta_{calc}$ $C_{22}H_{16}N_3O_2ClF$ (408.0915)=2.1 ppm In Formula XIX', $R_{12}$ can be a single fluorine, a single chloride, both, or none, while $R_{13}$ will correspondingly be a chloride, a fluorine, chloride, none, or both. For example, in one embodiment, Formula XIX' is that shown in Formula XIX:

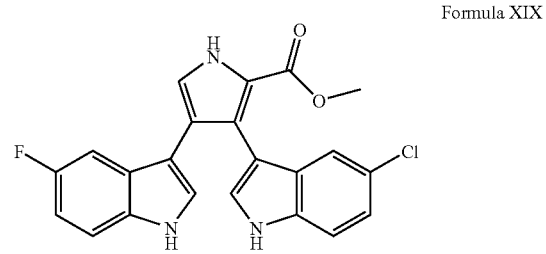

Formula XIX

For the compound of Formula XX:

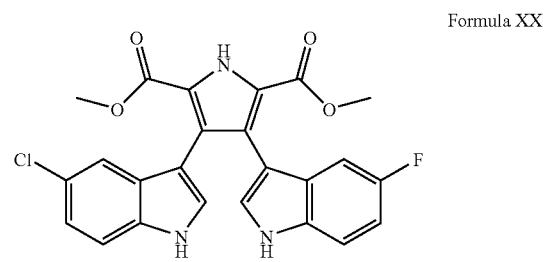

Formula XX

UV spectrometry (Acetonitrile/$H_2O$) $\lambda_{max}$=228, 268, sh 340.
Mass spectrometry: HRESI MS M+H=466.0966 $\Delta_{calc}$ $C_{24}H_{18}N_3O_4ClF$ (466.0970)=0.9 ppm For the compound of Formula XXI':

Formula XXI'

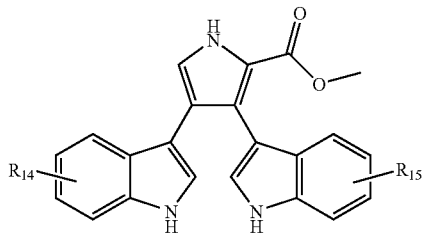

UV spectrometry (Acetonitrile/H$_2$O) $\lambda_{max}$=230, 291

Mass spectrometry: HRESI MS M+H=442.0510 C$_{22}$H$_{15}$N$_3$O$_2$FCl$_2$ (442.0525)=3.4 ppm In Formula XXI', R$_{14}$ can either be two chlorides, a single fluorine, or no halogen substituent, with R$_{15}$ being a fluourine, two chlorides, none, or both, respectively. For example, in one embodiment, Formula XXI' is that shown in Formula XXI:

Formula XXI

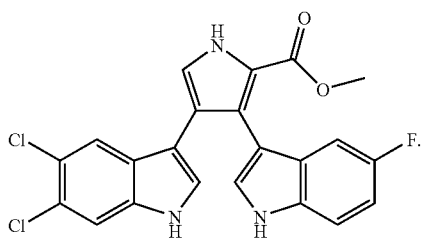

Additionally, the synthesis of the compound of Formula XXI can also result in a composition that comprises additional substances as well the substance of Formula XXI'.

For the compound of Formula XXII:

Formula XXII

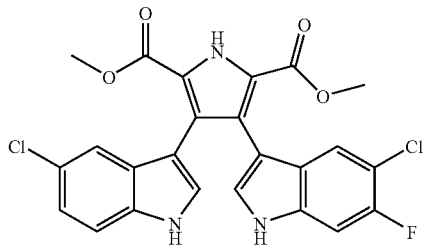

UV spectrometry (Acetonitrile/H$_2$O) $\lambda_{max}$=229, 262, sh 300

HRESI MS M+H=500.0588 $\Delta_{calc}$ C$_{24}$H$_{17}$N$_3$O$_4$FCl$_2$ (500.0580)=1.5 ppm For the compound of Formula XXIII:

Formula XXIII

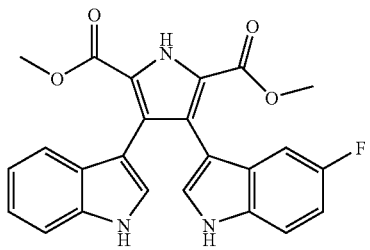

UV spectrometry (Acetonitrile/H$_2$O) $\lambda_{max}$=223, 268, sh 321

HRESI MS M+H=432.1350 $\Delta_{calc}$ C$_{24}$H$_{91}$N$_3$O$_4$F (432.1360)=−2.1 ppm For the compound of Formula XXIV:

Formula XXIV

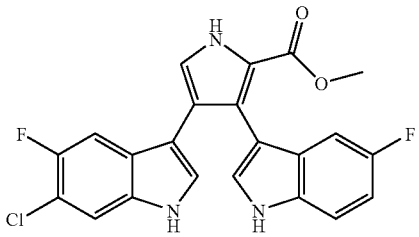

UV spectrometry (Acetonitrile/H$_2$O): $\lambda_{max}$=227, 290 nm

HRESI MS M+H=426.0819 $\Delta_{calc}$ C$_{22}$H$_{15}$N$_3$O$_2$F$_2$Cl$_2$ (426.0821)=−0.3 ppm For the compound of Formula XXV:

Formula XXV

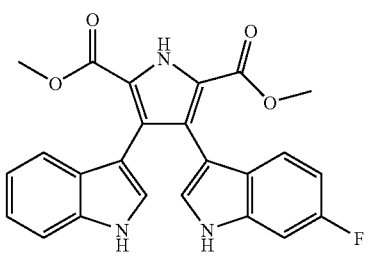

UV spectrometry (Acetonitrile/H$_2$O) $\lambda_{max}$=224, 270, sh 320

HRESI MS M+H=432.1349 $\Delta_{calc}$ C$_{24}$H$_{19}$N$_3$O$_4$F (432.1360)=−2.4 ppm For the compound of Formula XXVI:

Formula XXVI

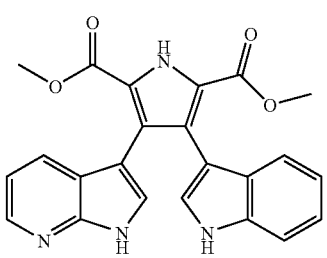

UV spectrometry (Acetonitrile w/0.05% Formic acid/H$_2$O w/0.05% Formic acid) $\lambda_{max}$=223, 272

HRESI MS M+H=415.1402 $\Delta_{calc}$ C$_{23}$H$_{19}$N$_4$O$_4$ (415.1406)=−1.0 ppm The compounds are characterized by the above properties and have structures that can be elucidated using the data described above and in the Examples.

Pharmaceutical Compositions

In one embodiment, the compounds disclosed herein are used in pharmaceutical compositions. The compounds can optionally and preferably are produced by the methods disclosed herein. The compounds can be used, for example, in pharmaceutical compositions comprising a pharmaceutically acceptable carrier prepared for storage and subsequent administration. Also, embodiments relate to a pharmaceutically effective amount of the products and compounds disclosed above in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985), which is incorporated herein by reference in its entirety. Preservatives, stabilizers, dyes and even flavoring agents can be provided in the pharmaceutical composition. For example, sodium benzoate, ascorbic acid and esters of p-hydroxybenzoic acid can be added as preservatives. In addition, antioxidants and suspending agents can be used.

The bis-indole pyrroles and analog compositions can be formulated and used as tablets, capsules, or elixirs for oral administration; suppositories for rectal administration; sterile solutions, suspensions for injectable administration; patches for transdermal administration, and sub-dermal deposits and the like. Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions can contain minor amounts of nontoxic auxiliary substances, such as wetting agents, pH buffering agents, and the like. If desired, absorption enhancing preparations (for example, liposomes), can be utilized.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions can contain substances that increase the viscosity of the suspension, such as sodium carboxymethyl cellulose, sorbitol, or dextran. Optionally, the suspension can also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate. Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses. Such formulations can be made using methods known in the art (see, for example, U.S. Pat. No. 5,733,888 (injectable compositions); U.S. Pat. No. 5,726,181 (poorly water soluble compounds); U.S. Pat. No. 5,707,641 (therapeutically active proteins or peptides); U.S. Pat. No. 5,667,809 (lipophilic agents); U.S. Pat. No. 5,576,012 (solubilizing polymeric agents); U.S. Pat. No. 5,707,615 (anti-viral formulations); U.S. Pat. No. 5,683,676 (particulate medicaments); U.S. Pat. No. 5,654,286 (topical formulations); U.S. Pat. No. 5,688,529 (oral suspensions); U.S. Pat. No. 5,445,829 (extended release formulations); U.S. Pat. No. 5,653,987 (liquid formulations); U.S. Pat. No. 5,641,515 (controlled release formulations) and U.S. Pat. No. 5,601,845 (spheroid formulations); all of which are incorporated herein by reference in their entireties.

Further disclosed herein are various pharmaceutical compositions well known in the pharmaceutical art for uses that include intraocular, intranasal, and intraauricular delivery. Pharmaceutical formulations include aqueous ophthalmic solutions of the active compounds in water-soluble form, such as eyedrops, or in gellan gum (Shedden et al., *Clin. Ther.*, 23(3):440–50 (2001)) or hydrogels (Mayer et al., *Ophthalmologica*, 210(2):101–3 (1996)); ophthalmic ointments; ophthalmic suspensions, such as microparticulates, drug-containing small polymeric particles that are suspended in a liquid carrier medium (Joshi, A. 1994 *J Ocul Pharmacol* 10:29–45), lipid-soluble formulations (Alm et al., *Prog. Clin. Biol. Res.*, 312:447–58 (1989)), and microspheres (Mordenti, *Toxicol. Sci.*, 52(1):101–6 (1999)); and ocular inserts. All of the above-mentioned references, are incorporated herein by reference in their entireties. Such suitable pharmaceutical formulations are most often and preferably formulated to be sterile, isotonic and buffered for stability and comfort. Pharmaceutical compositions can also include drops and sprays often prepared to simulate in many respects nasal secretions to ensure maintenance of normal ciliary action. As disclosed in Remington's Pharmaceutical Sciences (Mack Publishing, 18$^{th}$ Edition), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

When used as an antimicrobial compound, the compound of Formula (I) or compositions including Formula (I) can be administered by either oral or non-oral pathways. When administered orally, it can be administered in capsule, tablet, granule, spray, syrup, or other such form. When administered non-orally, it can be administered as an aqueous suspension, an oily preparation or the like or as a drip, suppository, salve, ointment or the like, when administered via injection, subcutaneously, intraperitoneally, intravenously, intramuscularly, or the like.

In one embodiment, the antimicrobials can be mixed with additional substances to enhance their effectiveness. In one embodiment, the antimicrobial is combined with an additional antimicrobial. In another embodiment, the antimicrobial is combined with a drug or medicament that is helpful to a patient that is taking antimicrobials.

Methods of Administration

In an alternative embodiment, the disclosed chemical compounds and the disclosed pharmaceutical compositions are administered by a particular method as an antimicrobial. Such methods include, among others, (a) administration though oral pathways, which administration includes administration in capsule, tablet, granule, spray, syrup, or other such forms; (b) administration through non-oral pathways, which administration includes administration as an aqueous suspension, an oily preparation or the like or as a drip, suppository, salve, ointment or the like; administration via injection, subcutaneously, intraperitoneally, intravenously, intramuscularly, intradermally, or the like; as well as (c) administration topically, (d) administration rectally, or (e) administration vaginally, as deemed appropriate by those of skill in the art for bringing the compound of the present embodiment into contact with living tissue; and (f) administration via controlled released formulations, depot formulations, and infusion pump delivery. As further examples of such modes of administration and as further disclosure of modes of administration, disclosed herein are various methods for administration of the disclosed chemical compounds and pharmaceutical compositions including modes of administration through intraocular, intranasal, and intraauricular pathways.

The pharmaceutically effective amount of the bis-indole pyrroles and analog compositions required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

In practicing the methods of the embodiment, the products or compositions can be used alone or in combination with one another, or in combination with other therapeutic or diagnostic agents. These products can be utilized in vivo, ordinarily in a mammal, preferably in a human, or in vitro. In employing them in vivo, the products or compositions can be administered to the mammal in a variety of ways, including parenterally, intravenously, subcutaneously, intramuscularly, colonically, rectally, vaginally, nasally or intraperitoneally, employing a variety of dosage forms. Such methods can also be applied to testing chemical activity in vivo.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage can range broadly, depending upon the desired affects and the therapeutic indication. Typically, dosages can be between about 10 microgram/kg and 100 mg/kg body weight, preferably between about 100 microgram/kg and 10 mg/kg body weight. Alternatively dosages can be based and calculated upon the surface area of the patient, as understood by those of skill in the art. Administration is preferably oral on a daily or twice daily basis.

The exact formulation, route of administration and dosage can be chosen by the individual physician in view of the patient's condition. See for example, Fingl et al., in The Pharmacological Basis of Therapeutics, 1975, which is incorporated herein by reference in its entirety. It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition can, for example, be evaluated, in part, by standard prognostic evaluation methods. Further, the dose and perhaps dose frequency, will also vary according to the age, body weight, and response of the individual patient. A program comparable to that discussed above can be used in veterinary medicine.

Depending on the specific conditions being treated, such agents can be formulated and administered systemically or locally. A variety of techniques for formulation and administration can be found in Remington's Pharmaceutical Sciences, 18th Ed., Mack Publishing Co., Easton, Pa.(1990), which is incorporated herein by reference in its entirety. Suitable administration routes can include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

For injection, the agents of the embodiment can be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art. Use of pharmaceutically acceptable carriers to formulate the compounds herein disclosed for the practice of the embodiment into dosages suitable for systemic administration is within the scope of the embodiment. With proper choice of carrier and suitable manufacturing practice, the compositions disclosed herein, in particular, those formulated as solutions, can be administered parenterally, such as by intravenous injection. The compounds can be formulated readily using pharmaceutically acceptable carriers well known in the art into dosages suitable for oral administration. Such carriers enable the compounds of the embodiment to be formulated as tablets, pills, capsules, liquids, gels, syrups, slurries, suspensions and the like, for oral ingestion by a patient to be treated.

Agents intended to be administered intracellularly can be administered using techniques well known to those of ordinary skill in the art. For example, such agents can be encapsulated into liposomes, then administered as described above. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. Additionally, due to their hydrophobicity, small organic molecules can be directly administered intracellularly.

Determination of the effective amounts is well within the capability of those skilled in the art, especially in light of the detailed disclosure provided herein. In addition to the active ingredients, these pharmaceutical compositions can contain suitable pharmaceutically acceptable carriers comprising excipients and auxiliaries which facilitate processing of the active compounds into preparations which can be used pharmaceutically. The preparations formulated for oral administration can be in the form of tablets, dragees, capsules, or solutions. The pharmaceutical compositions can be manufactured in a manner that is itself known, for example, by means of conventional mixing, dissolving, granulating, dragee-making, levitating, emulsifying, encapsulating, entrapping, or lyophilizing processes.

Compounds disclosed herein can be evaluated for efficacy and toxicity using known methods. For example, the toxicology of a particular compound, or of a subset of the compounds, sharing certain chemical moieties, can be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, dogs or monkeys, can be determined using known methods. The efficacy of a particular compound can be established using several art recognized methods, such as in vitro methods, animal models, or human clinical trials. Art-recognized in vitro models exist for nearly every class of condition, including the conditions abated by the compounds disclosed herein, including cancer, cardiovascular disease, and various immune dysfunction, and infectious diseases. Similarly, acceptable animal models can be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

When used as an antimicrobial, the compounds disclosed herein can be administered by either oral or a non-oral pathways. When administered orally, it can be administered in capsule, tablet, granule, spray, syrup, or other such form. When administered non-orally, it can be administered as an aqueous suspension, an oily preparation or the like or as a drip suppository, salve, ointment or the like, when administered via injection, subcutaneously, intraperitoneally, intravenously, intramuscularly, intradermally, or the like. Controlled release formulations, depot formulations, and infusion pump delivery are similarly contemplated.

The compositions disclosed herein in pharmaceutical compositions can also comprise a pharmaceutically acceptable carrier. Such compositions can be prepared for storage and for subsequent administration. Acceptable carriers or diluents for therapeutic use are well known in the pharmaceutical art, and are described, for example, in Remington's Pharmaceutical Sciences, Mack Publishing Co. (A. R. Gennaro edit. 1985). For example, such compositions can be formulated and used as tablets, capsules or solutions for oral administration; suppositories for rectal or vaginal administration; sterile solutions or suspensions for injectable administration. Injectables can be prepared in conventional forms, either as liquid solutions or suspensions, solid forms suitable for solution or suspension in liquid prior to injection, or as emulsions. Suitable excipients include, but are not limited to, saline, dextrose, mannitol, lactose, lecithin, albumin, sodium glutamate, cysteine hydrochloride, and the like. In addition, if desired, the injectable pharmaceutical compositions can contain minor amounts of nontoxic auxiliary substances, such as wetting agents, pH buffering agents, and the like. If desired, absorption enhancing preparations (for example, liposomes), can be utilized.

The pharmaceutically effective amount of the composition required as a dose will depend on the route of administration, the type of animal being treated, and the physical characteristics of the specific animal under consideration. The dose can be tailored to achieve a desired effect, but will depend on such factors as weight, diet, concurrent medication and other factors which those skilled in the medical arts will recognize.

The products or compositions of the embodiment, as described above, can be used alone or in combination with one another, or in combination with other therapeutic or diagnostic agents. These products can be utilized in vivo or in vitro. The useful dosages and the most useful modes of administration will vary depending upon the age, weight and animal treated, the particular compounds employed, and the specific use for which these composition or compositions are employed. The magnitude of a dose in the management or treatment for a particular disorder will vary with the severity of the condition to be treated and to the route of administration, and depending on the disease conditions and their severity, the compositions can be formulated and administered either systemically or locally. A variety of techniques for formulation and administration can be found in Remington's Pharmaceutical Sciences, 18th ed., Mack Publishing Co., Easton, Pa. (1990).

To formulate the compounds of Formula (I) as an antimicrobial, known surface active agents, excipients, smoothing agents, suspension agents and pharmaceutically acceptable film-forming substances and coating assistants, and the like can be used. Preferably alcohols, esters, sulfated aliphatic alcohols, and the like can be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like can be used as excipients; magnesium stearate, talc, hardened oil and the like can be used as smoothing agents; coconut oil, olive oil, sesame oil, peanut oil, soya can be used as suspension agents or lubricants; cellulose acetate phthalate as a derivative of a carbohydrate such as cellulose or sugar, or methylacetate-methacrylate copolymer as a derivative of polyvinyl can be used as suspension agents; and plasticizers such as ester phthalates and the like can be used as suspension agents. In addition to the foregoing preferred ingredients, sweeteners, fragrances, colorants, preservatives and the like can be added to the administered formulation of the compound produced by the method of the embodiment, particularly when the compound is to be administered orally.

The compounds and compositions can be orally or non-orally administered to a human patient in the amount of about 0.001 mg/kg/day to about 10,000 mg/kg/day of the active ingredient, and more preferably about 0.1 mg/kg/day to about 100 mg/kg/day of the active ingredient at, preferably, one time per day or, less preferably, over two to about ten times per day. Alternatively and also preferably, the compound produced by the method of the embodiment can preferably be administered in the stated amounts continuously by, for example, an intravenous drip. Thus, for the example of a patient weighing 70 kilograms, the preferred daily dose of the active or anti-infective ingredient would be about 0.07 mg/day to about 700 gm/day, and more preferable, 7 mg/day to about 7 grams/day. Nonetheless, as will be understood by those of skill in the art, in certain situations it can be necessary to administer the or the anti-infective compound of the embodiment in amounts that excess, or even far exceed, the above-stated, preferred dosage range to effectively and aggressively treat particularly advanced s or infections.

In the case of using the antimicrobial produced by methods of the embodiment as a biochemical test reagent, the compound produced by methods of the embodiment inhibits the progression of the disease when it is dissolved in an organic solvent or hydrous organic solvent and it is directly applied to any of various cultured cell systems. Usable organic solvents include, for example, methanol, methylsulfoxide, and the like. The formulation can, for example, be a powder, granular or other solid inhibitor, or a liquid inhibitor prepared using an organic solvent or a hydrous organic solvent. While a preferred concentration of the compound produced by the method of the embodiment for use as an antimicrobial, anticancer or anti-tumor compound is generally in the range of about 1 to about 100 µg/ml, the most appropriate use amount varies depending on the type of cultured cell system and the purpose of use, as will be appreciated by persons of ordinary skill in the art. Also, in certain applications it can be necessary or preferred to persons of ordinary skill in the art to use an amount outside the foregoing range.

In one embodiment, the method of using a compound of Formula I as an antimicrobial involves administering an effective amount of a bis-indole pyrrole. In a preferred embodiment, the method involves administering the compound represented by Formula II, to a patient in need of an antimicrobial, until the need is effectively reduced or more preferably removed.

As will be understood by one of skill in the art, "need" is not an absolute term and merely implies that the patient can benefit from the treatment of the antimicrobial in use. By "patient" what is meant is an organism that can benefit by the use of an antimicrobial. For example, any organism with *H. influenzae* or *E. coli* may benefit from the application of an antimicrobial that can in turn reduce the amount of microbes present in the patient. In one embodiment, the patient's health may not require that an antimicrobial be administered, however, the patient can still obtain some benefit by the reduction of the level of microbes present in the patient, and thus be in need. In one embodiment, the antimicrobial is effective against one type of microbe, but not against other types; thus, allowing a high degree of selectivity in the treatment of the patient. In choosing such an antimicrobial, the methods and results disclosed in the Examples can be useful. In an alternative embodiment, the antimicrobial is effective against a broad spectrum of microbes, preferably a broad spectrum of foreign, and, more preferably, harmful bacteria, to the host organism. In yet another embodiment, the antimicrobial is effective against all microbes, even those native to the host. Examples of microbes that can be targets of antimicrobials, include, but are not limited to, *B. anthracis, B. cereus, E. coli, S. pneumoniae, S. pyogenes, H. influenzae, S. epidermidis, S. aureus, E. faecalis, E. faecium* and the like.

"Therapeutically effective amount," "pharmaceutically effective amount," or similar term, means that amount of drug or pharmaceutical agent that will result in a biological or medical response of a cell, tissue, system, animal, or human that is being sought. In a preferred embodiment, the medical response is one sought by a researcher, veterinarian, medical doctor, or other clinician.

"Antimicrobial" refers to a compound that reduces the likelihood of survival of microbes. In one embodiment, the likelihood of survival is determined as a function of an individual microbe; thus, the antimicrobial will increase the chance that an individual microbe will die. In one embodiment, the likelihood of survival is determined as a function of a population of microbes; thus, the antimicrobial will increase the chances that there will be a decrease in the population of microbes. In one embodiment, antimicrobial means antibiotic or other similar term. Such antimicrobials are capable of destroying or suppressing the growth or reproduction of microorganisms, such as bacteria. For example, such antibacterials and other antimicrobials are described in Antibiotics, Chemotherapeutics and Antibacterial Agents for Disease Control (M. Grayson, editor, 1982), and E. Gale et al., The Molecular Basis of Antibiotic Action 2d edition (1981). In another embodiment, an antimicrobial will not change the likelihood of survival, but will change the chances that the microbes will be harmful to the host in some way. For instance, if the microbe secretes a substance that is harmful to the host, the antimicrobial can act upon the microbe to stop the secretion. In one embodiment, an antimicrobial, while, increasing the likelihood that the microbe(s) will die, is minimally harmful to the surrounding, nonmicrobial, cells. In an alternative embodiment, it is not important how harmful the antimicrobial is to surrounding, nonmicrobial, cells, as long as it reduces the likelihood of survival of the microbe.

In one embodiment, a bis-indole pyrrole is considered an effective antimicrobial if the bis-indole pyrrole can influence 10% of the microbes. In a more preferred embodiment, the bis-indole pyrrole is effective if it can influence 10 to 50% of the microbes. In an even more preferred embodiment, the bis-indole pyrrole is effective if it can influence 50–80% of the microbes. In an even more preferred embodiment, the bis-indole pyrrole is effective if it can influence 80–95% of the microbes. In an even more preferred embodiment, the bis-indole pyrrole is effective if it can influence 95–99% of the microbes. "Influence" is defined by the mechanism of action for each compound. Thus, for example, if a compound prevents the reproduction of microbes, then influence is a measure of prevention of reproduction. Likewise, if a compound destroys microbes, then influence is a measure of microbe death. Not all mechanisms of action need be at the same percentage of effectiveness. In an alternative embodiment, a low percentage effectiveness can be desirable if the lower degree of effectiveness is offset by other factors, such as the specificity of the compound, for example. Thus a compound that is only 10% effective, for example, but displays little in the way of harmful side-effects to the host, or non-harmful microbes, can still be considered effective.

In one embodiment, the compounds described herein are administered simply to remove microbes, and need not be administered to a patient. For example, in situations where microbes can present a problem, such as in food products, the compounds described herein can be administered directly to the products to reduce the risk of microbes in the products. Alternatively, the compounds can be used to reduce the level of microbes present in the surrounding environment, such working surfaces. After the compounds are administered they can optionally be removed. This can be particularly desirable in situations where work surfaces or food products can come into contact with other surfaces or organisms that could risk being harmed by the compounds. In an alternative embodiment, the compounds can be left in the food products or on the work surfaces to allow for a more protection. Whether or not this is an option will depend upon the relative needs of the situation and the risks associated with the compound, which in part can be determined as described in the Examples below.

The following non-limiting examples are meant to describe the preferred embodiments of the methods. Variations in the details of the particular methods employed and in the precise chemical compositions obtained will undoubtedly be appreciated by those of skill in the art.

EXAMPLE 1

Production of Compounds of Formulae II, III, IV, VI and XI

Fermentation. Strain NPS012745 was grown in a 40 ml tube containing 10 ml of vegetative medium consisting of the following per liter of sea water: starch, 10 g; yeast extract, 4 g; and peptone, 2 g. The culture was allowed to incubate for 3 days at 28 degrees C. on a rotary shaker operating at 250 rpm. The vegetative culture was mixed with 2 ml of cryoprotective solution consisting of 500 g glycerol per liter of deionized water. 1.5 ml portions of this mixture were transferred to sterile cryogenic tube (2 ml capacity). The vegetative cultures so obtained were frozen and stored at −80 degrees C.

Seed culture for the production of NPS012745 compounds was prepared by transferring 1.5 ml of the cryopreservative culture to a 40 ml tube containing 10 ml of sterile vegetative medium having the same composition as the above. The seed culture was incubated at 28 degrees C. for 3 days on a rotary shaker operating at 250 rpm. Five ml of this seed culture was inoculated into 500 ml flask containing 100 ml of the vegetative medium. The second seed cultures were incubated at 28 degrees C. for 2 days on a rotary shaker operating at 250 rpm. Five ml each of the second seed culture was inoculated into ten 500 ml flask containing 100 ml of the vegetative medium. The third seed cultures were incubated at 28 degrees C. for 2 days on a rotary shaker operating at 250 rpm. Five ml each of the third seed culture was inoculated into the production medium having the same composition as the vegetative medium. The production culture was incubated at 28 degree C. for 7 days on a rotary shaker operating at 250 rpm. The culture broth was first shaken with 500 ml Acetone for 15 minutes and then extracted with 10 L of EtOAc and the extract was dried in vacuo. The dried extract was then processed for the recovery of Compounds of Formulae II, III, IV, VI and XI.

Purification. The pure compounds of Formulae II, III, IV, VI, and XI can be obtained by HPLC chromatography as described below:

| Column: | ACE 5 C18-HL |
|---|---|
| Dimensions: | 15 cm × 21 mm ID |
| Flow rate: | 14.5 ml/min |
| Detection: | 290 nm |
| Solvent: | Gradient of 60% MeOH 40% $H_2O$ to 100% MeOH (15 min) |

Fifty mg of the crude extract is dissolved in DMSO (900 μl) and this solution is injected on the HPLC column. This solution is injected using the HPLC chromatography conditions described above and the compounds of interest elude in the order shown in FIG. 1. The fractions containing the bis-indole pyrroles can be further purified using a semi-preparative HPLC method described below:

| Column: | ACE 5 C18-HL |
|---|---|
| Dimensions: | 10 mm × 250 mm ID |
| Flow rate: | 3 ml/min |
| Detection: | UV DAD |
| Solvent: | Gradient of 60% MeOH 40% $H_2O$ to 100% MeOH (20 min) Or Isocratic 65% MeOH 35% H2O containing 0.1% ammonium acetate. |

The partially purified bis-indole-pyrrole natural products of Formulae II, III, IV, VI, and XI can be obtained as pure materials using the conditions described above. The partially purified products have the following spectroscopic characteristics.

Compound of Formula II: UV spectrometry (Acetonitrile/$H_2O$) $\lambda_{max}$=231, 292 nm. Mass spectrometry: HRESI MS M+Na=480.0059 $\Delta_{calc}$ $C_{22}H_{14}N_3O_2Cl_3Na$ (480.0049)=1.9 ppm. $^1H$ NMR ($CD_2Cl_2$) see Table 1; $^{13}C$ NMR ($CD_2Cl_2$) see Table 2.

Compound of Formula III: UV spectrometry (Acetonitrile/$H_2O$): $\lambda_{max}$=230, 290 nm Mass spectrometry: HRESI MS M+H=424.0612 $\Delta_{calc}$ $C_{22}H_{16}N_3O_2Cl_2$ (424.0620)=0.7 ppm. $^1H$ NMR ($CD_2Cl_2$) see Table 1; $^{13}C$ NMR ($CD_2Cl_2$) see Table 2.

Compound of Formula IV: UV spectrometry (Acetonitrile/$H_2O$) $\lambda_{max}$=239, 299. Mass spectrometry: HRESI MS M+H=433.9771 $\Delta_{calc}$ $C_{20}H_{12}N_3Cl_4$ (433.9785)=3.4 ppm. $^1H$ NMR ($CD_2Cl_2$) see Table 1; $^{13}C$ NMR ($CD_2Cl_2$) see Table 2.

Compound of Formula VI: UV spectrometry (Acetonitrile/$H_2O$) $\lambda_{max}$=229, 262, sh 300. Mass spectrometry: HRESI MS M+H=482.0657 $\Delta_{calc}$ $C_{24}H_{18}N_3O_4Cl_2$ (482.0674)=3.7 ppm. $^1H$ NMR ($CD_2Cl_2$) see Table 1; $^{13}C$ NMR ($CD_2Cl_2$) see Table 2.

Compound of Formula XI: UV (Acetonitrile/$H_2O$, 0.05% formic acid) $\lambda_{max}$=224, 266 nm. HRESI MS M+H=448.1068 $\Delta_{calc}$ $C_{24}H_{19}N_3O_4Cl$ (448.1064)=0.7 ppm. $^1H$ NMR ($CD_2Cl_2$) see FIG. 3A.

Directed Biosynthesis

One embodiment concerns novel antibiotic compounds, or pharmaceutically acceptable salts thereof, which are de-chlorinated; brominated; fluorinated; or azatryptophan analogs of Formula I compounds produced by directed biosynthesis with Formula I compounds producing organism, or mutant thereof. The fermentation process is accomplished under submerged aerobic conditions in an aqueous medium containing carbon and nitrogen nutrient for a sufficient time to produce the novel antibiotics.

EXAMPLE 2

Production of De-Chlorinated NPS012745 Compound of Formula IX

Fermentation. Seed culture of strain NPS012745 was prepared by transferring 1.5 ml of the cryopreservative culture to a 40 ml tube containing 10 ml of sterile vegetative medium consisting of the following per liter of sea water: starch, 10 g; yeast extract, 4 g; and peptone, 2 g. The seed culture was incubated at 28 degrees C. for 3 days on a rotary shaker operating at 250 rpm. Five ml of this seed culture was inoculated into 500 ml flask containing 100 ml of the vegetative medium. The second seed culture was incubated at 28 degrees C. for 2 days on a rotary shaker operating at 250 rpm. Five ml each of the second seed culture was inoculated into 500 ml flask containing 100 ml of the production medium consisting of the following per liter of deionized water: starch, 10 g; yeast extract, 4 g; and peptone, 2 g. The production culture was incubated at 28 degrees C. for 7 days on a rotary shaker operating at 250 rpm. The culture broth was extracted with equal volume of ethyl acetate. The extract was dried in vacuo. The dried extract, containing the de-chlorinated NPS012745 compound, was then processed for the recovery of new de-chlorinated NPS012745 analog of Formula IX.

Purification.

The compound of Formula IX was obtained by reversed-phase HPLC using a Gilson HPLC equipped with a 215 fraction collector using detection by UV absorbance at 214 nm. Crude extract was dissolved in 10 ml of neat DMSO. Aliquots (900 µl) of this solution were injected onto a reversed-phase HPLC column (ACE 5 µ C18-HL, 150 mm length by 21 mm ID) using a solvent gradient of 40% ACN/60% $H_2O$ to 100% ACN over 15 min at a flow rate of 14.5 ml/min. The compound of Formula IX eluted at 10.5 min and fractions containing the pure compound from consecutive runs were pooled and dried to yield 5.6 mg of compound, with a purity of >97%.

An additional purification step by semi-preparatory reverse phase HPLC was used to eliminate brown discoloration from the sample. The sample (5.6 mg) was dissolved in 100% DMSO at a concentration of 1.0 mg/ml and 250 µl was loaded on an HPLC column of dimensions 9.4 mm i.d. by 250 mm length containing Eclipse XDB-C18 support. The solvent gradient increased linearly from 60% MeOH/40% $H_2O$ to 100% MeOH over 16 minutes at a flow rate of 3 ml/min. The solvent composition was then held at 100% MeOH for 3 minutes before returning to the starting solvent mixture. Compound of Formula IX eluted at 9.5 min as a white solid with a final purity of 98.7%. The spectroscopic characteristics of the compound of Formula IX include the following: UV spectrometry (Acetonitrile/$H_2O$) $\lambda_{max}$=225, 269, sh 321; Mass spectrometry: HRESI MS M+H=414.1449 $\Delta_{calc}$ $C_{24}H_{20}N_3O_4$ (414.1454)=1.2 ppm; and $^1H$ NMR ($CD_2Cl_2$) see Table 1.

EXAMPLE 3

Production of Fluorinated NPS012745 Compounds

Fermentation.

Seed culture of strain NPS012745 was prepared by transferring 1.5 ml of the cryopreservative culture to a 40 ml tube containing 10 ml of sterile vegetative medium consisting of the following per liter of sea water: starch, 10 g; yeast extract, 4 g; and peptone, 2 g. The seed culture was incubated at 28 degrees C. for 3 days on a rotary shaker operating at 250 rpm. Five ml of this seed culture was inoculated into 500 ml flask containing 100 ml of the vegetative medium. The second seed culture was incubated at 28 degrees C. for 2 days on a rotary shaker operating at 250 rpm. Five ml each of the second seed culture was inoculated into 500 ml flask containing 100 ml of the production medium consisting of the following per liter of deionized water: starch, 10 g; yeast extract, 4 g; peptone, 2 g and synthetic sea salt (Instant Ocean, Aquarium Systems), 30 g. The production culture was incubated at 28 degrees C. for 2 days on a rotary shaker operating at 250 rpm. 5-Fluorotryptophan (25 mg in 8 ml 0.01% NaOH) or 6-fluorotryptophan (25 mg in 8 ml 0.01% NaOH) was added to the production culture. The production culture was further incubated at 28 degrees C. for 5 days on a rotary shaker operating at 250 rpm. The culture broth was extracted with equal volume of ethyl acetate. The extract was dried in vacuo. The dried extract, containing the fluorinated NPS012745 compounds, was then processed for the recovery of new fluorinated NPS012745 analogs.

Purification of 6-Fluoro Analogs

In order isolate 6-fluoro analogs from the complex crude extract (2.28 g), a reverse-phase preparatory HPLC method was used for the initial purification step. Crude extract was dissolved in 36 ml of 5:4 DMSO/MeOH solvent mixture and 900 µl aliquots of this solution were injected onto a reversed-phase HPLC column (ACE 5 µ C18-HL, 150 mm length by 21 mm ID) on a Gilson HPLC system. The solvent gradient started at 50% MeOH/50% $H_2O$ and increased linearly to 80% MeOH/20% $H_2O$ over 15 min and then continued to 100% MeOH in 2 min at a flow rate of 14.5 ml/min. UV absorbance at 214 nm was used to detect the elution of compounds and fractions were collected every 0.5 min using the 215 fraction collector. Desired compounds eluted between 10.5 and 17 minutes and these fractions, were analyzed using analytical HPLC methods to determine their composition.

Further purification of individual compounds was achieved using a normal-phase HPLC isocratic method developed on a Hitachi HPLC system with L-7150 preparation pump. A fraction (91.0 mg) enriched in compound of Formula XVII was dissolved in EtOAc to a final concentration of 10 mg/ml and 300 µl aliquots were loaded onto a normal phase silica column (Phenomenex Luna Si 10 µ, 100 Å; 250 mm length by 21.2 mm id). A 45 min HPLC method containing an isocratic solvent system of 62% Hex/38% EtOAc with flow rate of 14.5 ml/min was used to separate desired compound of Formula XVII, away from the other components. The chromatography was monitored by UV absorbance at 210 nm and peaks were collected manually. Compound of Formula XVII eluted after 25 minutes with purity >90%. Another fraction (32.3 mg) which was enriched in compound of Formula XXII was processed using the same method and parameters as described above. Compound of Formula XXII eluted at 38 minutes, yielding 5.3 mg of relatively pure compound.

The isocratic normal phase method was transferred to a Gilson HPLC equipped with pump heads with a maximum flow rate of 200 ml/min and a Gilson 215 fraction collector, using detection by UV absorbance at 214 nm. A fraction (8.8 mg) obtained from partial purification of the crude extract and containing compound of Formula XXV was dissolved in EtOAc to a final concentration of 1 mg/ml and 350 µl aliquots were injected on normal phase silica column (Phenomenex Luna Si 10 µ, 100 Å; 250 mm length by 21.2 mm id). An isocratic solvent gradient with a solvent mixture of 62% Hex/38% EtOAc and a flow rate of 14.5 m/min was used to isolate compound of Formula XXV, which eluted as a relatively pure compound after 27 minutes.

The UV spectroscopic and NMR data for the products described above are presented below.

Compound of Formula XVII: UV spectrometry (Acetonitrile/H$_2$O) $\lambda_{max}$=231, 291. HRESI MS M+H=442.0541 $\Delta_{calc}$ C$_{22}$H$_{15}$N$_3$O$_2$FCl$_2$ (442.0525)=3.5 ppm. $^1$H NMR (CD$_2$Cl$_2$) see FIG. 3F; $^{13}$C NMR (CD$_2$Cl$_2$) 161.36 (C6), 154.70, J$^{CF}$ 239 Hz (C6"), 134.52 (C7a'), 134.36 J$^{CF}$ 11 Hz (C7a"), 129.08 (C3a'), 126.27 (C5'), 124.80 (C5"), 124.12 J$^{CF}$ 15 Hz (C5") 124.08 (C2"), 122.23 (C6'), 120.93, 120.93 (overlap), 120.01, 113.67 J$^{CF}$ 20 Hz (C3a"), 112.48, 110.61 (C3"), 109.91 (C3'), 98.8J$^{CF}$ 26 Hz (C7"), 51.46 (C7).

Compound of Formula XXII: UV spectrometry (Acetonitrile/H$_2$O) $\lambda_{max}$=229, 262, sh 300. HRESI MS M+H=500.0588 $\Delta_{calc}$ C$_{24}$H$_{17}$N$_3$O$_4$FCl$_2$ (500.0580)=1.5 ppm; $^1$H NMR (CD$_2$Cl$_2$) see FIG. 3I.

Compound of Formula XXV: UV spectrometry (Acetonitrile/H2O) $\lambda$max=224, 270, sh 320. HRESI MS M+H=432.1349 $\Delta$calc C$_{24}$H$_{19}$N$_3$O$_4$F (432.1360)=-2.4 ppm; $^1$H NMR (CD$_2$C$_{12}$) see FIG. 3L.

Purification of 5-Fluoro Analogs

The initial reverse-phase purification step used to separate components of the crude extract containing 5-fluoro analogs was identical to the one described above for the initial purification of 6-fluoro analogs. The resulting fractions that eluted between 10 and 17 minutes were analyzed by HPLC-MS to determine the composition of each fraction.

Fractions obtained from partial purification of crude extract described above were further purified to obtain pure compounds. One of the fractions contained a mixture of compounds of Formulae XVIII and XXIII. An isocratic normal phase HPLC method utilizing 62% hexane/38% EtOAc and a flow rate of 14.5 ml/min was used to separate the two compounds. The fraction (24.8 mg) was dissolved in EtOAc to a final concentration of 6 mg/ml and 350 µl aliquots were injected on normal phase silica column (Phenomenex Luna Si 10 µ, 100 Å; 250 mm length by 21.2 mm id). Relatively pure compounds of Formulae XXIII and XVIII eluted after 29 minutes and 35 minutes respectively.

Other fractions obtained from partial purification of crude extract were further processed to obtain analogs of Formulae XX, XXI', and XXIV using the same isocratic method described above for compounds of Formulae XXIII and XVIII. Compound of Formula XX eluted after 35 minutes with purity >98%. Compound of Formula XXI' eluted after 25 minutes; however, the sample appeared to contain approximately 30% of the compound of Formula II. Compound of Formula XXIV eluted after 26 min; this compound was further purified by dissolving in 750 µl of 2:1 H$_2$O/MeOH (6.2 mg compound), loading onto a C-18 Sep-pak, and eluting with 10 ml of 70% MeOH/30% H$_2$O. The spectroscopic data relating to the above compounds of the various Formulae are presented below.

Compound of Formula XVIII: UV spectrometry (Acetonitrile/H2O) $\lambda_{max}$=224, 268, sh 338; HRESI MS M+H=450.1279 $\Delta_{calc}$ C$_{24}$H$_{18}$N$_3$O$_4$F$_2$ (450.1265)=3.1 ppm; $^1$H NMR (CD$_2$Cl$_2$) FIG. 3G.

Compound of Formula XX: UV spectrometry (Acetonitrile/H2O) $\lambda_{max}$=228, 268, sh 340; HRESI MS M+H=466.0966 $\Delta_{calc}$ C$_{24}$H$_{18}$N$_3$O$_4$ClF (466.0970)=0.9 ppm.

Compound of Formula XXI': UV spectrometry (Acetonitrile/H$_2$O) $\lambda_{max}$=230, 291; HRESI MS M+H=442.0510 C$_{22}$H$_{15}$N$_3$O$_2$FCl$_2$ (442.0525)=3.4 ppm.

Compound of Formula XXIII: UV spectrometry (Acetonitrile/H$_2$O) $\lambda_{max}$=223, 268, sh 321. HRESI MS M+H=432.1350 $\Delta_{calc}$ C$_{24}$H$_{19}$N$_3$O$_4$F (432.1360)=-2.1 ppm; $^1$H NMR (CD$_2$Cl$_2$) see FIG. 3J.

Compound of Formula XXIV: UV spectrometry (Acetonitrile/H$_2$O): $\lambda_{max}$=227, 290 nm; HRESI MS M+H=426.0819 $\Delta_{calc}$ C$_{22}$H$_{15}$N$_3$O$_2$F$_2$Cl$_2$ (426.0821)=-0.3 ppm; $^1$H NMR (CD$_2$Cl$_2$) see FIG. 3K.

EXAMPLE 4

Production of 7-azatryptoiphan NPS012745 Compounds

Fermentation.

Seed culture of strain NPS012745 was prepared by transferring 1.5 ml of the cryopreservative culture to a 40 ml tube containing 10 ml of sterile vegetative medium consisting of the following per liter of sea water: starch, 10 g; yeast extract, 4 g; and peptone, 2 g. The seed culture was incubated at 28 degrees C. for 3 days on a rotary shaker operating at 250 rpm. Five ml of this seed culture was inoculated into 500 ml flask containing 100 ml of the vegetative medium. The second seed culture was incubated at 28 degrees C. for 2 days on a rotary shaker operating at 250 rpm. Five ml each of the second seed culture was inoculated into 500 ml flask containing 100 ml of the production medium consisting of the following per liter of deionized water: starch, 10 g; yeast extract, 4 g; peptone, 2 g and synthetic sea salt (INSTANT OCEAN™, Aquarium Systems, (Mentor Ohio) Cat. No. SS-30-05), 30 g. The production culture was incubated at 28 degrees C. for 2 days on a rotary shaker operating at 250 rpm. 5-Fluorotryptophan (25 mg in 8 ml 0.01% NaOH) or 6-fluorotryptophan (25 mg in 8 ml 0.01% NaOH) was added to the production culture. The production culture was further incubated at 28 degrees C. for 5 days on a rotary shaker operating at 250 rpm. The culture broth was extracted with equal volume of ethyl acetate. The extract was dried in vacuo. The dried extract, containing the fluorinated NPS012745 compounds, was then processed for the recovery of new fluorinated NPS012745 analogs.

Initial purification of the crude extract containing 7-azatryptophan analogs was accomplished by vacuum liquid chromatography (VLC) on silica gel. Crude extract (1 g) was dissolved in dichloromethane (5 ml) and loaded onto a normal phase silica VLC column (25 mm diameter×70 mm length). The column was dry packed and eluted in a step gradient with 100 ml volumes of the following mobile phases:
1. 30% EtOAc/70% Hexane
2. 35% EtOAc/65% Hexane
3. 40% EtOAc/60% Hexane
4. 45% EtOAc/55% Hexane
5. 50% EtOAc/50% Hexane
6. 55% EtOAc/45% Hexane
7. 60% EtOAc/40% Hexane
8. 70% EtOAc/30% Hexane
9. 80% EtOAc/20% Hexane
10. 90% EtOAc/10% Hexane
11. 100% EtOAc The majority of the 7-azatryptophan analogs eluted in the 10th step of the gradient as a mixture of XIII, XIV, and XXVI (17.1 mg total mass). The mixture was further purified by reversed-phase semi-preparative HPLC (Eclipse Zorbax XDB C-18, 250 mm×10 mm id, 5 micron) using a Gilson HPLC equipped with a Gilson 215 fraction collector. The sample was dissolved in 20% DMSO/80% methanol at a concentration of 1 mg/ml, and 100 ul aliquots were injected onto the HPLC and eluted with the following mobile phase gradient at a flow rate of 3 ml/min: 50% MeOH/ H$_2$O with 0.1% TFA to 100% MeOH over 20 minutes. The purification was monitored by UV detection at 254 nm. Compounds of Formulae XXVI, XIII, and XIV eluted under these conditions. The spectroscopic data of these compounds are presented below.

Compound of Formula XIII: UV spectrometry (Acetonitrile/H$_2$O) $\lambda_{max}$=230, 292 sh 245; mass spectrometry: HRESI MS M+H=449.1018 $\Delta_{calc}$ C$_{23}$H$_{18}$N$_4$O$_4$Cl (449.1017)=0.3 ppm; $^1$H NMR (DMSO-d$_6$), see FIG. 3B.

Compound of Formula XIV: UV spectrometry (Acetonitrile/H$_2$O) $\lambda_{max}$=229, 290.; mass spectrometry: HRESI MS M+H=425.0567 $\Delta_{calc}$ C$_{21}$H$_{15}$N$_4$O$_2$Cl$_2$ (425.2670)=1.2 ppm; $^1$H NMR (DMSO-d$_6$), see FIG. 3C.

Compound of Formula XXVI: UV spectrometry (Acetonitrile w/0.05% Formic acid/H2O w/0.05% Formic acid) $\lambda_{max}$=223, 272; HRESI MS M+H=415.1402 $\Delta_{calc}$ C$_{23}$H$_{19}$N$_4$O$_4$ (415.1406)=−1.0 ppm; $^1$H NMR (DMSO-d$_6$), see FIG. 3M.

EXAMPLE 5

Production of Brominated Analogs of Formulae XV, XV' and XVI

Fermentation

Seed culture of strain NPS012745 was prepared by transferring 1.5 ml of the cryopreservative culture to a 40 ml tube containing 10 ml of sterile vegetative medium consisting of the following per liter of sea water: starch, 10 g; yeast extract, 4 g; and peptone, 2 g. The seed culture was incubated at 28° C. for 3 days on a rotary shaker operating at 250 rpm. This seed culture (5 ml) was inoculated into 500 ml flask containing 100 ml of the vegetative medium. The second seed culture was incubated at 28° C. for 2 days on a rotary shaker operating at 250 rpm. The second seed culture (5 ml) was inoculated into 500 ml flask containing 100 ml of the production medium consisting of the following per liter of deionized water: glucose, 20 g; L-arginene, 2 g; KE$_2$PO$_4$, 1 g; MgSO$_4$.7H$_2$O, 1 g; ammonium sulfate, 1 g; CaCO3, 2 g; and NaBr, 10 g. The production culture was incubated at 28° C. for 7 days on a rotary shaker operating at 250 rpm. The culture broth was extracted with equal volume of ethyl acetate and the extract dried in vacuo.

Purification

Brominated analogs of Formulae XV, XV', and XVI were isolated from crude extract (376 mg) through two rounds of reverse-phase HPLC on a Gilson HPLC equipped with a Gilson 215 fraction collector using detection by UV absorbance at 214 nm for both rounds. The crude extract was dissolved in 9 ml of neat DMSO and 500 µl of sample was injected on a reversed-phase HPLC column (ACE 5 µ C18-HL, 150 mm length by 21 mm ID) per run. A shallow linear gradient from 60% MeOH/40% H$_2$O to 100% MeOH over 22 minutes at a flow rate of 14.5 ml/min was utilized to separate compounds of Formulae XV, XV', and XVI from closely eluting compound of Formula II.

Separating compounds of Formula XV' from XVI required additional preparatory reverse-phase HPLC. Sample containing both compounds was dissolved in 1:1 DMSO/MeOH at a concentration of 1.0 mg/ml and 500 µl was loaded on reversed-phase HPLC column (ACE 5 µ C18-HL, 150 mm length by 21 mm ID). An isocratic solvent system consisting of 35% H$_2$O/65% MeOH for 30 minutes at a flow rate of 14.5 ml/min was used and compounds of Formulae XV' and XVI eluted at 18 and 20.5 min, respectively. The 2 compounds co-eluted with the compound of Formula VI under these conditions and the presence of the mixture was detected by $^1$H NMR. It appears that for the compound of Formula XV', the compound of Formula VI was present in 5%. A similar percent was identified in compound of Formula XVI. The spectroscopic properties of the products for the synthesis of each of the compounds for the above formulae are presented below.

Compound of Formula XV': UV spectrometry (Acetonitrile/H$_2$O) $\lambda_{max}$=231, 292; HRESI MS M+H=468.0120 $\Delta_{calc}$ C$_{22}$H$_{16}$N$_3$O$_2$ClBr (468.0114)=1.2 ppm; $^1$H NMR (CD$_2$Cl$_2$) see FIG. 3D.

Compound of Formula XVI: UV spectrometry (Acetonitrile/H$_2$O) $\lambda_{max}$=230, 290; HRESI MS M+H=511.9616 $\Delta_{calc}$ C$_{22}$H$_{16}$N$_3$O$_2$Br$_2$ (511.9609)=1.4 ppm; $^1$NMR (CD$_2$Cl$_2$) see FIG. 3E.

EXAMPLE 6

Formation of Base Hydrolysis Semisynthetic Derivatives: Preparation of Ester Hydrolysis Products VII, VIII, and XII A mixture of compounds of Formulae II and VI was hydrolyzed to obtain the corresponding carboxylic acids as follows. The solid sample (24 mg) was dissolved in ACN (6 ml) and basified by the addition of a 2 N solution of sodium hydroxide (5 ml). This resulted in a biphasic mixture. In order to form a miscible solution, 1 ml methanol and 5 ml water were added. The resulting solution was stirred at room temperature for 60 hours, after which time the reaction was acidified by addition of 20 ml 5% HCl solution. This solution was extracted with EtOAc (40 ml, X 3), the combined organic extracts dried using MgSO$_4$, and dried in vacuo. A separate sample of the compound of Formula III was hydrolyzed using identical conditions to those described above.

The organic extract containing the compounds of Formulae VIII and XII was purified by reversed-phase HPLC using a 250×10 mm 5 u ACE column with elution of the compounds using a MeOH/H$_2$O gradient. Under these conditions the compound of Formula VIII (the hydrolysis product of the compound of Formula VI) eluted at 11.5 min, while the compound of Formula XII eluted at 16.5 min. The compound of Formula VII (the hydrolysis product of the compound of Formula III) was similarly purified and eluted at 15.5 min. The spectroscopic data for the above compounds of the particular formulae are described below.

Compound of Formula VII: UV (Acetonitrile/H$_2$O) $\lambda_{max}$=230, 290; ESI MS M+H=410.1; HRESI MS M+H=410.0453 $\Delta_{calc}$ C$_{21}$H$_{14}$N$_3$O$_2$Cl$_2$ (410.0463)=−2.4 ppm.

Compound of Formula VIII: UV (Acetonitrile/H$_2$O) $\lambda_{max}$=230, 265, sh 300; ESIMS M+H=453.8; HRESI MS M+H=454.0355 $\Delta_{calc}$ C$_{22}$H$_{14}$N$_3$O$_4$Cl$_2$ (454.0361)=−1.5 ppm.

Compound of Formula XII: UV spectrometry (Acetonitrile/H$_2$O) $\lambda_{max}$=231, 291; HRESI MS M+H=444.0085 $\Delta_{calc}$ C$_{21}$H$_{13}$N$_3$O$_2$Cl$_3$ (444.0073)=2.7 ppm; $^1$H NMR, see Table 1; $^{13}$C NMR, see Table 2.

Biological Assays

EXAMPLE 7

Antimicrobial Assays

Minimum inhibitory concentrations (MICs) are determined according to the National Committee for Clinical Laboratory Standards (NCCLS) susceptibility test guideline M7-A5 (Ferraro, M. 2001 Methods for Dilution Antimicrobial Susceptibility Tests for Bacteria that Grow Aerobically; Approved Standard (NCCLS). National Committee for Clinical Laboratory Standards (NCCLS), Villanova) to quantify the antimicrobial activity of the compounds of the present embodiment against various pathogenic bacteria. Susceptibility testing is performed by broth microdilution in accordance with National Committee for Clinical Laboratory Standards (NCCLS) guidelines. This procedure entails combining the test compounds with a standardized number of cells, incubating at the temperature and amount of time appropriate for each particular organism, and visually scoring the concentration at which no growth was apparent in the test wells. The panel includes both drug sensitive and drug resistant isolates of both gram-positive and gram-negative bacteria, including: *S. aureus* (both MSSA and MRSA), *S. pneumoniae* (wild type and penicillin-resistant), vancomycin-sensitive *E. faecalis*, vancomycin-resistant *E. faecium*, *E. coli*, *H. influenzae* and *P. aeruginosa*.

Susceptibility testing was performed by broth microdilution in accordance with National Committee for Clinical Laboratory Standards (NCCLS) guidelines. Antimicrobial data for compounds of Formulae II, III, IV, VI, VII, VIII, IX, XII, XIII, XIV, XV', XV, XVI, XVII, XVIII, XXI', XXII, XXIII, XXIV, and XXV are shown in Tables 3, 4 and 5. Table 5 displays the MIC values in micrograms per mL for bis-indole pyrrole compounds against *E. coli* imp.

TABLE 3

| | MIC (μg/ml) | | | |
|---|---|---|---|---|
| Organism | Compound of Formula III | Compound of Formula II | Compound of Formula IV | Compound of Formula VI |
| *S. aureus* - MSSA | 1.8 | 0.8 | 1.1 | 3 |
| *S. aureus* - MRSA | 2 | 1 | 1.5 | 3 |
| *S. epidermidis* - ATCC 700578 | 4 | 1 | 1 | 4 |
| *S. epidermidis* - ATCC 700582 | 4 | 1 | 1 | 4 |
| *S. pneumoniae* - penicillin sensitive | 24 | 8 | 20 | 24 |
| *S. pneumoniae* - penicillin resistant | 24 | 8 | 20 | 20 |
| *E. faecalis* - Van$^s$ | 8 | 1.5 | 2.5 | 8 |
| *E. faecium* - Van$^r$ | 8 | 2 | 2 | 8 |
| *E. coli* - imp | 16 | 6 | 6 | >32 |
| *E. coli* - ATCC 25922 | >32 | >32 | >32 | >32 |
| *H. influenzae* - ATCC 49766 | 12 | 6 | 6 | 8 |
| *H. influenzae* - ATCC 49247 | 16 | 2 | 4 | 5 |

TABLE 4

| Form # | MSSA 29213 MIC | MRSA 43300 MIC | Staph Epi 700578 MIC | Staph Epi 700582 MIC | S. pneumo 49619 Pen. S MIC | S. pneumo 51915 Pen R MIC | VSE 29212 MIC | VRE 700221 MIC | H. inf. 49247 | H. inf. 49766 |
|---|---|---|---|---|---|---|---|---|---|---|
| VII | 12* | 16* | 16* | 16* | >32* | >32* | >32* | >32* | >32* | >32* |
| VIII | >16 | >16 | >16 | >16 | >16 | >16 | >16 | >16 | >16 | >16 |
| IX | >32 | >32 | 16 | 16 | 32, >32 | >32 | >32 | >32 | >32 | >32 |
| XII | 4 | 6 | 3 | 6 | >32 | >32 | 8 | 8 | 8 | 10 |
| XIII | 3* | 4* | 8* | 8* | >32* | >32* | 16* | 32* | >32* | >32* |
| XIV | 6 | 6 | 8* | 8* | 32* | 24* | 12 | 6 | >32* | >32* |
| XV' | 1* | 1* | 1* | 1* | 16* | 16* | 4* | 4* | >32* | >32* |
| XVI | 1.4 | 2.5 | 2.5 | 2.5 | 20 | 24 | 5 | 6 | >32 | 16, >32 |
| XVII | 1* | 1* | 1* | 1* | 16* | 24* | 4* | 4* | >32* | 16* |
| XVIII | 8* | 12* | 16* | 16* | >32* | >32* | >32* | >32* | >32* | >32* |
| XX | 4 | 5 | 8 | 8 | 32 | >32, 32 | 24 | >32 | 16,4 | >32 |
| XXI'** | 0.5* | 0.75* | 1* | 1* | 16* | 16* | 2* | 4* | >32* | 16* |
| XXII | 1.25 | 1.5 | 2.5 | 2 | 32 | 32 | 6 | 16, >32 | 4, >32 | 4 |
| XXIII | 16* | >32* | >32* | 16* | >32* | >32* | >32* | >32* | >32* | >32* |
| XXIV | 1* | 1.5* | 2* | 2* | 23* | 16* | 4* | 8* | 16* | 16* |
| XXV | 4* | 8* | 8* | 8* | 32* | >32* | >32* | >32* | 8* | 16* |

All data reported as averages of 2 experiments except where indicated (*) or when the 2 values differ by >2 fold. In the latter case, both values are reported separately.
*Data reported as result of single experiment.
**Contains approximately 30% of the compound of Formula II.

TABLE 5

| Formula # | E. coli imp MIC (ug/mL) |
|---|---|
| VII | >32 |
| VIII | >16 |
| IX | >32 |
| XII | 20 |
| XIII | >32 |
| XV (XV') | 8 |
| XVI | >32, 32 |
| XVII | 8 |
| XVIII | >32 |
| XX | >32 |
| XXII | >32 |
| XXIII | >32 |
| XXIV | 8 |
| XXV | >32 |

Many of the compounds of the above formulae were potent versus both drug-sensitive and drug-resistant *Staphlyococci* and *Enterococci*, with good activity versus *Haemophilus influenzae* and one isolate of *Escherichia coli*, indicating a potent, broad-spectrum antibiotic. As can be observed from the above data, it appears that halogenation is beneficial for antimicrobial activity. The data also indicates that the presence of chlorine is beneficial for antimicrobial activity. Additionally, it appears that bromine substitution can be well tolerated in these bis-indole pyrroles to still yield highly effective antimicrobials.

EXAMPLE 8

Bactericidality

Bactericidality is assessed using time-kill kinetics (Hoellman, D. B. et al. 1998 *Antimicrob Agents Chemother* 42:857) on susceptible organism(s), preferably but not limited to: *B. anthracis, S. aureus, S. pneumoniae, E. faecalis, H influenzae, E. coli*.

EXAMPLE 9

Drug Synergy or Antagonism

Drug synergy or antagonism with current antimicrobial therapies (ciprofloxacin, doxycycline, ampicillin, chloramphenicol, norfloxacin, clindamycin, and vancomycin) is examined via checkerboard (Eliopoulos, G. M. & C. B. Wennersten 2002 *Antimicrob Agents Chemother* 46:1319) or time-kill techniques.

EXAMPLE 10

Innate or Acquired Drug Resistance

Innate or acquired drug resistance is evaluated by determining spontaneous resistance frequencies (Adrian, P. V. et al. 2000 *Antimicrob Agents Chemother* 44:3101) and resistance acquired upon long-term serial passage of *S. aureus* at sub-MIC compound concentrations (Choe, C. H. et al. 2000 *Antimicrob Agents Chemother* 44:1766). The compounds of the present embodiment show little or no emergence of resistance (spontaneous resistance frequency $<1\times10^{-8}$ or $10^{-9}$; <2 dilution shift in MIC over 22 serial passages at sub-lethal drug concentrations).

EXAMPLE 11

Evaluation of Maximum Tolerated Dose (MTD)

Acute MTD studies are performed on test mice with test concentrations ranging from 1 mg/kg to as high as achievable, not to exceed 50 mg/kg. Approximately 10 mg of material will be prepared to perform these studies. Compound will be introduced according to the microbial model's route of administration in single doses. These exploratory studies will begin with 5–10 mice per dose group, ascending to double the preceding concentration if the mice survive. The highest concentration at which >75% of the mice survive without observable distress can be considered MTD.

Pharmaceutical Formulations

EXAMPLE 12

Formulations Administered Intravenously, by Drip, Injection, or the Like

Vials containing 5 g of powdered glucose are each added aseptically with 10 mg of a compound synthesized by the method of the embodiment and sealed. After being charged with nitrogen, helium or other inert gas, the vials are stored in a cool, dark place. Before use, the contents are dissolved in ethanol and added to 100 ml of a 0.85% physiological salt water solution. The resultant solution is administered as a method of inhibiting the growth of a cancerous tumor in a human diagnosed as having such a tumor at between approximately 10 ml/day to approximately 1000 ml/day, intravenously, by drip, or via a subcutaneous or intraperitoneal injection, as deemed appropriate by those of ordinary skill in the art.

EXAMPLE 13

Formulation to be Administered Orally or the Like

A mixture obtained by thoroughly blending 1 g of a compound obtained and purified by the method of the embodiment, 98 g of lactose and 1 g of hydroxypropyl cellulose is formed into granules by any conventional method. The granules are thoroughly dried and sifted to obtain a granule preparation suitable for packaging in bottles or by heat sealing. The resultant granule preparations are orally administered at between approximately 100 ml/day to approximately 1000 ml/day, depending on the symptoms, as deemed appropriate by those of ordinary skill in the art of treating cancerous tumors in humans.

EXAMPLE 14

Preparation of Compounds of Formulae XXVII, XXVIII, and XXIX From the Compound of Formula II The compound of Formula II can be derivatized with various aminoalkyl halides in the presence of base, such as $K_2CO_3$, $Cs_2CO_3$ or NaH to produce various compounds of the general formulae XXVII, XXVIIII, and XXIX. The substitution can occur at one or more of the nitrogens of Formula II. Mixtures can be separated chromatographically to obtain pure compounds.

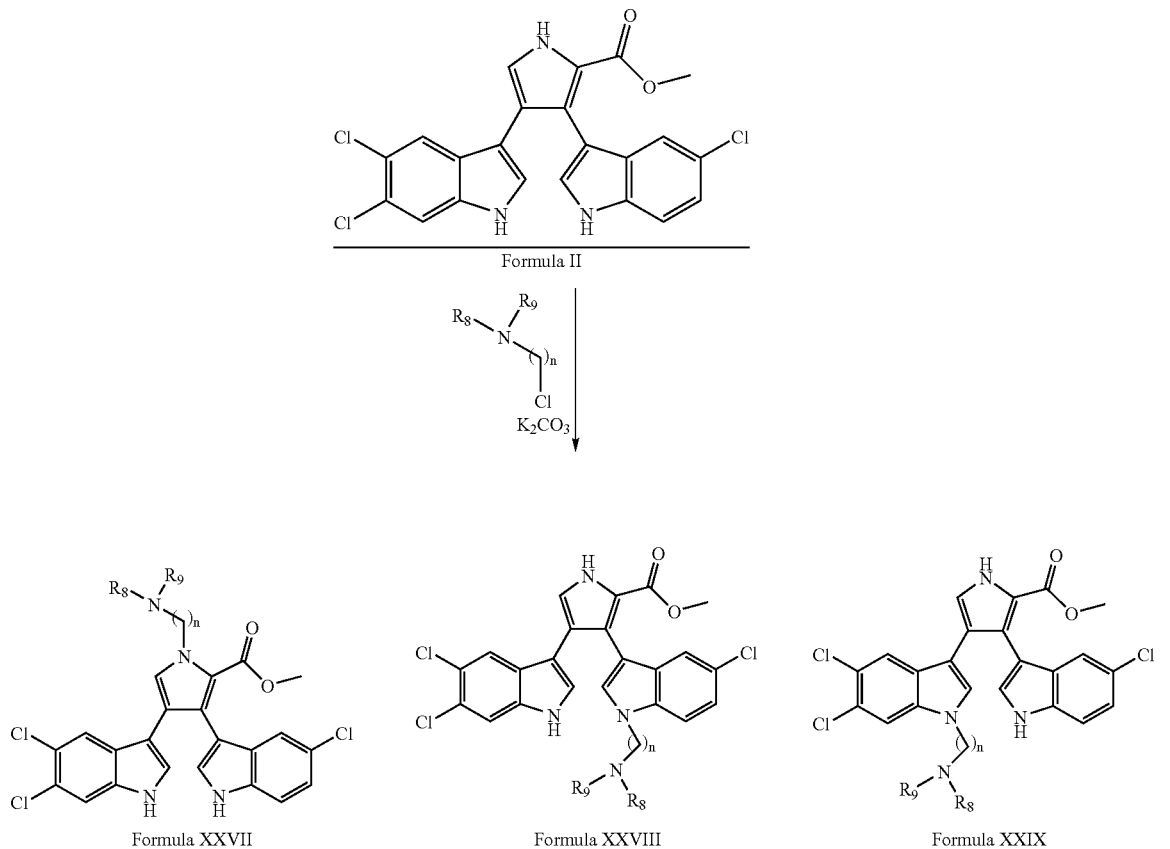

EXAMPLE 15

Preparation of Compounds of Formula XXXI From the Compound of Formula II

Amide derivatives of the compound of Formula II can be prepared by hydrolysis of the methyl ester to produce the carboxylic acid of Formula XII, which is then followed by peptide coupling to form the corresponding amide of Formula XXXI:

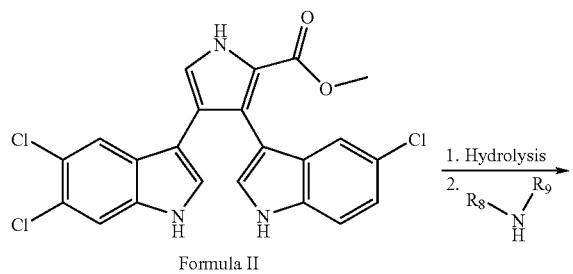

-continued

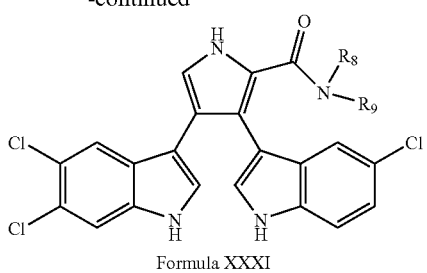

EXAMPLE 16

Preparation of Compound of Formula XXX from the Compound of Formula II

The compound of Formula II can be derivatized with various sugars (with all protected, some protected, or unprotected hydroxyl groups) in the presence of $PPh_3$ (Triphenylphosphine), DEAD (Diethylazodicarboxylate) at low temperatures to produce various sugar derivatives, for example, the compound of Formula XXX. The substitution can occur at one or more of the nitrogens of Formula II with or without preference. Mixtures can be separated chromatographically to obtain pure compounds.

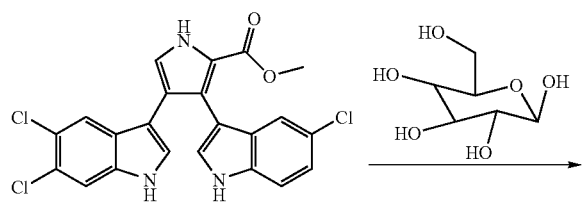

Formula II

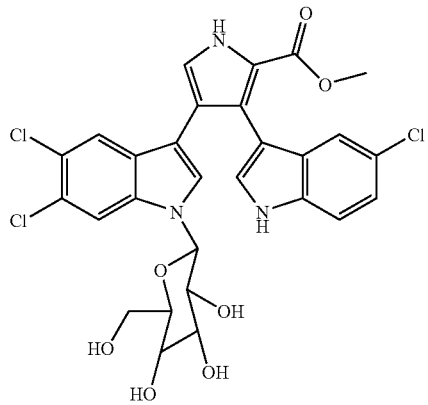

Formula XXX

EXAMPLE 17

Figure 4:
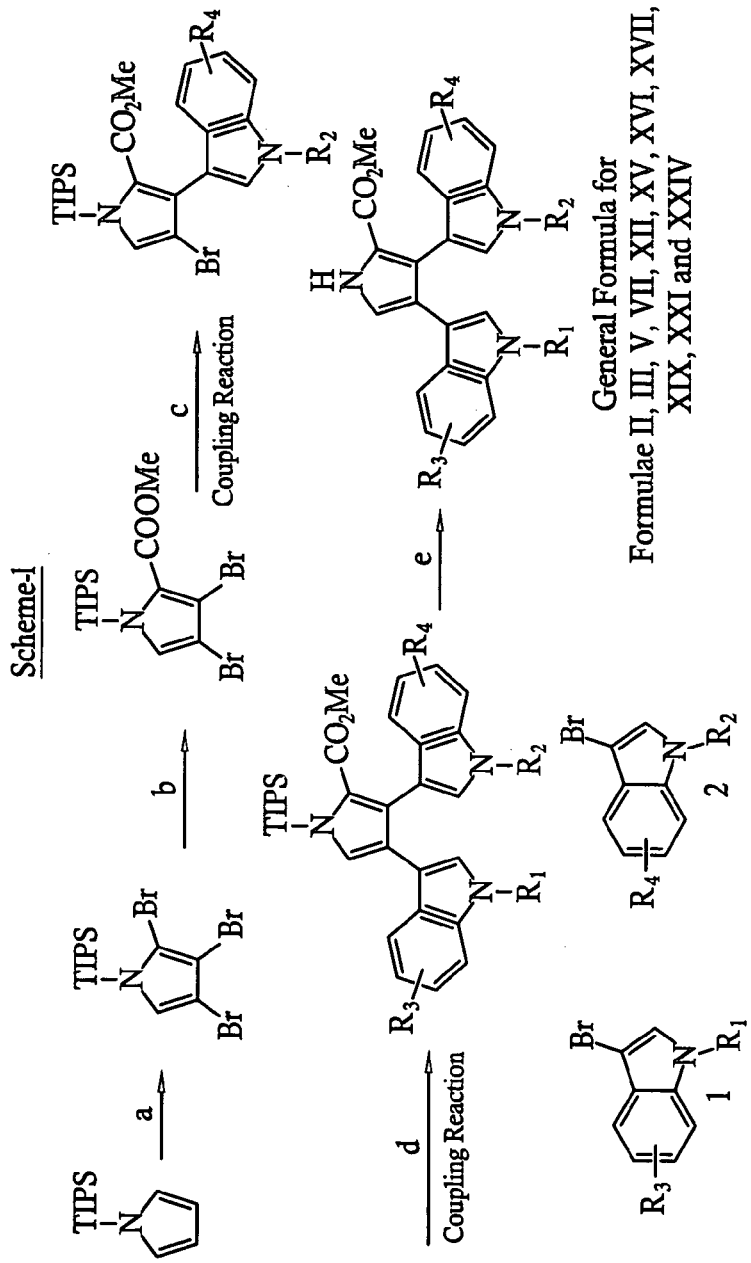
FIG. 4 depicts scheme-I involving Negishi coupling reactions.

General Synthetic Method to Prepare Compounds of Formula II, III, VII, XII, XV, XVI, XVII, XIX, XXI, XXIV and V Formulas II, III, VII, XII, XV, XVI, XVII, XIX, XXI, XXIV and V can be synthesized by known coupling reactions such as Stille, Suzuki and Negishi coupling reactions on bromopyrrole with various halogenated indole building blocks. Scheme-I, depicted in FIG. 4, is the general method using Negishi coupling reactions. The compound of Formula V can be synthesized using 3-bromo-5,6-dichloroindole as a building block in scheme-I. NBS is N-Bromosuccinimide, TIPS is Triisopropylsilyl, PhLi is Phenyl lithium, THF is Tetrahydrofuran, PPh3 is Triphenylphosphine, and TBAF is Tetrabutylammonium fluoride.

The examples described above are set forth solely to assist in the understanding of the embodiments. Thus, those skilled in the art will appreciate that the methods can provide derivatives of compounds.

One skilled in the art would readily appreciate that the present invention is well adapted to carry out the objects and obtain the ends and advantages mentioned, as well as those inherent therein. The methods and procedures described herein are presently representative of preferred embodiments and are exemplary and are not intended as limitations on the scope of the invention. Changes therein and other uses will occur to those skilled in the art which are encompassed within the spirit of the invention.

It will be readily apparent to one skilled in the art that varying substitutions and modifications can be made to the embodiments disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably can be practiced in the absence of any element or elements, limitation or limitations which is not specifically disclosed herein. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention. Thus, it should be understood that although the present invention has been specifically disclosed by preferred embodiments and optional features, modification and variation of the concepts herein disclosed can be resorted to by those skilled in the art, and that such modifications and variations are considered to be falling within the scope of the embodiments of the invention.

What is claimed is:

1. A method of treating a microbial infection comprising administering a compound having a structure of Formula I, and pharmaceutically acceptable salts and pro-drug esters thereof:

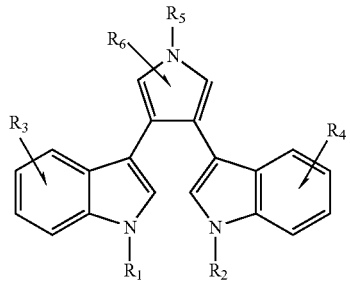

Formula I wherein a ring can include one or more additional heteroatoms, such as nitrogen, sulfur or oxygen; and can include a non-nitrogen hetero-atom, such as sulfur or oxygen, in place of a nitrogen(s) in Formula I; and wherein each of a $R_1$, a $R_2$, five $R_3$, five $R_4$, a $R_5$, and two $R_6$ is independently selected from the group consisting of a hydrogen atom, a halogen, a sugar, an aminoalkyl, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl, —CO—O—$R_7$, carbonyl —CCO—$R_7$, —CO—N$R_8R_9$, —(CH$_2$)$_n$—COO$R_7$, —CO—(CH$_2$)$_n$—COO$R_7$, —(CH$_2$)$_n$—N$R_8R_9$, ester, alkoxycarbonyl, aryloxycarbonyl, wherein n is an integer from 1 to 6, wherein each $R_7$, $R_8$ and $R_9$ is separately selected from the group consisting of a hydrogen atom, halogen atom, mono-substituted, poly-substituted or unsubstituted variants of the following residues: saturated $C_1$–$C_{24}$ alkyl, unsaturated $C_2$–$C_{24}$ alkenyl or $C_2$–$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl, a 5-membered ring, a 6-membered ring, or combination thereof.

2. The method of claim 1, wherein at least one of the $R_1$, $R_2$, the five $R_3$, the five $R_4$, $R_5$, and the two $R_6$ substitutions is asymmetric.

3. The method of claim 1, wherein the two $R_6$ substitutions are asymmetric.

4. The method of claim 1, wherein the five $R_4$ and the five $R_3$ substitutions are asymmetric.

5. The method of claim 1, wherein at least of the five $R_3$ is a halogen atom and at least one $R_4$ is a halogen atom, and the indole rings do not include additional hetero-atoms, but do include the indole nitrogen.

6. The method of claim 1, wherein $R_8$ is —$(CH_2)_2$— and $R_9$ is —$(CH_2)_2$—, wherein $R_8$ and $R_9$ are directly connected to each other so as to form a five membered ring.

7. The method of claim 6, wherein $R_8$ is —$(CH_2)_2$— and $R_9$ is —$(CH_2)_2$—, wherein $R_8$ and $R_9$ are connected to each other via $R_{10}$ so as to form a six membered ring, wherein $R_{10}$ is selected from the group consisting of $CH_2$, NH, O, and S.

8. The method of claim 5, wherein
one of the two $R_6$ is an alkoxy carbonyl;
one of the $R_6$ is a hydrogen atom;
at least one of the five $R_3$ is a chloride atom; and
$R_1$, $R_2$, and $R_5$ are each hydrogen atoms.

9. The method of claim 8, wherein the alkoxy carbonyl is a methoxy carbonyl.

10. The method of claim 1 further comprising:
identifying a subject that would benefit from administration of an antimicrobial agent;
administering the compound to the subject.

11. The method of claim 1, wherein the microbial infection is an infection of at least one a gram positive bacterium.

12. The method of claim 1, wherein the microbial infection is an infection of at least *E. faecalis*-Vans.

13. The method of claim 1, wherein the microbial infection is an infection of at least *H. influenzae*.

* * * * *

UNITED STATES PATENT AND TRADEMARK OFFICE
CERTIFICATE OF CORRECTION

PATENT NO. : 7,166,634 B2
APPLICATION NO. : 11/040923
DATED : January 23, 2007
INVENTOR(S) : Mitchell et al.

It is certified that error appears in the above-identified patent and that said Letters Patent is hereby corrected as shown below:

Title Page;
On the first page, Col. 2 (Other Publications), line 12, please delete "Pharamacological" and insert --Pharmacological--, therefor.

In Col. 7, lines 5-6, please delete "—CH$_2$)$_n$-NR$_8$R$_9$," and insert -- —(CH$_2$)$_n$-NR$_8$R$_9$,--, therefor.

In Col. 7, line 6, please delete "alkoxycarbonly," and insert --alkoxycarbonyl,--, therefor.

In Col. 7, line 31-32 (approx.), please delete "membered-ring," and insert --membered ring,--, therefor.

In Col. 10, line 65, please delete "C1" and insert --Cl--, therefor.

In Col. 11, line 9, please delete "C1" and insert --Cl--, therefor.

In Col. 31, line 47 (approx.), please delete "$\alpha_{calc}$" and insert --$\Delta_{calc}$--, therefor.

In Col. 32, line 1, please delete "$\alpha_{calc}$" and insert --$\Delta_{calc}$--, therefor.

In Col. 43, line 53, please delete "drip" and insert --drip,--, therefor.

In Col. 51, line 2, please delete "m/min" and insert --ml/min--, therefor.

In Col. 51, lines 59-60 (approx.), please delete "(Acetonitrile/H2O)" and insert --(Acetonitrile/H$_2$O)--, In Col. 51, lines 64-65, please delete "(Acetonitrile/H2O)" and insert --(Acetonitrile/H$_2$O)--, therefor.

In Col. 52, line 15, please delete "7-azatryptoiphan" and insert --7-azatryptophan--, therefor.

In Col. 52, line 45 (approx.), below "analogs." please insert --Purification--. (as subheading)

UNITED STATES PATENT AND TRADEMARK OFFICE
CERTIFICATE OF CORRECTION

PATENT NO. : 7,166,634 B2
APPLICATION NO. : 11/040923
DATED : January 23, 2007
INVENTOR(S) : Mitchell et al.

It is certified that error appears in the above-identified patent and that said Letters Patent is hereby corrected as shown below:

In Col. 53, line 22, please delete "acid/H2O" and insert --acid/$H_2O$--, therefor.

In Col. 54, line 21, please delete "$^1$NMR" and insert --$^1$H NMR--, therefor.

In Col. 61, line 47, please delete "PPh3" and insert --$PPh_3$--, therefor.

Signed and Sealed this

Nineteenth Day of August, 2008

JON W. DUDAS
*Director of the United States Patent and Trademark Office*